(12) United States Patent
Matray et al.

(10) Patent No.: US 12,275,851 B2
(45) Date of Patent: *Apr. 15, 2025

(54) POLYMERIC TANDEM DYES WITH LINKER GROUPS

(71) Applicant: SONY GROUP CORPORATION, Tokyo (JP)

(72) Inventors: Tracy Matray, Snohomish, WA (US); Sharat Singh, Rancho Santa Fe, CA (US)

(73) Assignee: SONY GROUP CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/891,807

(22) Filed: Aug. 19, 2022

(65) Prior Publication Data

US 2023/0012304 A1 Jan. 12, 2023

Related U.S. Application Data

(63) Continuation of application No. 17/323,791, filed on May 18, 2021, now Pat. No. 11,453,783, which is a continuation of application No. 16/982,355, filed as application No. PCT/US2019/021327 on Mar. 8, 2019.

(60) Provisional application No. 62/646,234, filed on Mar. 21, 2018.

(51) Int. Cl.
| | | |
|---|---|---|
| *C09B 69/10* | (2006.01) | |
| *C07F 9/53* | (2006.01) | |
| *G01N 1/30* | (2006.01) | |
| *G01N 33/52* | (2006.01) | |
| *G01N 33/58* | (2006.01) | |

(52) U.S. Cl.
CPC .............. *C09B 69/102* (2013.01); *C07F 9/53* (2013.01); *C07F 9/5304* (2013.01); *C07F 9/5329* (2013.01); *C09B 69/105* (2013.01); *C09B 69/109* (2013.01); *G01N 1/30* (2013.01); *G01N 33/582* (2013.01); *G01N 2001/302* (2013.01)

(58) Field of Classification Search
CPC ... C09B 69/102; C09B 69/105; C09B 69/109; G01N 33/582

See application file for complete search history.

(56) References Cited

U.S. PATENT DOCUMENTS

| | | | |
|---|---|---|---|
| 4,450,305 A | 5/1984 | Kamhi | |
| 4,476,229 A | 10/1984 | Fino et al. | |
| 4,778,753 A | 10/1988 | Yamanishi et al. | |
| 5,053,054 A | 10/1991 | Kirchanski | |
| 5,268,486 A | 12/1993 | Waggoner et al. | |
| 5,318,894 A | 6/1994 | Pugia | |
| 5,582,977 A | 12/1996 | Yue et al. | |
| 5,698,391 A | 12/1997 | Cook et al. | |
| 5,886,177 A | 3/1999 | Cook et al. | |
| 5,994,143 A | 11/1999 | Bieniarz et al. | |
| 6,005,093 A | 12/1999 | Wood et al. | |
| 6,140,480 A | 10/2000 | Kool | |
| 6,171,859 B1 | 1/2001 | Herrnstadt et al. | |
| 6,218,108 B1 | 4/2001 | Kool | |
| 6,365,730 B1 | 4/2002 | Jennings et al. | |
| 6,380,431 B1 | 4/2002 | Whipple et al. | |
| 6,479,650 B1 | 11/2002 | Kool | |
| 6,514,700 B1 | 2/2003 | Singh | |
| 6,534,041 B1 | 3/2003 | Licha et al. | |
| 6,627,400 B1 | 9/2003 | Singh et al. | |
| 6,670,193 B2 | 12/2003 | Kool | |
| 6,716,452 B1 | 4/2004 | Piccariello et al. | |
| 6,852,709 B2 | 2/2005 | Leong et al. | |
| 7,038,063 B2 | 5/2006 | Lee et al. | |
| 7,060,708 B2 | 6/2006 | Piccariello et al. | |
| 7,172,907 B2 | 2/2007 | Chen et al. | |
| 7,423,133 B2 | 9/2008 | Kool et al. | |
| 7,667,024 B2 | 2/2010 | Mao et al. | |

(Continued)

FOREIGN PATENT DOCUMENTS

| | | |
|---|---|---|
| CA | 2263671 A1 | 2/1998 |
| CN | 102174078 A | 9/2011 |

(Continued)

OTHER PUBLICATIONS

"What is an Analyte?," Google Search, dated Mar. 22, 2018, retrieved from https://www.google.com/search?q=what+is+an+analyte&rlz=ICIGCEB_enUS775US775&oq=what+is+an+analyte&aqs=chrome..69i57j015.3231j0j7&s . . . 2 pages.

(Continued)

*Primary Examiner* — Jezia Riley

(74) *Attorney, Agent, or Firm* — Seed IP Law Group LLP

(57) ABSTRACT

Compounds useful as fluorescent or colored dyes are disclosed. The compounds have the following structure (I):

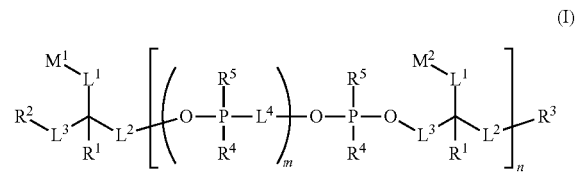

or a stereoisomer, tautomer or salt thereof, wherein $R^1$, $R^2$, $R^3$, $R^4$, $R^5$, $L^1$, $L^2$, $L^3$, $L^4$, $M^1$, $M^2$, m and n are as defined herein. Methods associated with preparation and use of such compounds is also provided.

25 Claims, 7 Drawing Sheets

(56) References Cited

U.S. PATENT DOCUMENTS

| | | |
|---|---|---|
| 7,897,684 B2 | 3/2011 | Bazan et al. |
| 8,008,522 B2 | 8/2011 | Lukhtanov et al. |
| 8,101,776 B2 | 1/2012 | Berens et al. |
| 8,153,706 B2 | 4/2012 | Vasudevan |
| 8,217,389 B2 | 7/2012 | Nakano et al. |
| 8,293,700 B2 | 10/2012 | Arranz |
| 8,349,308 B2 | 1/2013 | Yurkovetskiy et al. |
| 8,354,515 B2 | 1/2013 | Ueno et al. |
| 8,431,545 B2 | 4/2013 | Kataoka et al. |
| 8,491,993 B2 | 7/2013 | Nguyen et al. |
| 8,546,590 B2 | 10/2013 | Gall |
| 8,632,947 B2 | 1/2014 | Bentley et al. |
| 8,802,738 B2 | 8/2014 | Emrick |
| 8,895,023 B2 | 11/2014 | Rademacher et al. |
| 8,906,603 B2 | 12/2014 | Castro et al. |
| 8,946,394 B2 | 2/2015 | Na et al. |
| 9,029,537 B2 | 5/2015 | Koch |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,696,310 B2 | 7/2017 | Margulies et al. |
| 9,714,946 B2 | 7/2017 | Bradner et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,910,051 B2 | 3/2018 | Beacham et al. |
| 9,913,992 B2 | 3/2018 | Demarest et al. |
| 9,932,578 B2 | 4/2018 | Feinstein et al. |
| 9,939,454 B2 | 4/2018 | Dzubay et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,617,670 B2 | 4/2020 | Sapra et al. |
| 10,709,791 B2 | 7/2020 | Stayton et al. |
| 10,834,091 B2 | 11/2020 | Deninno et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,013,756 B2 | 5/2021 | Haruta et al. |
| 11,084,932 B2 | 8/2021 | Battrell et al. |
| 11,142,647 B2 | 10/2021 | Matray et al. |
| 11,312,736 B1 | 4/2022 | Matray et al. |
| 11,352,502 B2 | 6/2022 | Matray et al. |
| 11,370,922 B2 | 6/2022 | Matray et al. |
| 11,377,563 B2 | 7/2022 | Matray et al. |
| 11,390,754 B2 | 7/2022 | Singh et al. |
| 11,434,374 B2 | 9/2022 | Matray et al. |
| 11,434,377 B2 | 9/2022 | Matray et al. |
| 11,453,783 B2 | 9/2022 | Matray et al. |
| 11,618,906 B2 | 4/2023 | Steele et al. |
| 11,685,835 B2 | 6/2023 | Matray |
| 11,827,661 B2 | 11/2023 | Battrell et al. |
| 11,874,280 B2 | 1/2024 | Jackson et al. |
| 11,931,419 B2 | 3/2024 | Matray |
| 11,945,955 B2 | 4/2024 | Matray et al. |
| 12,006,438 B2 | 6/2024 | Singh et al. |
| 12,018,159 B2 | 6/2024 | Matray et al. |
| 2001/0018503 A1 | 8/2001 | Whipple et al. |
| 2002/0012947 A1 | 1/2002 | Bevers et al. |
| 2002/0099013 A1 | 7/2002 | Piccariello et al. |
| 2002/0142329 A1 | 10/2002 | Matray et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0067498 A1 | 4/2004 | Chenna et al. |
| 2004/0096825 A1 | 5/2004 | Chenna et al. |
| 2004/0138467 A1 | 7/2004 | French et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2012/0126175 A1 | 5/2012 | Ueno et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2014/0023590 A1 | 1/2014 | Gao et al. |
| 2014/0193504 A1 | 7/2014 | Wooley et al. |
| 2014/0275508 A1 | 9/2014 | Scarr et al. |
| 2015/0030541 A1 | 1/2015 | Rogers |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0292957 A1 | 10/2017 | Matray et al. |
| 2017/0326233 A1 | 11/2017 | Demeule et al. |
| 2018/0065998 A1 | 3/2018 | Battrell et al. |
| 2018/0092993 A1 | 4/2018 | Desai et al. |
| 2018/0141935 A1 | 5/2018 | Josel et al. |
| 2018/0312468 A1 | 11/2018 | Zhang et al. |
| 2019/0016898 A1 | 1/2019 | Matray et al. |
| 2019/0136065 A1 | 5/2019 | Singh et al. |
| 2019/0144678 A1 | 5/2019 | Matray et al. |
| 2019/0153232 A1 | 5/2019 | Matray et al. |
| 2019/0177549 A1 | 6/2019 | Matray et al. |
| 2019/0300716 A1 | 10/2019 | Matray et al. |
| 2020/0032139 A1 | 1/2020 | Behrendt et al. |
| 2020/0164085 A1 | 5/2020 | Brandish et al. |
| 2020/0222554 A1 | 7/2020 | Matray et al. |
| 2020/0330610 A1 | 10/2020 | Desai et al. |
| 2020/0353089 A1 | 11/2020 | Matray |
| 2020/0353094 A1 | 11/2020 | Matray |
| 2020/0360526 A1 | 11/2020 | Matray |
| 2021/0032277 A1 | 2/2021 | Matray et al. |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0139440 A1 | 5/2021 | Ramsden et al. |
| 2021/0253864 A1 | 8/2021 | Matray et al. |
| 2021/0261782 A1 | 8/2021 | Matray et al. |
| 2021/0285953 A1 | 9/2021 | Matray et al. |
| 2021/0340380 A1 | 11/2021 | Matray et al. |
| 2021/0395530 A1 | 12/2021 | Matray et al. |
| 2022/0160887 A1 | 5/2022 | Matray et al. |
| 2022/0168433 A1 | 6/2022 | Matray et al. |
| 2022/0168435 A1 | 6/2022 | Matray et al. |
| 2022/0175951 A1 | 6/2022 | Boitano et al. |
| 2022/0220314 A1 | 7/2022 | Singh et al. |
| 2022/0227794 A1 | 7/2022 | Matray et al. |
| 2022/0305127 A1 | 9/2022 | Thomas et al. |

(56) References Cited

U.S. PATENT DOCUMENTS

| | | |
|---|---|---|
| 2022/0372297 A1 | 11/2022 | Matray et al. |
| 2022/0380603 A1 | 12/2022 | Matray et al. |
| 2022/0402963 A1 | 12/2022 | Matray et al. |
| 2023/0012304 A1 | 1/2023 | Matray et al. |
| 2023/0129481 A1 | 4/2023 | Matray et al. |
| 2024/0043455 A1 | 2/2024 | Battrell et al. |
| 2024/0092820 A1 | 3/2024 | Matray et al. |
| 2024/0132725 A1 | 4/2024 | Sherif |
| 2024/0207423 A1 | 6/2024 | Matray |
| 2024/0210408 A1 | 6/2024 | Jackson et al. |
| 2024/0248094 A1 | 7/2024 | Matray et al. |
| 2024/0255514 A1 | 8/2024 | Matray et al. |
| 2024/0287313 A1 | 8/2024 | Sherif |
| 2024/0287314 A1 | 8/2024 | Matray et al. |

FOREIGN PATENT DOCUMENTS

| | | |
|---|---|---|
| CN | 103319378 A | 9/2013 |
| CN | 104072727 A | 10/2014 |
| CN | 106589005 A | 4/2017 |
| CN | 107106685 A | 8/2017 |
| CN | 107709470 A | 2/2018 |
| CN | 109153860 A | 1/2019 |
| EP | 0708837 B1 | 3/2006 |
| GB | 2 372 256 A | 8/2002 |
| GB | 2 554 666 A | 4/2018 |
| JP | S61-207395 A | 9/1986 |
| JP | H04-282391 A | 10/1992 |
| JP | 2000-17183 A | 1/2000 |
| JP | 2003532092 A | 10/2003 |
| JP | 2014527071 A | 10/2014 |
| JP | 2016534107 A | 11/2016 |
| JP | 2017504659 A | 2/2017 |
| JP | 2017-124994 A | 7/2017 |
| JP | 2018507863 A | 3/2018 |
| JP | 2018515628 A | 6/2018 |
| JP | 2019516807 A | 6/2019 |
| JP | 2019516821 A | 6/2019 |
| JP | 2021518410 A | 8/2021 |
| JP | 7069033 B2 | 5/2022 |
| KR | 20030032939 A | 4/2003 |
| KR | 10-1041446 B1 | 6/2011 |
| KR | 10-2015-0007795 A | 1/2015 |
| KR | 20160022358 A | 2/2016 |
| KR | 20180005650 A | 1/2018 |
| KR | 10-2020-0133374 A | 11/2020 |
| KR | 20210032434 A | 3/2021 |
| KR | 102530707 B1 | 5/2023 |
| SU | 1121931 A1 | 4/1988 |
| WO | WO-93/009128 A1 | 5/1993 |
| WO | 95/02700 A1 | 1/1995 |
| WO | WO 9506731 A2 | 3/1995 |
| WO | 98/32463 A2 | 7/1998 |
| WO | 01/73123 A2 | 10/2001 |
| WO | WO 0222883 A1 | 3/2002 |
| WO | 02/083954 A1 | 10/2002 |
| WO | 2004/007751 A2 | 1/2004 |
| WO | 2007/094135 A1 | 8/2007 |
| WO | WO 2009113645 A1 | 9/2009 |
| WO | 2010/026957 A1 | 3/2010 |
| WO | 2013/012687 A2 | 1/2013 |
| WO | WO 2014102803 A1 | 7/2014 |
| WO | 2014/147642 A1 | 9/2014 |
| WO | WO 2015091953 A1 | 6/2015 |
| WO | WO 2015155753 A2 | 10/2015 |
| WO | WO-2016183185 A1 | 11/2016 |
| WO | WO-2016183461 A1 | 11/2016 |
| WO | 2017/003639 A2 | 1/2017 |
| WO | WO 2017062271 A2 | 4/2017 |
| WO | 2017/089890 A1 | 6/2017 |
| WO | WO 2017094897 A1 | 6/2017 |
| WO | WO-2017173348 A1 | 10/2017 |
| WO | WO-2017173355 A1 | 10/2017 |
| WO | WO-2017177065 A2 | 10/2017 |
| WO | WO 2017197144 A1 | 11/2017 |
| WO | WO 2018045278 A1 | 3/2018 |
| WO | 2019/126691 A1 | 6/2019 |
| WO | WO 2019140227 A1 | 7/2019 |
| WO | WO 2019182765 A1 | 9/2019 |
| WO | WO 2019182766 A1 | 9/2019 |
| WO | 2020/006285 A1 | 1/2020 |
| WO | 2020/219959 A1 | 10/2020 |
| WO | WO 2021062176 A2 | 4/2021 |

OTHER PUBLICATIONS

Arian et al., "1,9-Dialkoxyanthracene as a $^1O_2$-Sensitive Linker," *J. Am. Chem. Soc.* 133:3972-3980, 2011.

Aviñó et al., "Solid-phase synthesis of oligomers carrying several chromophore units linked by phosphodiester backbones," *Bioorganic & Medicinal Chemistry Letters* 18:2306-2310, 2008.

Avirah et al., "Infrared Absorbing Croconaine Dyes: Synthesis and Metal Ion Binding Properties," *J. Org. Chem.* 73(1):274-279, 2008.

Babitskaya et al., "Bromoacyl Analogues of Phosphatidycholine with Intramolecular Fluorescence Quenching and Their Use as Substrates for Continuous Monitoring of Phospholipase $A_2$ Activity," *Applied Biochemistry and Microbiology* 40(4):351-356, 2004.

Bag et al., "Triazolyl-donor-acceptor chromophore-decorated unnatural amino acids and peptides: FRET events in a β-turn conformation," *Chem. Commun.* 50:433-435, 2014.

Beaucage et al., "The Functionalization of Oligonucleotides via Phosphoramidite Derivatives," *Tetrahedron* 49(10):1925-1963, 1993.

Becker et al., "New Thermotropic Dyes Based on Amino-Substituted Perylendicarboximides," *Chem. Eur. J.* 6(21):3984-3990, 2000.

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015.

Bergstrom et al., "Potent Promise," *Innovations in Pharmaceutical Technology* 49:16-20, 2014.

Bergstrom et al., "XMT-1522 induces tumor regressions in pre-clinical models representing HER2-positive and HER2 low-expressing breast cancer," Mersana Therapeutics, Abstract P4-14-28, 2015, 1 page.

Boldyrev et al., "Synthesis and Characteristics of New Fluorescent Probes Based on Cardiolipin," *Russian Journal of Bioorganic Chemistry* 35(2):219-224, 2009.

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Breul et al., "Fluorescent monomers as building blocks for dye labeled polymers: synthesis and application in energy conversion, biolabeling and sensors," *Chem. Soc. Rev.* 42(12):5366-5407, 2013.

Brinkley, "A brief survey of methods for preparing protein conjugates with dyes, haptens, and cross-linking reagents," *Bioconjugate Chem* 3:2-13, 1992.

Buckhout-White et al., "Assembling programmable FRET-based photonic networks using designer DNA scaffolds," *Nature Communications* 5:5615, Dec. 11, 2014. (16 pages).

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

CAS Registry No. 862288-26-4, American Chemical Society, 2021. (1 page).

Chang et al., "A General Approach for Generating Fluorescent Probes to Visualize Piconewton Forces at the Cell Surface," *J. Am. Chem. Soc.* 138:2901-2904, 2016. (4 pages).

(56) References Cited

OTHER PUBLICATIONS

Chattopadhyay et al., "Brilliant Violet Fluorophores: A New Class of Ultrabright Fluorescent Compounds for Immunofluorescence Experiments," *Cytometry Part A* 81A:456-466, 2012.
Chong et al., "Oxygen Quenching of Pyrene-Lipid Fluorescence in Phosphatidylcholine Vesicles—A Probe for Membrane Organization," *Biophys. J.* 47:613-621, 1985.
Cuppoletti et al., "Oligomeric fluorescent labels for DNA," *Bioconjug. Chem.* 16(3):528-534, 2005.
Dai et al., "DNA-polyfluorophore excimers as sensitive reporters for esterases and lipases," *Chem. Commun.* 46:1221-1223, 2010.
Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
DiVittorio et al., "Synthetic peptides with selective affinity for apoptotic cells," *Org. Biomol. Chem.* 4:1966-1976, 2006.
Doi et al., "Hetero-Selective DNA-Like Duplex Stabilized by Donor-Acceptor Interactions," *Chem. Eur. J.* 21:15974-15980, 2015.
Drescher et al., "General Synthesis and Aggregation Behaviour of New Single-Chain Bolaphospholipids: Variations in Chain and Headgroup Structures," *Chemistry—A European Journal* 14(22):6796-6804, 2008.
Dubrovsky, "Semiconductor nanoparticles as reporters in multiplexed immunoassay and cell analysis," *International Journal of Nanoscience* 8(1 & 2): 163-167, 2009.
Franceschin et al., "Synthesis of a Dibromoperylene Phosphoramidite Building Block and its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.
Gao et al., "Libraries of Composite Polyfluors Built from Fluorescent Deoxyribosides," *Journal of the American Chemical Society* 124:11590-11591, 2002.
Gao et al., "Modified DNA Analogues That Sense Light Exposure with Color Changes," *Journal of the American Chemical Society* 126:12748-12749, 2004.
Gordon et al., "Analysis of simulated and experimental fluorescence recovery after photobleaching. Data for two diffusing components," *Biophysical Journal* 68:766-778, 1995.
Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.
Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.
Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.
Haraguchi, "Live Cell Imaging: Approaches for Studying Protein Dynamics in Living Cells," *Cell Structure and Function* 27:333-334, 2002.
Jain et al. "Current ADC Linker Chemistry," *Pharm. Res.* 32:3526-3540, 2015.
Johansson, "Choosing Reporter-Quencher Pairs for Efficient Quenching Through Formation of Intramolecular Dimers," *Methods in Molecular Biology* 335:17-29, 2006.
Kashida et al., "A Cationic Dye Triplet as a Unique "Glue" That Can Connect Fully Matched Termini of DNA Duplexes," *Chem. Eur. J.* 17:2614-2622, 2011.
Koo et al., "Fluorescent DNA chemosensors: identification of bacterial species by their volatile metabolites," *Chemical Communications* 47:11435-11437, 2011.
Kozma et al., "Fluorescent Ligands for Adenosine Receptors," *Bioorganic & Medicinal Chemistry Letters* 23: 26-36, 2013.
Krueger at al., "Fluorescent Amino Acids: Modular Building Blocks for the Assembly of New Tools for Chemical Biology," *ChemBioChem* 14:788-799, 2013.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Lewis et al., "Orientation Control of Fluorescence Resonance Energy Transfer Using DNA as a Helical Scaffold," *J. Am. Chem. Soc.* 127(28):10002-10003, 2005.
Li et al., "Polymeric Drugs: Advances in the development of pharmacologically active polymers," *Journal of Controlled Release* 219:369-382, 2015.
Li et al., "Responsive nanogel-based dual fluorescent sensors for temperature and $Hg^{2+}$ions with enhanced detection sensitivity," *J. Mater. Chem.* 20:10716-10723, 2010.
Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010 (14 Pages).
Luo et al., "Sensitive and rapid quantification of C-reactive protein using quantum dot-labeled microplate immunoassay," *Journal of Translational Medicine* 10(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Masuko et al., "Fluorescence resonance energy transfer from pyrene to perylene labels for nucleic acid hybridization assays under homogenous solution conditions," *Nucleic Acids Research* 28(8):e34, 2000 (8 pages).
Kozytska et al., Mersana Therapeutics, URL= http://www.mersana.com, download date Jan. 3, 2019, 9 pages.
Molotkovsky et al., "Perylenoyl- and Anthrylvinyl-Labeled Lipids as Membrane Probes," *Biochimica et Biophysica Acta* 778:281-288, 1984.
Moss, "Nomenclature of Fused and Bridged Fused Ring Systems," *Pure & Appl. Chem.* 70(1):143-216, 1998.
Nussbaumer et al., "Amplification of Chirality by Supramolecular Polymerization of Pyrene Oligomers," *Angewandte Chemie International Edition* 50:5490-5494, 2011.
Paris et al., "Probing DNA sequences in solution with a monomer-excimer fluorescence color change," *Nucleic Acids Research* 26(16):3789-3793, 1998.
Petreus et al., "Polyester imides containing main-chain phosphorus," *Revue Roumaine de Chimie* 34(8):971-978, 1994 (with English Abstract).
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Pownall et al., "Kinetics of Spontaneous and Plasma-Stimulated Sphingomyelin Transfer," *Biochimica et Biophysica Acta* 712:169-176, 1982.
PubChem, "U.S. Pat. No. 20100012929A1-20100121-C00010_4," SID No. 140452858, retrieved Mar. 29, 2016 from URL https://pubchem.ncbi.nlm.nih.gov/substance/140452858#sectio . . . , 6 pages.
Ren et al., "An Antisense Oligodeoxynucleotide-Doxorubicin Conjugate: Preparation and its Reversal Multidrug Resistance of Human Carcinoma Cell Line In Vitro," *Nucleosides, Nucleotides & Nucleic Acids* 23(10):1595-1607, 2004.
Rochat et al., "Water-Soluble Cationic Conjugated Polymers: Response to Electron-Rich Bioanalytes," *J. Am. Chem. Soc.* 135:17703-17706, 2013.

(56) References Cited

OTHER PUBLICATIONS

RN 230952-79-1, Registry Database Compound, 1999.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," *J. Am. Chem. Soc.* 126(3):780-790, 2006.
Saito et al., "Dual-labeled oligonucleotide probe for sensing adenosine via FRET: A novel alternative to SNPs genotyping," *Chem. Commun.*:2133-2135, 2007.
Singh et al., "Multiplexed measurement of membrane protein populations," *Caplus* 2003:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE* 9939(993904):1-10, 2016.
Stuart et al., "Site-Specific DNA-Doxorubicin Conjugates Display Enhanced Cytotoxicity to Breast Cancer Cells," *Bioconjugate Chemistry* 25:406-413, 2014.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "High yield production of high molecular weight poly-(ethylene glycol)/ α-cyclodextrin polyrotaxanes by aqueous one-pot approach," *Polymer* 53:2884-2889, 2012.
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Teyssot et al., "Aromatic Nitrogen Donors for Efficient Copper(1)-NHC CuAAC under Reductant-Free Conditions," *Eur. J. Org. Chem.* 3507-3515, 2010.
Tram et al., "Oligonucleotide Labeling Using BODIPY Phosphoramidite," *Nucleosides, Nucleotides & Nucleic Acids* 30(1):1-11, 2011.
Vinogradov et al., "Total synthesis and biochemical characterization of mirror image barnase," *Chem Sci.* 6: 2997-3002, 2015.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007 (18 Pages).
Winiger et al., "Long-Distance Electronic Energy Transfer in Light-Harvesting Supramolecular Polymers," *Angew. Chem. Int. Ed.* 53:13609-13613, 2014.
Yurkovetskiy et al., "Advantages of Polyacetal Polymer-based Antibody Drug Conjugates: Application to Low Expression Targets," Mersana Therapeutics, technical paper #2645, 2014, 1 page.

Zhang et al., "FRET Imaging of Enzyme-Responsive HPMA Copolymer Conjugate," *Macromolecular Bioscience* 17(1600125):1-8, 2017.
Zhao et al., "Mussel-Inspired One-Pot Synthesis of a Fluorescent and Water-Soluble Polydopamine-Polyethyleneimine Copolymer," *Macromol. Rapid Commun.* 36:909-915, 2015.
Rui Zhang et al: "FRET Imaging of Enzyme-Responsive HPMA Copolymer Conjugate", Macromolecular Bioscience, vol. 17, No. 1, Jan. 1, 2017, p. 1600125 (sub-pp. 1-8), XP055591040.
Bargh et al., "Cleavable linkers in antibody-drug conjugates," *Chemical Society Reviews* 48(16):4361-4374, Aug. 21, 2019. (15 pages).
CAPLUS Accession No. 1991:467753, Mielewczyk et al., "5' end fluorescent labelling of oligonucleotides with riboflavin-derived phosphitylating reagent," *Acta Biochimica Polonica* 36(3-4):225-233, 1989. (1 page).
CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (1 page).
CAPLUS Accession No. 1995:733249, WO9506731A2, filed Mar. 9, 1995. (1 page).
CAPLUS Accession No. 1995:849926, Reed et al., "Structure-Activity Relationships of Cytotoxic Cholesterol-Modified DNA Duplexes," *Journal of Medicinal Chemistry* 38(22):4587-4596, Oct. 27, 1995. (1 page).
CAPLUS Accession No. 1997:497709, Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (1 page).
Chen et al., "Synthesis and properties of new segmented block poly(urethane-urea)s containing phosphatidylcholine analogues and polybutadienes," *Macro-Molecular Chemistry and Physics* 197(5):1587-1597, May 1996. (11 pages).
Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (10 pages).
Ciccotelli et al., "Polyguanine-conjugated antigens for scavenger receptor targeting and self-adjuvanting vaccines (VAC13P.1125)," *The Journal of Immunology* 194(Suppl. 1): 214.5, May 1, 2015 [Abstract]. (1 page).
Dropulic et al., "Update on New Antivirals Under Development for the Treatment of Double-Stranded DNA Virus Infections," *Clinical Pharmacology & Therapeutics* 88(5):610-619, Nov. 2010.
Finniss et al., "A versatile acid-labile linker for antibody-drug conjugates," Med. Chem, Commun; 5; Apr. 1, 2014, 4 pages.
Franzini et al., "Identification of Structure-Activity Relationships from Screening a Structurally Compact DNA-Encoded Chemical Library," *Angewandte Chemie International Edition* 54:3927-3931, Feb. 3, 2015 [with supporting information]. (41 pages).
Gupta et al., "Dendrimers: Novel Polymeric Nanoarchitectures for Solubility Enhancement," *Biomacromolecules* 7(3):649-658, Mar. 2006 [Published online Feb. 15, 2006]. (10 pages).
Hasegawa et al., "Cysteine, histidine and glycine exhibit anti-inflammatory effects in human coronary arterial endothelial cells," *Clinical and Experimental Immunology* 167:269-274, Jan. 11, 2012. (6 pages).
Irani et al., "Molecular properties of human IgG subclasses and their implications for designing therapeutic monoclonal antibodies against infectious diseases," *Molecular Immunology* 67:171-182, 2015.
Khandare et al., "Polymer-drug conjugates: Progress in polymeric prodrugs," *Progress in Polymer Science* 31(4):359-397, Apr. 2006. (39 pages).
Kolpashchikov, "Binary Probes for Nucleic Acid Analysis," *Chemical Reviews* 110(8):4709-4723, Jun. 28, 2010. (15 pages).
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.

(56) References Cited

OTHER PUBLICATIONS

Liso et al., "Polymeric drugs derived from Ibuprofen with improved antiinflammatory profile," *Journal of Biomedical Materials Research* 32:553-560, Dec. 1996. (8 pages).

Liu et al., "Imidazole inhibits autophagy flux by blocking autophagic degradation and triggers apoptosis via increasing FoxO3a-Bim expression," *International Journal of Oncology* 46:721-731, Feb. 2015. (11 pages).

Liu et al., "Increased Cytotoxicity and Decreased In Vivo Toxicity of FdUMP[10] Relative to 5-FU," *Nucleosides & Nucleotides* 18(8):1789-1802, Aug. 1999. (14 pages).

Marras et al., "Efficiencies of fluorescence resonance energy transfer and contact-mediated quenching in oligonucleotide probes," *Nucleic Acids Research* 30(21):e122, Nov. 1, 2002. (8 pages).

McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.

Midoux et al., "Chemical vectors for gene delivery: a current review on polymers, peptides and lipids containing histidine or imidazole as nucleic acids carriers," *British Journal of Pharmacology* 157:166-178, May 2009. (13 pages).

Mielewczyk et al., "5' end fluorescent labelling of oligonucleotides with riboflavin-derived phosphitylating reagent," *Acta Biochimica Polonica* 36(3-4):225-233, 1989. (9 pages).

Mthembu et al., "Breaking a Couple: Disulfide Reducing Agents," *ChemBioChem* 21, 2020. (10 pages).

Nolting, "Linker Technology for Antibody-Drug Conjugates," in Ducry (ed.), *Antibody—Drug Conjugates*, Humana Press, Totowa, NJ, 2013, Ch. 5, pp. 71-100.

Oh et al., "Low-dose guanidine and pyridostigmine: relatively safe and effective long-term symptomatic therapy in Lambert-Eaton myasthenic syndrome," *Muscle & Nerve* 20:1146-1152, Sep. 1997. (7 pages).

Pawelczyk et al., "Molecular Consortia-Various Structural and Synthetic Concepts for More Effective Therapeutics Synthesis," *International Journal of Molecular Sciences* 19:1104, Apr. 6, 2018. (19 pages).

Pelegrin et al., "Antiviral Monoclonal Antibodies: Can They Be More Than Simple Neutralizing Agents?" *Trends in Microbiology* 23(10):653-665, Oct. 2015.

Petersen et al., "Acyclic, achiral enamide nucleoside analogues. The importance of the C=C bond in the analogue for its ability to mimic natural nucleosides," *Organic & Biomolecular Chemistry* 1:3293-3296, Sep. 4, 2003. (4 pages).

Poupart et al., "Aminopropargyl derivative of terpyridine-bis(methylenamine) tetraacetic acid chelate of europium (Eu (TMT)-AP3): a new reagent for fluorescent labelling of proteins and peptides," *Org. Biomol. Chem.* 4:4165-4177, Oct. 2006.

Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (24 pages).

Reed et al., "Structure-Activity Relationships of Cytotoxic Cholesterol-Modified DNA Duplexes," *Journal of Medicinal Chemistry* 38(22):4587-4596, Oct. 27, 1995. (10 pages).

Samal et al., "Cationic polymers and their therapeutic potential," *Chemical Society Reviews* 41:7147-7194, Aug. 2012. (48 pages).

Shuey et al., "Cyclohexanediol Bisphosphates as Models for Phospholipid-Metal Ion Binding Sites," *Bioorganic Chemistry* 21:95-108, Mar. 1993. (14 pages).

Shuman et al., "Bacterial DNA repair by non-homologous end joining," *Nature Reviews Microbiology* 5:852-861, Nov. 2007.

STIC Search Report from American Chemical Society, for U.S. Appl. No. 17/255,353, dated Sep. 7, 2023. (143 pages).

Striebel et al., "Enhancing sensitivity of human herpes virus diagnosis with DNA microarrays using dendrimers," *Experimental and Molecular Pathology* 77:89-97, Oct. 2004 [Published online Jul. 15, 2004]. (9 pages).

Sun et al., "Self-assembled biodegradable micellar nanoparticles of amphiphilic and cationic block copolymer for siRNA delivery," *Biomaterials* 29:4348-4355, available online Aug. 2008. (8 pages).

Tabujew et al., "Chapter One: Functionalization of Cationic Polymers for Drug Delivery Applications," *RSC Polymer Chemistry Series 13*, 2015. (29 pages).

Wang et al., "Novel dexamethasone-HPMA copolymer conjugate and its potential application in treatment of rheumatoid arthritis," *Arthritis Research & Therapy* 9(1):R2, Jan. 18, 2007. (9 pages).

Wu Yi et al., "$\varepsilon^{Py}$ A-Modified Oligodeoxyadenylates: Expanded Fluorescence Phenomena and Structural Formation," *Chemistry—An Asian Journal* 7:60-63, Nov. 2011. (4 pages).

Yu et al., "Targeted Delivery of an Anti-Inflammatory PDE4 Inhibitor to Immune Cells via an Antibody-drug Conjugate," *Molecular Therapy* 24(12):2078-2089, Dec. 2016.

Kozytska et al., "Discovery of the novel, homogenous payload platform Dolasynthen for Antibody-Drug Conjugates," Mersana Therapeutics, Abstract #272, 2018. (1 page).

Lee et al., "The spectroscopic analysis for binding of amphipathic and antimicrobial model peptides containing pyrenylalanine and tryptophan to lipid bilayer," *Biochimica et Biophysica Acta* 984:174-182, Sep. 4, 1989. (9 pages).

Lvnitski et al., "Introducing charge transfer functionality into prebiotically relevant β-sheet peptide fibrils," *Chemical Communications* 50:6733-6736, May 12, 2014. (4 pages).

Xu et al., "Synthesis of [D-Pyrenylalanine4,4'] gramicidin S by Solid-Phase-Synthesis and Cyclization-Cleavage Method with Oxime Resin," *Chemistry Letters* 21:191-194, Feb. 1992. (4 pages).

POLYMERIC TANDEM DYES WITH LINKER GROUPS

BACKGROUND

Field

The present invention is generally directed to dimeric and polymeric chromophore compounds (e.g., polymer compounds comprising fluorescent dye moieties) having spacing groups, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of dyes compatible with aqueous systems that can elucidate desired spatial information and biomolecule interactions.

Accordingly, techniques involving resonance energy transfer have been developed to reveal such structural information. Specifically, Förster resonance energy transfer ("FRET"—sometimes also used interchangeably with fluorescence resonance energy transfer) techniques produce information that reliably measures change biomolecular distances and interactions. Resonance energy transfer techniques are relatively cheap and measurements can be obtained rapidly; however, FRET suffers from several limitations related to the orientation and positioning of chromophores as well as energy transfer masking due to free fluorophores and undesirable pH sensitivity.

There is thus a need in the art for water soluble dyes, especially resonance energy transfer dyes, having an increased molar brightness and/or increased FRET emission signal. Ideally, such dyes and biomarkers should be intensely colored or fluorescent and should be available in a variety of colors and fluorescent wavelengths. The present invention Mills this need and provides further related advantages.

BRIEF SUMMARY

In brief, embodiments of the present invention are generally directed to compounds useful as water soluble, fluorescent and/or colored dyes and/or probes that enable visual detection of analyte molecules, such as biomolecules, as well as reagents for their preparation. In particular, in some embodiments, the compounds of this disclosure are useful because they enable FRET fluorescence emission associated with the same. Methods for visually detecting analyte molecules using the dyes are also described.

Embodiments of the presently disclosed dyes include two or more fluorescent and/or colored moieties (i.e., chromophores) covalently linked by a linker ("$L^4$"). In contrast to previous reports of dimeric and/or polymeric dyes, the present dyes are significantly brighter than the corresponding monomeric dye compound and enable FRET absorbance and emission as a result of intramolecular interactions. While, not wishing to be bound by theory, it is believed that particular linkers provide sufficient proximity between the fluorescent and/or colored moieties such that intramolecular FRET is optimized.

The water soluble, fluorescent or colored dyes of embodiments of the invention are intensely colored, enable FRET processes (e.g., absorbance, emission, Stokes shifts) and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained as well as valuable spatial information about target molecules.

In one embodiment, compounds having the following structure (I) are provided:

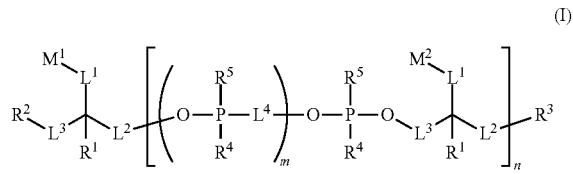

(I)

or a stereoisomer, tautomer or salt thereof, wherein $R^1$, $R^2$, $R^3$, le, $R^5$, $L^1$, $L^2$, $L^3$, $L^4$, $M^1$, $M^2$, in and n are as defined herein.

Another embodiment provides a compound having the following structure (II):

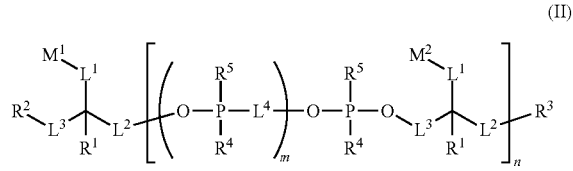

(II)

or a stereoisomer, salt or tautomer thereof, wherein $R^1$, $R^2$, $R^3$, $R^4$, $R^5$, $L^1$, $L^2$, $L^3$, $L^4$, $M^1$, $M^2$, m and n are as defined herein.

Yet another embodiment provides a polymer compound comprising an acceptor chromophore having an acceptor transition dipole moment and being covalently linked to a polymer backbone, and a donor chromophore having a donor transition dipole moment and being covalently linked to the polymer backbone, wherein the polymer compound adopts a confirmation in solution at physiological conditions wherein the effective distance between the acceptor chromophore and the donor chromophore is less than about 50.0 nm and the acceptor transition dipole and the donor transition dipole are substantially parallel.

The foregoing embodiments describe compounds that find utility in a number of applications, including use as FRET dyes, fluorescent and/or colored dyes in various analytical methods.

In another embodiment, a method for staining a sample is provided, the method comprises adding to said sample one of the foregoing compounds in an amount sufficient to produce an optical response when said sample is illuminated at an appropriate wavelength.

In still other embodiments, the present disclosure provides a method for visually detecting an analyte molecule, comprising:

(a) providing one of the foregoing compounds (e.g., a compound of structure (I) or structure (II)); and
(b) detecting the compound by its visible properties.

Other disclosed methods include a method for visually detecting a biomolecule, the method comprising:

(a) ad-mixing one of the foregoing compounds (e.g., a compound of structure (I) or structure (II)) with one or more biomolecules; and
(b) detecting the compound by its visible properties.

Other embodiments are directed to a composition comprising at least one of the foregoing compounds (e.g., a compound of structure (I) or structure (II)) and one or more biomolecules. Use of such compositions in analytical methods for detection of the one or more analyte (e.g., biomolecules) is also provided.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
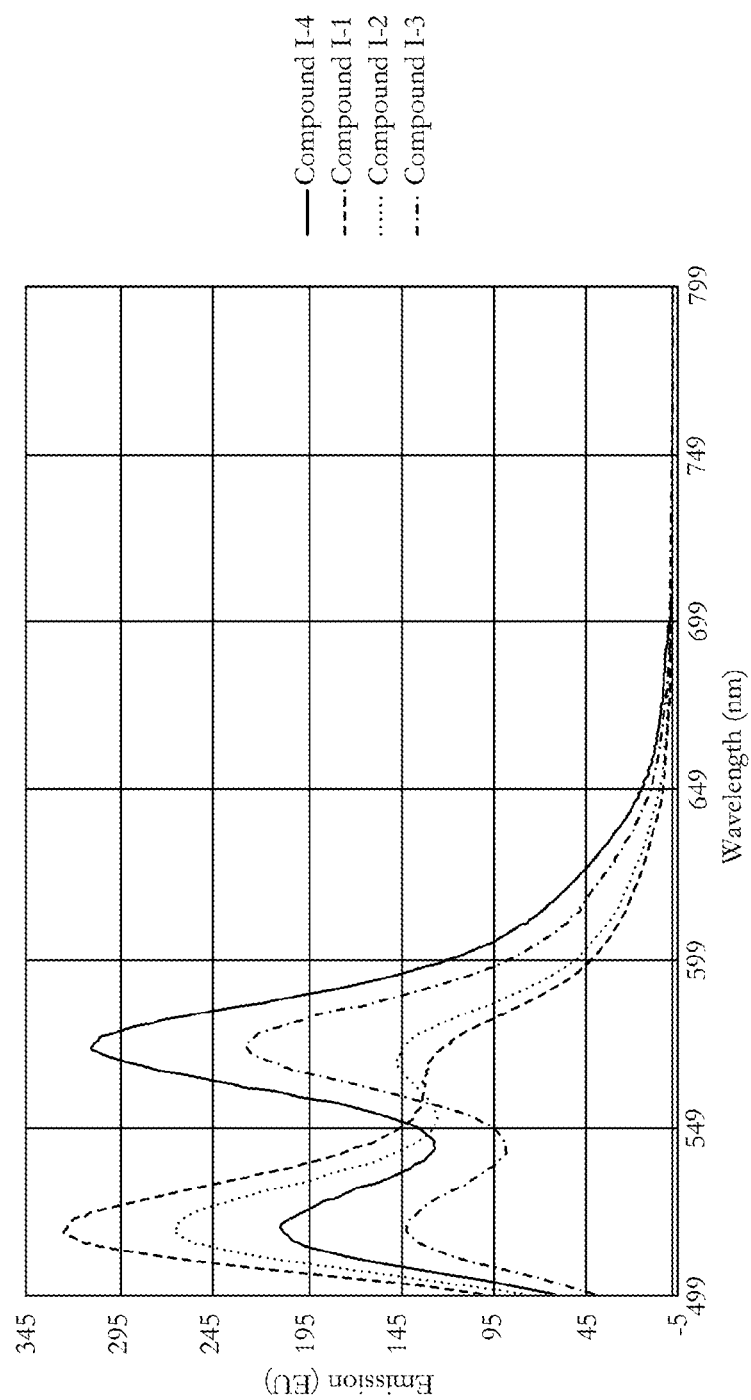
FIG. 1 shows the emission spectra of Compounds I-1 through I-4, each having various spacer lengths between pendant boron-dipyrromethene ("BODIPY") and fluorescein-based chromophores.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.
"Carboxy" refers to the —$CO_2H$ group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —$NO_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —O$R_a$ where $R_a$ is an alkyl group as defined above containing one to twelve carbon atoms. Unless stated otherwise specifically in the specification, an alkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C," "HEG," "TEG," "PEG 1K" and variations thereof, linking groups illustrated below:

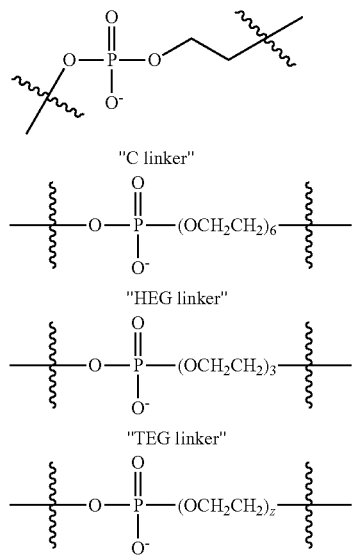

"C linker"

"HEG linker"

"TEG linker"

"EG linker"
z > 0; e.g., z = 3-10

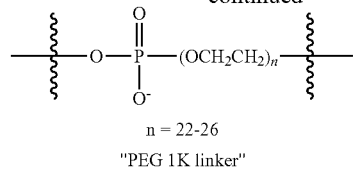

n = 22-26
"PEG 1K linker"

Multimers of the above C-linker, HEG linker and/or PEG 1K linker are included in various embodiments of heteroalkylene linkers.

In some embodiments,

In some embodiments of the PEG 1K linker, n is 25. Multimers may comprise, for example, the following structure:

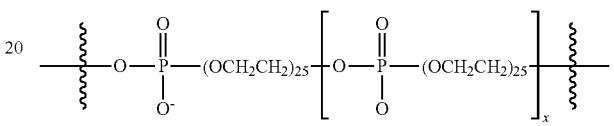

wherein x is 0 or an integer greater than 0, for example, x ranges from 0-100 (e.g., 1, 2, 3, 4, 5, 6, 7, 8, 9 or 10).

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatom. Exemplary heteroatomic linkers include single atoms selected from the group consisting of O, N, P and S, and multiple heteroatoms for example a linker having the formula —P(O⁻)(=O)O— or —OP(O⁻)(=O)O— and multimers and combinations thereof.

"Phosphate" refers to the —OP(=O)($R_a$)$R_b$ group, wherein $R_a$ is OH, O⁻ or O$R_c$; and $R_b$ is OH, O⁻, O$R_c$, a thiophosphate group or a further phosphate group, wherein $R_c$ is a counter ion (e.g., Na+ and the like).

"Phosphoalkyl" refers to the —OP(=O)($R_a$)$R_b$ group, wherein $R_a$ is OH, O⁻ or O$R_c$; and $R_b$ is —Oalkyl, wherein $R_c$ is a counter ion (e.g., Na⁺ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Phosphoalkylether" refers to the —OP(=O)($R_a$)$R_b$ group, wherein $R_a$ is OH, O⁻ or O$R_c$; and $R_b$ is —Oalkylether, wherein $R_c$ is a counter ion (e.g., Na⁺ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphate" refers to the —OP(=$R_a$)($R_b$)$R_c$ group, wherein $R_a$ is O or S, $R_b$ is OH, O⁻, S⁻, O$R_d$ or S$R_d$; and $R_c$ is OH, SH, O⁻, S⁻, OR$_d$, SR$_d$, a phosphate group or a further thiophosphate group, wherein R$_d$ is a counter ion (e.g., Na⁺ and the like) and provided that: i) R$_a$ is S; ii) R$_b$ is S⁻ or SR$_d$; iii) R$_c$ is SH, S⁻ or SR$_d$; or iv) a combination of i), ii) and/or iii).

"Thiophosphoalkyl" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkyl, wherein R$_d$ is a counter ion (e.g., Na+ and the like) and provided that: i) R$_a$ is S; ii) R$_b$ is S⁻ or SR$_d$; or is S and R$_b$ is S⁻ or SR$_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphoalkylether" refers to the —OP(=R$_a$)(R$_b$)R$_c$ group, wherein R$_a$ is O or S, R$_b$ is OH, O⁻, S⁻, OR$_d$ or SR$_d$; and R$_c$ is —Oalkylether, wherein R$_d$ is a counter ion (e.g., Na⁺ and the like) and provided that: i) R$_a$ is S; ii) R$_b$ is S⁻ or SR$_d$; or iii) R$_a$ is S and R$_b$ is S⁻ or SR$_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated othenvise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopynolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

The suffix "-ene" refers to a particular structural feature (e.g., alkyl, aryl, heteroalkyl) attached to the rest of the molecule through a single bond and to the radical group through a single bond. In other words, the suffix "-ene" refers to a particular structural feature having the description given herein which is a linker between the molecule and a radical group. The points of attachment of the "-ene" chain to the rest of the molecule and to the radical group can be through one atom of or any two atoms within the chain. For example, an alkyleneheteroalkylene refers to a linker comprising a alkylene portion and a heteroalkylene portion.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

"FRET" refers to Förster resonance energy transfer refers to a physical interaction whereby energy from the excitation of one moiety (e.g., a first chromophore or "donor") is transferred to an adjacent moiety (e.g., a second chromophore or "acceptor"). "FRET" is sometimes also used interchangeably with fluorescence resonance energy transfer (i.e., when each chromophore is a fluorescent moiety). Generally, FRET requires that (1) the excitation or absorption spectrum of the acceptor chromophore overlaps with the emission spectrum of the donor chromophore; (2) the transition dipole moments of the acceptor and donor chromophores are substantially parallel (i.e., at about 0° or 180°); and (3) the acceptor and donor chromophores share a spatial proximity (i.e., close to each other). The transfer of energy from the donor to the acceptor occurs through non-radiative dipole-dipole coupling and the distance between the donor chromophore and acceptor chromophore is generally much less than the wavelength(s) of light.

"Donor" or "donor chromophore" refers to a chromophore (e.g., a fluorophore) that is or can be induced into an excited electronic state and may transfer its excitation energy to a nearby acceptor chromophore in a non-radiative fashion through long-range dipole-dipole interactions. Without wishing to be bound by theory, it is thought that the energy transfer occurs because the oscillating dipoles of the respective chromophores have similar resonance frequencies. A donor and acceptor that have these similar resonance frequencies are referred to as a "donor-acceptor pair(s)," which is used interchangeably with "FRET moieties" or "FRET dyes."

"Acceptor" or "acceptor chromophore" refers to a chromophore (e.g., a fluorophore) to which excitation energy from a donor chromophore is transferred via a non-radiative transfer through long-range dipole-dipole interaction.

"Stoke's shift" refers to a difference between positions (e.g., wavelengths) of the band maxima of absorption and emission spectra of an electronic transition (e.g., from excited state to non-excited state, or vice versa). In some embodiments, the compounds have a Stoke's shift greater than 25 nm, greater than 30 nm, greater than 35 nm, greater than 40 nm, greater than 45 nm, greater than 50 nm, greater than 55 nm, greater than 60 nm, greater than 65 nm, greater than 70 nm, greater than 75 nm, greater than 80 nm, greater than 85 nm, greater than 90 nm, greater than 95 nm, greater than 100 nm, greater than 110 nm, greater than 120 nm, greater than 130 nm, greater than 140 nm, greater than 150 nm, greater than 160 nm, greater than 170 nm, greater than 180 nm, greater than 190 nm, or greater than 200 nm.

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

"Physiological conditions" refers to a solution or medium having a temperature ranging from about 20 to 40° C., an atmospheric pressure of about 1 atm (101 kPa or 14.7 psi), a pH of about 6 to 8, a glucose concentration of about 1 to 20 mM, atmospheric oxygen concentration, and/or earth gravity. "Physiological conditions" includes a solution or medium having a subset of these properties (e.g., having a temperature ranging from 20 to 40° C. and a pH of about 6 to 8). Such conditions may also include buffer components or systems including, but not limited to phosphate, bicarbonate, hemoglobin and/or protein.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structures (I) or (II) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive group (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

"Bio-conjugation" or "bio-conjugate" and related variations refer to a chemical reaction strategy for forming a stable covalent bond between two molecules. The term "bio-conjugation" is generally used when one of the molecules is a biomolecule (e.g., an antibody), but can be used to describe forming a covalent bond with a non-biomolecule (e.g., a polymeric resin). The product or compound resulting from such a reaction strategy is a "conjugate," "bio-conjugate" or a grammatical equivalent.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Non-limiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The polymer compounds of various embodiments of the invention are useful for a wide variety of analytical applications, such as biochemical and biomedical applications, in which there is a need to determine the presence, location, spatial interaction or quantity of a particular analyte (e.g., biomolecule). In another aspect, therefore, the invention provides a method for visually detecting a biomolecule, comprising: (a) providing a biological system with a visually detectable biomolecule comprising the compound of the embodiments disclosed herein (e.g., structure (I) or structure (II)) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Non-limiting examples of such biological systems include cells, cell extracts, tissue samples, electrophoretic gels, assay mixtures, and hybridization reaction mixtures.

"Solid support" or "solid support residue" refers to any solid substrate known in the art for solid-phase support of molecules, for example a "microparticle" refers to any of a number of small particles useful for attachment to compounds of the invention, including, but not limited to, glass beads, magnetic beads, polymeric beads, non-polymeric beads, and the like. In certain embodiments, a microparticle comprises polystyrene beads.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I) or (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur; such a description includes instances where the event or circumstance occurs and instances where it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the wan "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I or II), or their salts, tautomers or solvates may contain one or more stereocenters and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)—, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable.

The present invention contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as FRET, fluorescent and/or colored dyes in various analytical methods are provided. In other embodiments, compounds useful as synthetic intermediates for preparation of compounds useful as FRET, fluorescent and/or colored dyes are provided. In general terms, embodiments of the present invention are directed to dimers and higher polymers of FRET, fluorescent and/or colored moieties. The FRET, fluorescent and/or colored moieties are linked by a linking moiety. Without wishing to be bound by theory, it is believed the linker helps to maintain sufficient spatial distance/proximity between the donor-acceptor pair (s) such that intramolecular quenching is reduced or eliminated, while maintain sufficient proximity to facilitate the non-radiative transfer of energy.

Accordingly, in some embodiments the compounds have the following structure (A):

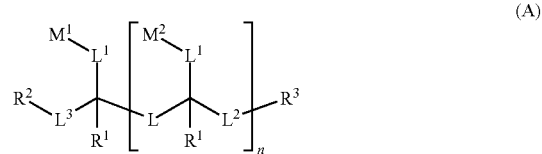

wherein L is a linker sufficient to maintain spatial separation between one or more (e.g., each) M group so that intramolecular quenching is reduced or eliminated, and $R^1$, $R^2$, $R^3$, $L^1$, $L^2$, $L^3$ and n are as defined for structure (I) or structure (II).

In other embodiments is provided a compound having the following structure (I):

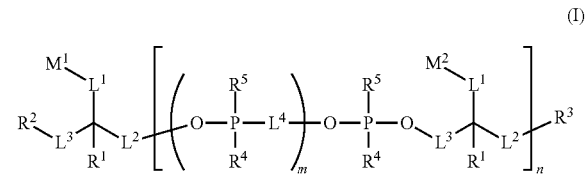

or a stereoisomer, salt or tautomer thereof, wherein:
  $M^1$ and $M^2$ are, at each occurrence, independently a chromophore, provided that at least one occurrence of $M^1$ and $M^2$ combine to form a FRET donor-acceptor pair;
  $L^1$ is, at each occurrence, an optional linker;
  $L^2$ and $L^3$ are, at each occurrence, independently an optional alkylene, alkenylene, alkynylene, heteroalkylene, heteroalkenylene, heteroalkynylene or heteroatomic linker;

L⁴ is, at each occurrence, independently an alkylene or heteroalkylene linker;

R¹ is, at each occurrence, independently H, alkyl or alkoxy;

R² and R³ are each independently H, OH, SH, alkyl, alkoxy, alkylether, heteroalkyl, —OP(=R$_a$)(R$_b$)R$_c$, Q, or a protected form thereof, or L';

R⁴ is, at each occurrence, independently OH, SH, O⁻, S⁻, OR$_d$ or SR$_d$;

R⁵ is, at each occurrence, independently oxo, thioxo or absent;

R$_a$ is O or S;

R$_b$ is OH, SH, O⁻, S⁻, OR$_d$ or SR$_d$;

R$_c$ is OH, SH, O⁻, S⁻, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

R$_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater; and n is an integer of one or greater.

In some embodiments, at least one occurrence of L⁴ is heteroalkylene. In more specific embodiments, the heteroalkylene comprises alkylene oxide. In some related embodiments, the heteroalkylene comprises ethylene oxide.

In embodiments, at least one occurrence of L⁴ is alkylene. In some more specific embodiments, at least one alkylene is ethylene. In some embodiments, the alkylene is ethylene at each occurrence.

In some embodiments, L¹ is, at each occurrence, independently an optional alkylene, alkenylene, alkynylene, heteroalkylene, heteroalkenylene, heteroalkynylene or heteroatomic linker. In some embodiments, L¹ is a linker comprising a functional group capable of formation by reaction of two complementary reactive groups (e.g., an azide and an alkyne). In some embodiments, L¹ is, at each occurrence, independently an optional alkylene, alkenylene, alkynylene, heteroalkylene, heteroalkenylene, heteroalkynylene, alkyleneheteroarylenealkylene, alkyleneheterocyclylenealkylene, alkylenecarbocyclylenealkylene, heteroalkyleneheteroarylenealkylene, heteroalkyleneheterocyclylenealkylene, heteroalkylenecarbocyclylenealkylene, heteroalkyleneheteroaryleneheteroalkylene, heteroalkyleneheterocycyleneheteroalkylene, heteroalkylenecarbocyclyleneheteroalkylene, alkyleneheteroaryleneheteroalkylene, alkyleneheterocyclyleneheteroalkylene, alkylenecarbocyclyleneheteroalkylene, heteroarylene, heterocyclylene, carbocyclylene, alkyleneheteroarylene, alkyleneheterocyclylene, heteroarylenealkylene, alkylenecarbocyclylene, carbocyclylenealkylene, heteroalkyleneheteroarylene, heteroalkyleneheterocyclylene, heteroaryleneheteroalkylene, heteroalkylenecarbocyclylene, carbocyclyleneheteroalkylene or heteroatomic linker. In some embodiments, L¹ is optionally substituted.

In some embodiments, the compound has the following structure (IA):

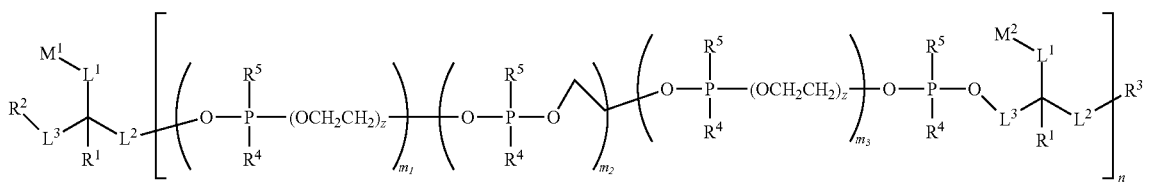

(IA)

wherein:

z is, at each occurrence, independently an integer from 1 to 100; and m₁, m₂ and m₃ are, at each occurrence, independently an integer from 0 to 6.

In some other embodiments, the compound has the following structure (IB):

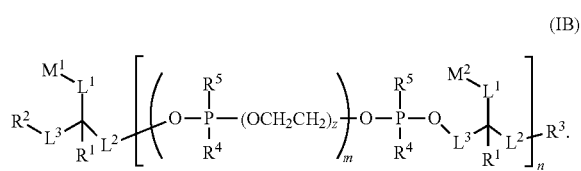

(IB)

wherein:

z is, at each occurrence, independently an integer from 1 to 100.

In a different embodiment, the compound has the following structure (IC):

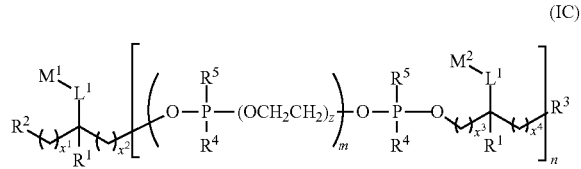

(IC)

wherein:

z is, at each occurrence, independently an integer from 1 to 100; and x¹, x², x³ and x⁴ are, at each occurrence, independently an integer from 0 to 6.

In certain related embodiments, z is an integer from 3 to 6 at one or more occurrences. In some specific embodiments, $x^1$ and $x^3$ are each 0 at each occurrence, and $x^2$ and $x^4$ are each 1 at each occurrence. In some embodiments, $x^1$, $x^2$ $x^3$ and $x^4$ are each 1 at each occurrence. In one particular embodiment, $L^4$ has the following structure:

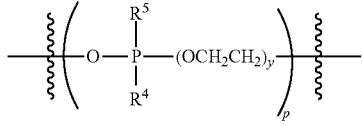

wherein:
p is, at each occurrence, independently an integer from 0 to 6; and
y is, at each occurrence, independently an integer from 1 to 100.

In some embodiments, $R^3$ comprises the following structure:

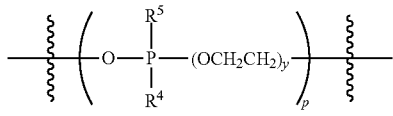

wherein:
p is, at each occurrence, independently an integer from 0 to 6; and
y is, at each occurrence, independently an integer from 1 to 100.

In certain embodiments, the compound has the following structure (ID):

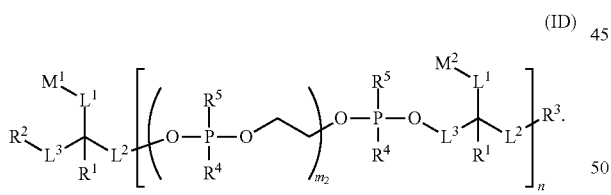

In some related embodiments, the compound has the following structure (IE):

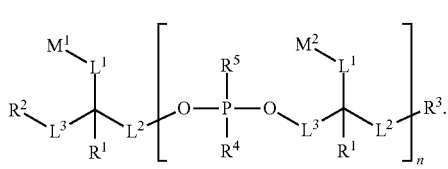

Another embodiment provides a compound having the following structure (II):

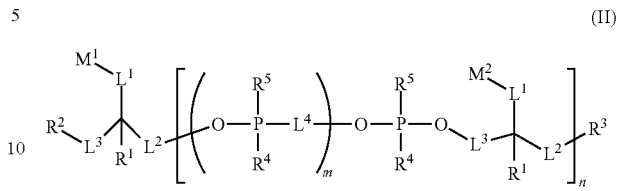

or a stereoisomer, salt or tautomer thereof, wherein:
$M^1$ and $M^2$ are, at each occurrence, independently a chromophore, provided that at least one occurrence of $M^1$ and $M^2$ combine to form a FRET acceptor-donor pair;
$L^1$ is at each occurrence, an optional linker;
$L^2$ and $L^3$ are, at each occurrence, independently an optional alkylene, alkenylene, alkynylene, heteroalkylene, heteroalkenylene, heteroalkynylene or heteroatomic linker;
$L^4$ is, at each occurrence, independently an alkylene or heteroalkylene linker;
$R^1$ is, at each occurrence, independently H, alkyl or alkoxy;
$R^2$ and $R^3$ are each independently H, OH, SH, alkyl, alkoxy, alkylether, heteroalkyl, —OP(=$R_a$)($R_b$)$R_c$, Q, or a protected form thereof, or L';
$R^4$ is, at each occurrence, independently OH, SH, O⁻, S⁻, $OR_d$ or $SR_d$;
$R^5$ is, at each occurrence, independently oxo, thioxo or absent;
$R_a$ is O or S;
$R_b$ is OH, SH, O⁻, S⁻, $OR_d$ or $SR_d$;
$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;
$R_d$ is a counter ion;
Q is, at each occurrence, independently a moiety comprising a reactive group, or protected form thereof, capable of forming a covalent bond with an analyte molecule, a targeting moiety, a solid support or a complementary reactive group Q';
L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (II);
m is, at each occurrence, independently an integer of zero to two or greater than 6; and
n is an integer of one or greater.

The various linkers and substituents (e.g., $M^1$, $M^2$, Q, $R^1$, $R^2$, $R^3$, $R^c$ $L^1$, $L^2$, $L^3$, and $L^4$) in the compound of structures (I) and (II) are optionally substituted with one more substituent. For example, in some embodiments the optional substituent is selected to optimize the water solubility or other property of the compounds of structures (I) or (II). In certain embodiments, each alkyl, alkoxy, alkylether, alkoxyalkylether, phosphoalkyl, thiophosphoalkyl, phosphoalkylether and thiophosphoalkylether in the compounds of structures (I) and (II) are optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether.

The optional linker $L^1$ can be used as a point of attachment of the $M^1$ and $M^2$ moieties to the remainder of the compound. For example, in some embodiments a synthetic precursor to the compound of structure (I) or structure (II) is prepared, and the $M^1$ and/or $M^2$ moiety is attached to the synthetic precursor using any number of facile methods known in the art, for example methods referred to as "click chemistry." For this purpose any reaction which is rapid and substantially irreversible can be used to attach $M^1$ or $M^2$ or both to the synthetic precursor to form a compound of structure (I) or structure (II). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. In some embodiments the reaction to form $L^1$ may be performed in an aqueous environment.

Accordingly, in some embodiments $L^1$ is at each occurrence a linker comprising a functional group capable of formation by reaction of two complementary reactive groups, for example a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group with a complementary reactive group.

In other embodiments, for at least one occurrence of the functional group can be formed by reaction of an alkyne and an azide.

In more embodiments, for at least one occurrence of $L^1$, the functional group comprises an alkene, ester, amide, thioester, disulfide, carbocyclic, heterocyclic or heteroaryl group. In some more specific embodiments, for at least one occurrence of $L^1$, $L^1$ is a linker comprising a triazolyl functional group.

In still other embodiments, for at least one occurrence of $L^1$, $L^1$-M has the following structure:

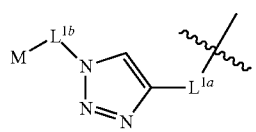

wherein $L^{1a}$ and $L^{1b}$ are each independently optional linkers.

In different embodiments, for at least one occurrence of $L^1$, $L^1$-M has the following structure:

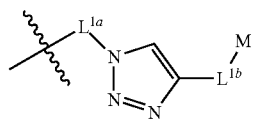

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

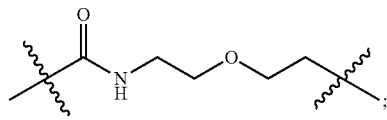

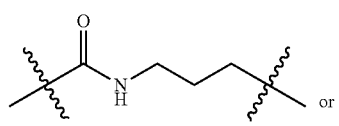

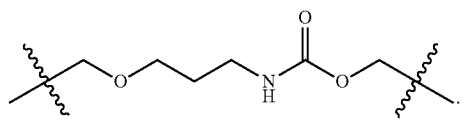

In still other different embodiments, $L^1$ is at each occurrence, independently an optional alkylene or heteroalkylene linker.

In more embodiments, $L^2$ and $L^3$ are, at each occurrence, independently $C_1$-$C_6$ alkylene, $C_2$-$C_6$ alkenylene or $C_2$-$C_6$ alkynylene.

In some embodiments, at least one occurrence of $L^1$ has one of the following structures:

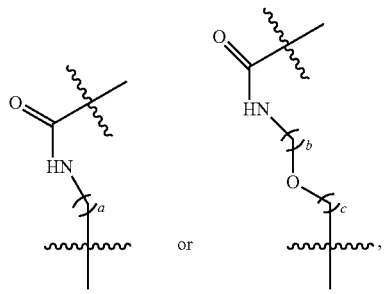

wherein
  a, b, and c are each independently an integer ranging from 1-6.

In some embodiments, each occurrence of $L^1$ has one of the following structures:

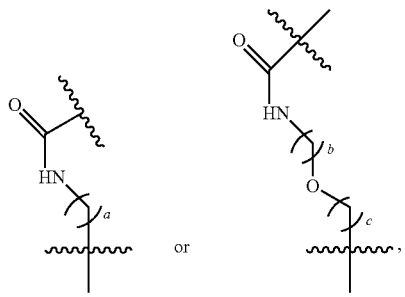

wherein
a, b, and c are each independently an integer ranging from 1-6.

In some embodiments, at least one occurrence of $L^1$ has one of the following structures:

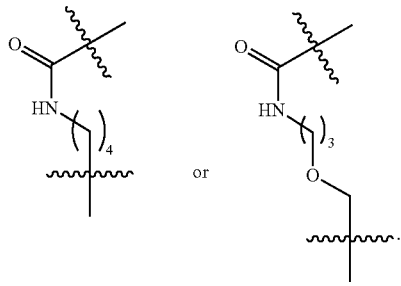

In some embodiments, each occurrence of $L^1$ has one of the following structures:

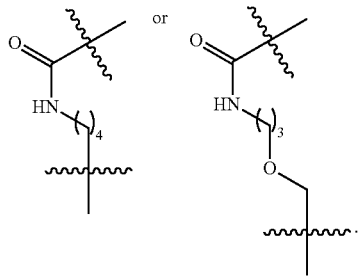

In still other embodiments, $R^4$ is, at each occurrence, independently OH, O⁻ or $OR_d$. It is understood that "$OR_d$" and "$SR_d$" are intended to refer to O⁻ and S⁻ associated with a cation. For example, the disodium salt of a phosphate group may be represented as:

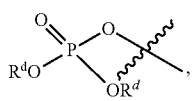

where $R_a$ is sodium (Na⁺).

In other embodiments, $R^5$ is, at each occurrence, oxo.

In some different embodiments of any of the foregoing compounds, $R^1$ is H.

In other various embodiments, $R^2$ and $R^3$ are each independently OH or $-OP(=R_a)(R_b)R_c$. In some different embodiments, $R^2$ or $R^3$ is OH or $-OP(=R_a)(R_b)R_c$, and the other of $R^2$ or $R^3$ is Q or a linker comprising a covalent bond to Q. In some embodiments, $R^2$ and $R^3$ are each independently $-OP(=R_a)(R_b)R_c$. In some specific embodiments, $R_c$ is OL'. In some of those embodiments, L' is a heteroalkylene linker to: Q, a targeting moiety, an analyte molecule, a solid support, a solid support residue, a nucleoside or a further compound of structure (I) or a further compound of structure (II). In some embodiments, L' comprises an alkylene oxide or phosphodiester moiety, or combinations thereof. In certain embodiments, L' has the following structure:

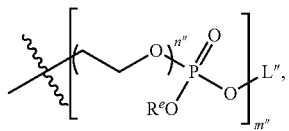

wherein:
m" and n" are independently an integer from 1 to 10;
$R^c$ is H, an electron pair or a counter ion;
L" is $R^c$ or a direct bond or linkage to: Q, a targeting moiety, an analyte molecule, a solid support, a solid support residue, a nucleoside or a further compound of structure (I) or a further compound of structure (II).

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) or structure (II) (e.g., in the $R^2$ or $R^3$ position), and Q and Q' comprise complementary reactive groups such that reaction of the compound of structure (I) or structure (II) and the further compound of structure (I) or structure (II) results in covalently bound dimer of the compound of structure (I) or structure (II). Multimer compounds of structure (I) or structure (II) can also be prepared in an analogous manner and are included within the scope of embodiments of the invention.

The type of Q group and connectivity of the Q group to the remainder of the compound of structure (I) or structure (II) is not particularly limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) and/or structure (II) comprise Q groups commonly employed in the field of bio-conjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide. In some embodiments, Q comprises a maleimide functional group.

Exemplary Q moieties are provided in Table I below.

TABLE 1

| Exemplary Q Moieties | |
|---|---|
| Structure | Class |
| —SH | Sulfhydryl |
| —N=C=S | Isothiocyanate |
| [structure with OMe and NH₂⁺Cl⁻] | Imidoester |
| [acyl azide structure] | Acyl Azide |
| [tetrafluorophenyl ester] | Activated Ester |
| [pentafluorophenyl ester] | Activated Ester |
| [sulfo-nitrophenyl ester] | Activated Ester |
| [sulfo-SMCC type structure] | Activated Ester |
| [NHS ester structure] | Activated Ester |

TABLE 1-continued

| Exemplary Q Moieties | |
|---|---|
| Structure | Class |
| [sulfo-NHS ester] | Activated Ester |
| —S(O)₂—X  X = halo | Sulfonyl halide |
| [maleimide structure] | Maleimide |
| [SMCC maleimide structure] | Maleimide |
| [N-CO-CH₂-X structure]  X = halo | α-haloimide |
| [pyridyl disulfide] | Disulfide |
| [phosphine structure with PPh₂] | Phosphine |
| —N₃ | Azide |
| —C≡CH | Alkyne |

TABLE 1-continued

Exemplary Q Moieties

| Structure | Class |
|---|---|
| 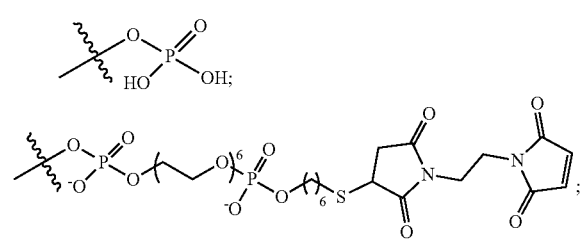 | Biotin |
| 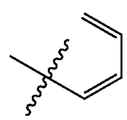 [SMILES: */C=C\C=C] | Diene |
| | Alkene/dienophile |
| | Alkene/dienophile |
| EWG = electron withdrawing group | |
| —NH$_2$ | Amino |

It should be noted that in some embodiments, wherein Q is SH, the SH moiety will tend to form disulfide bonds with another suithydryl group on another compound of structure (I) or structure (II). Accordingly, some embodiments include compounds of structure (I), which are in the form of disulfide dimers, the disulfide bond being derived from SH Q groups. Other embodiments include compounds of structure (II), which are in the form of disulfide dimers, the disulfide bond being derived from SH Q groups.

In some other embodiments, one of $R^2$ or $R^3$ is OH or —OP(=$R_a$)($R_b$)$R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or non-polymeric bead. In some embodiments, the targeting moiety is an antibody or cell surface receptor antagonist.

In certain specific embodiments, $R^2$ or $R^3$ has one of the following structures:

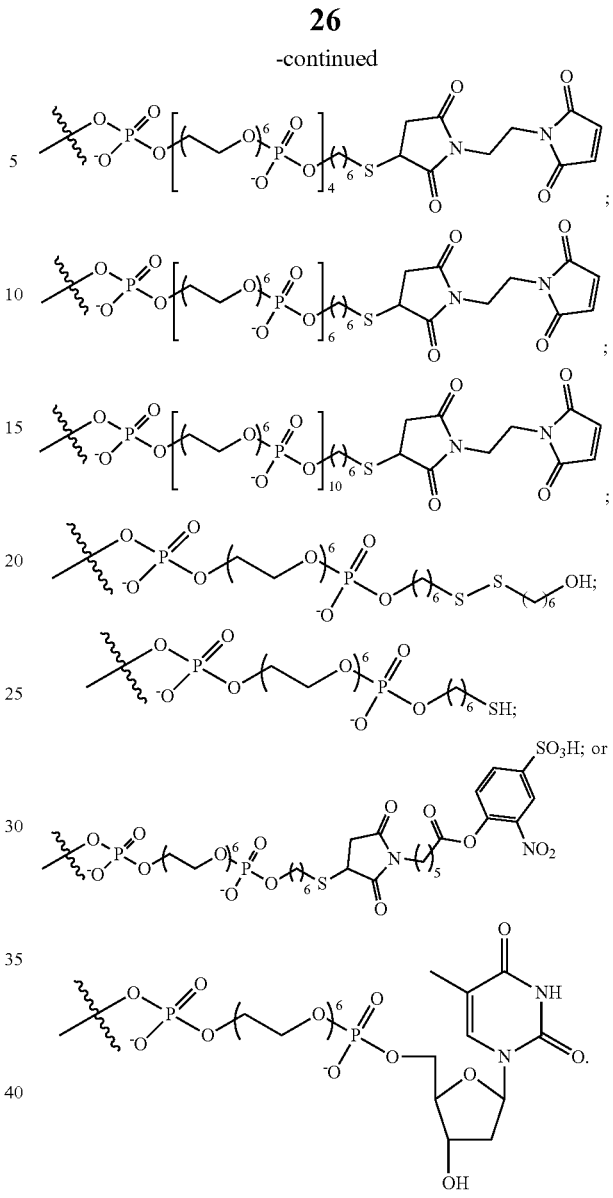

The value for m is another variable that can be selected based on the desired distance between chromophores, fluorescence and/or color intensity. In some embodiments, m is, at each occurrence, independently an integer from 1 to 10. In other embodiments, m is, at each occurrence, independently an integer from 1 to 5, for example 1, 2, 3, 4 or 5.

The fluorescence intensity can also be tuned by selection of different values of n. In certain embodiments, n is an integer from 1 to 100. In other embodiments, n is an integer from 1 to 10.

$M^1$ and $M^2$ are selected based on the desired optical properties, for example based on a desired Stoke's shift, absorbance/emission overlap, a particular color and/or fluorescence emission wavelength. In some embodiments, $M^1$ (or alternatively $M^2$) is the same at each occurrence; however, it is important to note that each occurrence of $M^1$ or $M^2$ need not be an identical $M^1$ or $M^2$, respectively. Certain embodiments include compounds wherein $M^1$ is not the same at each occurrence. Some embodiments include compounds wherein $M^2$ is not the same at each occurrence.

In some embodiments $M^1$ and $M^2$ are selected to have absorbance and/or emission characteristics for use in FRET methods. For example, in such embodiments the different $M^1$ and $M^2$ moieties are selected such that $M^1$ has an absorbance of radiation at one wavelength that induces an emission of radiation by $M^2$ at a different wavelength by a FRET mechanism. Exemplary $M^1$ and $M^2$ moieties can be appropriately selected by one of ordinary skill in the art based on the desired end use.

Each respective $M^1$ and $M^2$ may be attached to the remainder of the molecule from any position (i.e., atom) on $M^1$ or $M^2$. One of skill in the art will recognize means for attaching $M^1$ or $M^2$ to the remainder of molecule. Exemplary methods include the "click" reactions described herein.

In some embodiments, $M^1$ or $M^2$ are FRET, fluorescent or colored moieties. Any fluorescent and/or colored moiety may be used to form a FRET donor-acceptor pair, for examples those known in the art and typically employed in colorimetric, UV, and/or fluorescent assays may be used. In some embodiments, $M^1$ or $M^2$, or both are, at each occurrence, independently fluorescent or colored. Examples of $M^1$ or $M^2$ moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, $M^1$ or $M^2$, or both, at each occurrence, independently comprise three or more aryl or heteroaryl rings, or combinations thereof, for example four or more aryl or heteroaryl rings, or combinations thereof, or even five or more aryl or heteroaryl rings, or combinations thereof. In some embodiments, $M^1$ or $M^2$, or both, at each occurrence, independently comprise six aryl or heteroaryl rings, or combinations thereof. In further embodiments, the rings are fused. For example in some embodiments, $M^1$ or $M^2$ or both, at each occurrence, independently comprise three or more fused rings, four or more fused rings, five or more fused rings, or even six or more fused rings.

In some embodiments, $M^1$ or $M^2$ or both, are cyclic. For example, in some embodiments $M^1$ or $M^2$ or both, are carbocyclic. In other embodiment, $M^1$ or $M^2$ or both are heterocyclic. In still other embodiments of the foregoing, $M^1$ or $M^2$ or both, at each occurrence, independently comprise an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), (II), (IA), (IB), (IC), (ID), or (IE) $M^1$ or $M^2$ or both, at each occurrence, independently comprise at least one heteroatom. For example, in some embodiments, the heteroatom is nitrogen, oxygen or sulfur.

In still more embodiments of any of the foregoing, $M^1$ or $M^2$ or both, at each occurrence, independently comprise at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, $M^1$ or $M^2$ or both are, at each occurrence, independently a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, $M^1$ or $M^2$ or both are, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, $M^1$ or $M^2$ or both are, at each occurrence, independently a coumarin dye, resonifin dye, dipyrrometheneboron difluoride dye, ruthenium bipyridyl dye, energy transfer dye, thiazole orange dye, polymethine or N-aryl-1,8-naphthalimide dye. In certain embodiments, Wand $M^2$ are, at each occurrence, independently boron-dipyrromethene, rhodamine, cyanine, pyrene, perylene, perylene monoimide or 6-FAM or a derivative thereof.

In still more embodiments of any of the foregoing, $M^1$ at each occurrence is the same. In other embodiments, each $M^1$ is different. In still more embodiments, one or more $M^1$ is the same and one or more $M^1$ is different.

In still more embodiments of any of the foregoing, $M^2$ at each occurrence is the same. In other embodiments, each $M^2$ is different. In still more embodiments, one or more $M^2$ is the same and one or more $M^2$ is different.

In some embodiments, $M^1$ or $M^2$ or both are, at each occurrence, independently boron-dipyrromethene, rhodamine, cyanine, pyrene, perylene, perylene monoimide or 6-FAM or a derivative thereof. In some other embodiments, $M^1$ and $M^2$ at each occurrence, independently have one of the following structures:

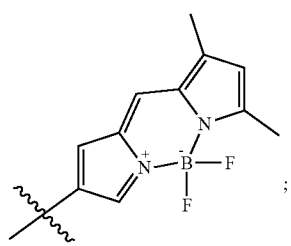

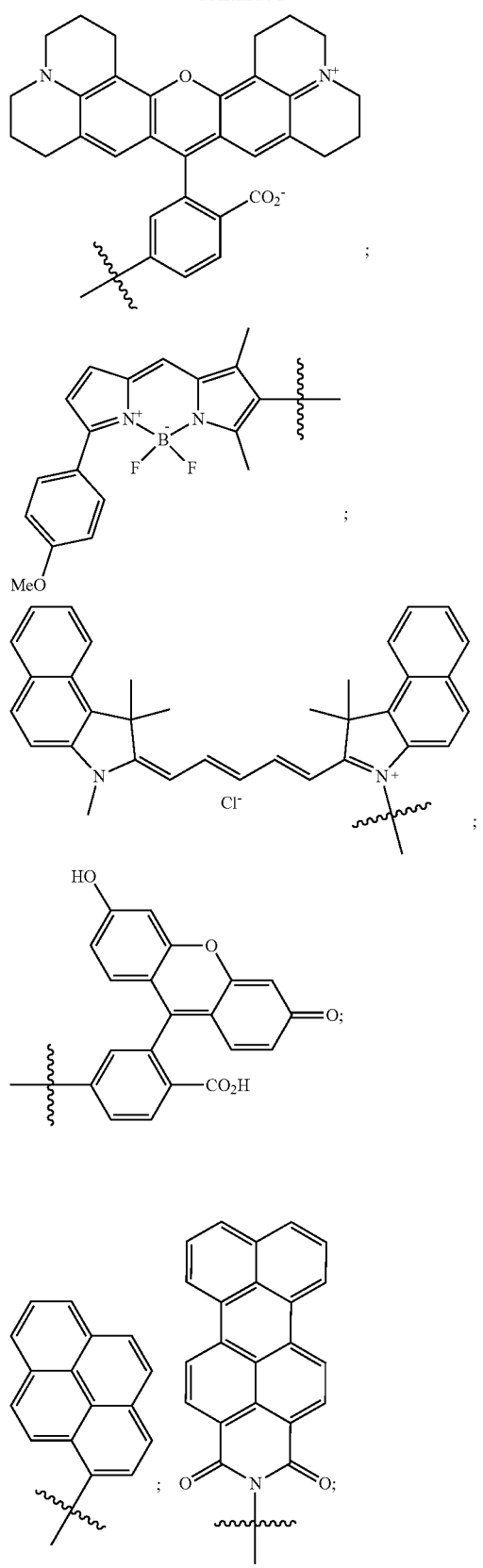
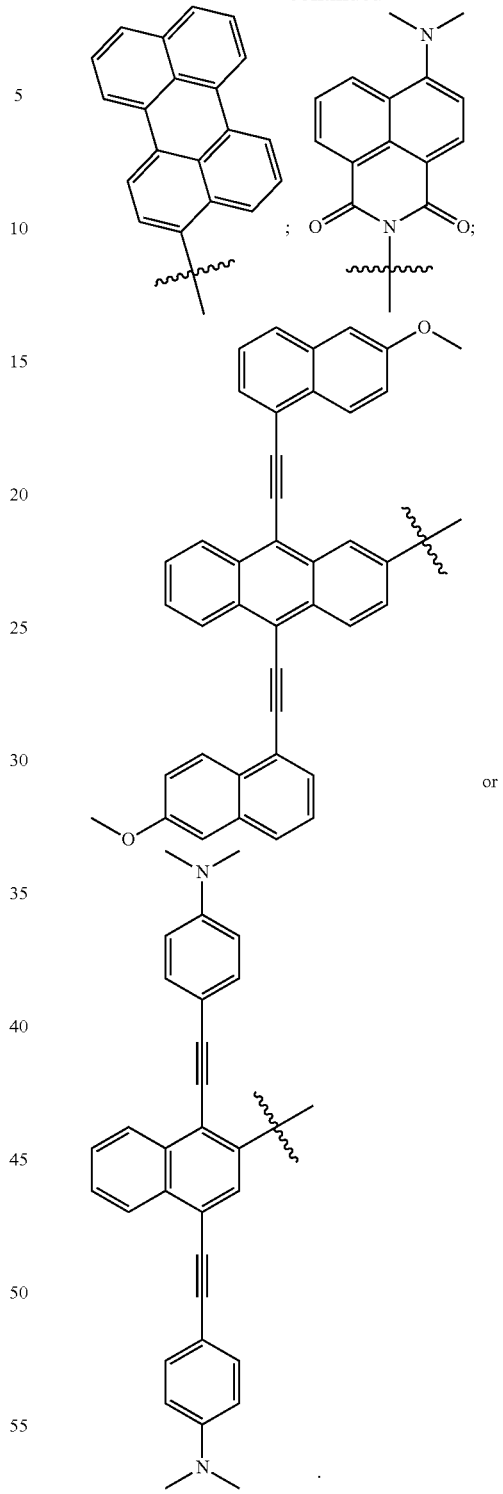
In some specific embodiments, the compound is a compound selected from Table 2. In other specific embodiments, the compound is a compound selected from Table 3. The compounds in Tables 2 and 3 were prepared according to the procedures set forth in the Examples and their identity confirmed by mass spectrometry.

TABLE 2
Exemplary Compounds of Structure 1
| Nos. | MW. Found Calc. | Structure |
|---|---|---|
| I-1 | 2049.9 / 2049.3 | 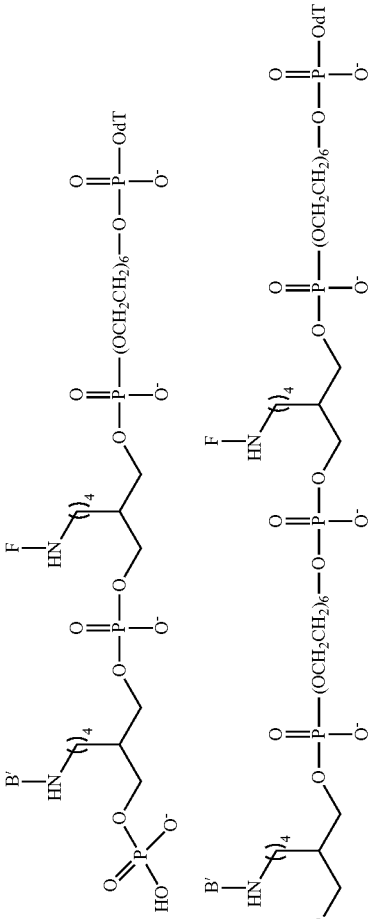 |
| I-2 | 2394.1 / 2393.6 | 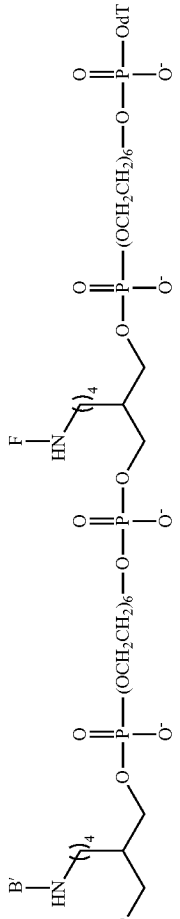 |
| I-3 | 2738.3 / 2737.9 | 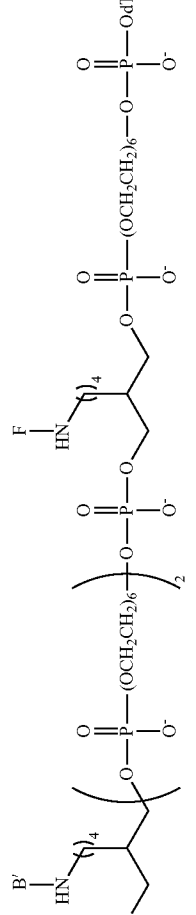 |
| I-4 | 3082.4 / 3084.0 | 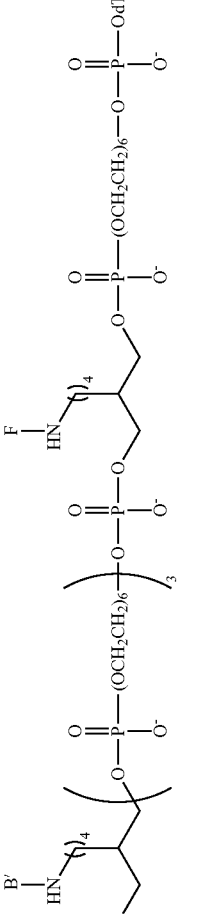 |
| I-5 | 2258.3 / 2260.2 | 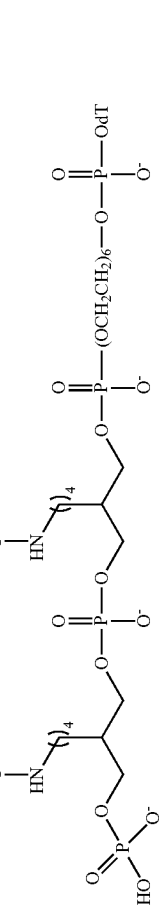 |

TABLE 2-continued
Exemplary Compounds of Structure 1
| Nos. | MW. Found Calc. | Structure |
|---|---|---|
| I-6 | 2602.7 / 2604.5 | 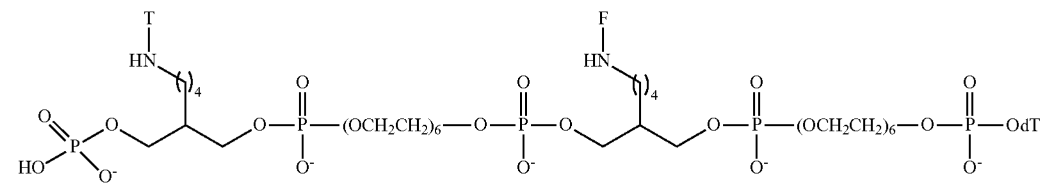 |
| I-7 | 2947.3 / 2948.8 | 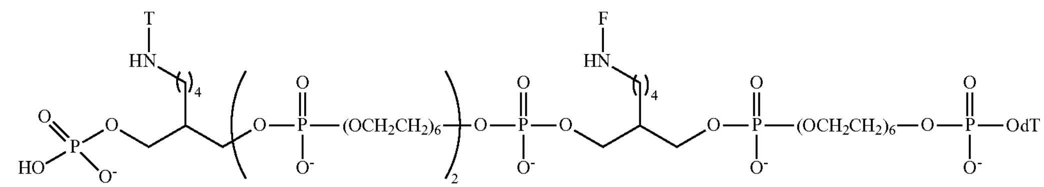 |
| I-8 | 3291.7 / 3293.1 | 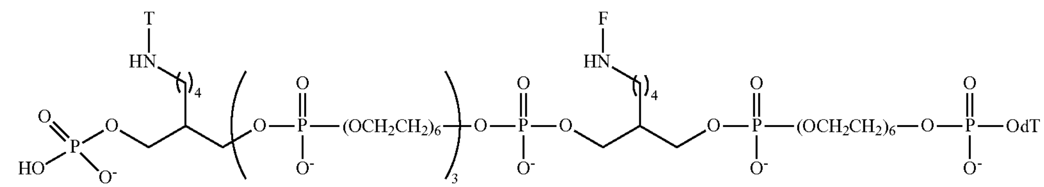 |
| I-9 | 5578.9 / 5578.5 | 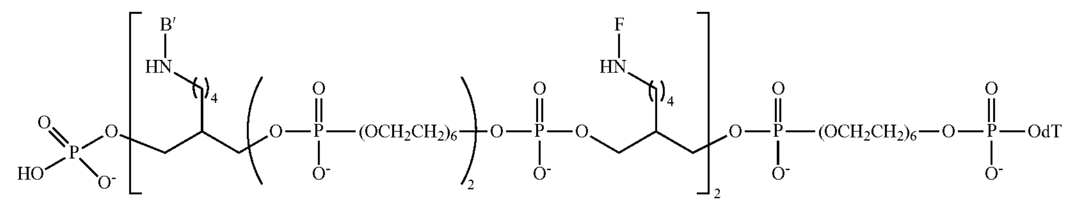 |
| I-10 | 8420.7 / 8418.9 | 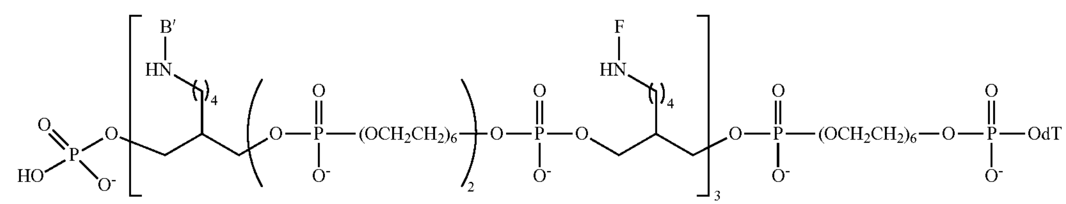 |
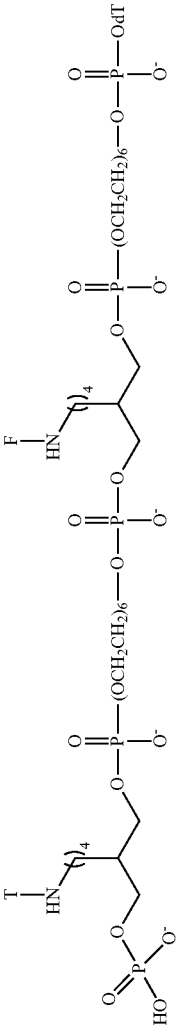

TABLE 2-continued

Exemplary Compounds of Structure 1

| Nos. | MW. Found Calc. | Structure |
|---|---|---|
| I-11 | 11260.4 11259.2 | 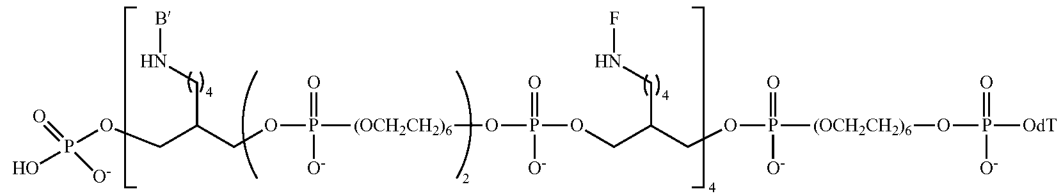 |
| I-12 | 14102.4 14009.5 | 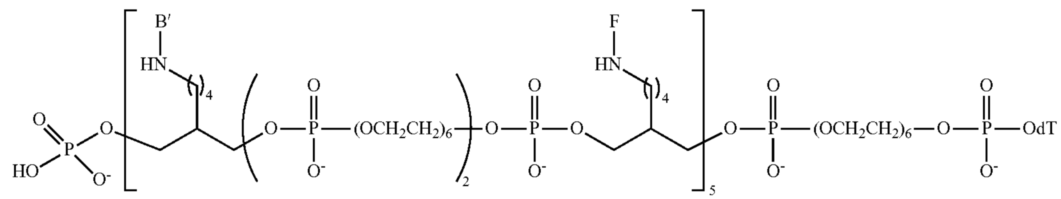 |
| I-13 | 3634.2 3633.8 | 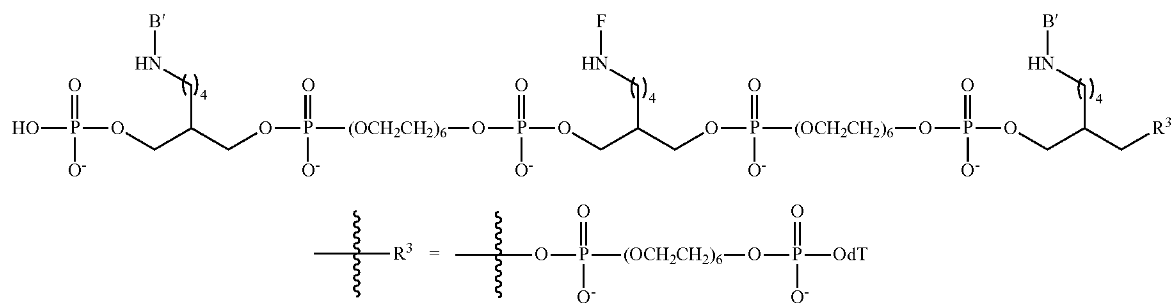 |
| I-14 | 4322.7 4322.4 | 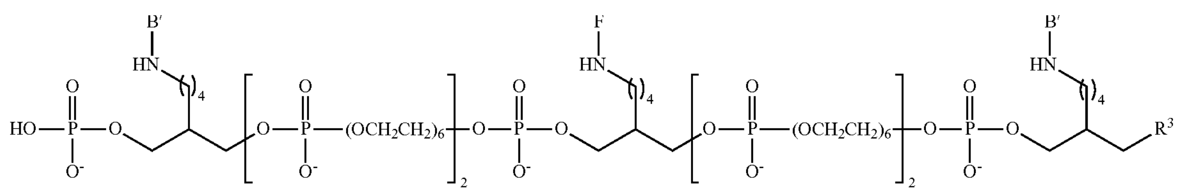 |

TABLE 2-continued

Exemplary Compounds of Structure 1

| Nos. | MW. Found Calc. | Structure |
|---|---|---|
| I-15 | 3882.3 3881.9 | |
| I-16 | 3369.6 3369.5 | |

TABLE 2-continued
Exemplary Compounds of Structure 1
| Nos. | MW. Found Calc. | Structure |
|---|---|---|
| I-17 | 3794.2 3793.8 | 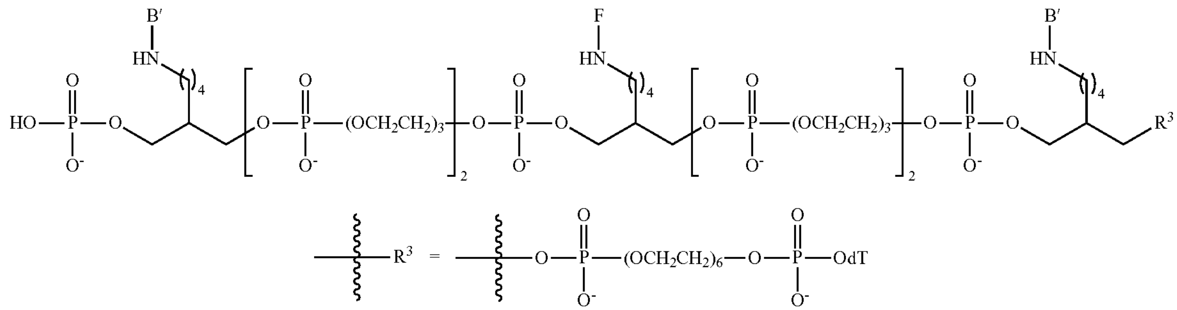 |
| I-18 | 3305.9 3305.5 | 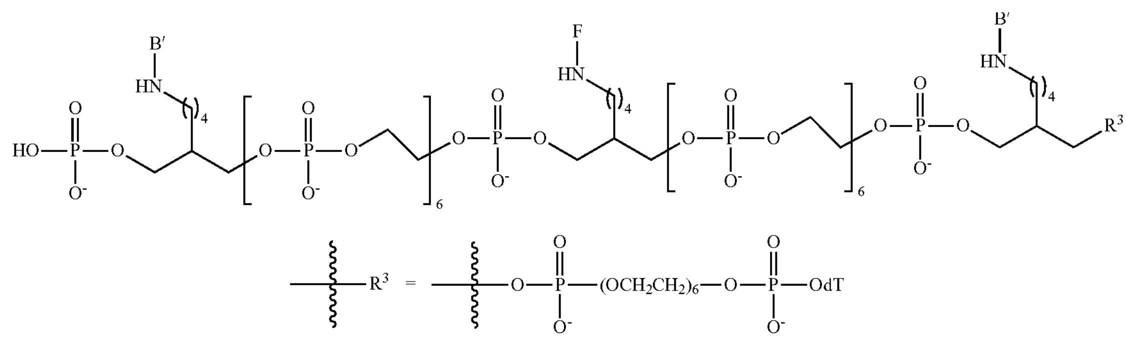 |
| I-19 | 3666.4 3665.8 | 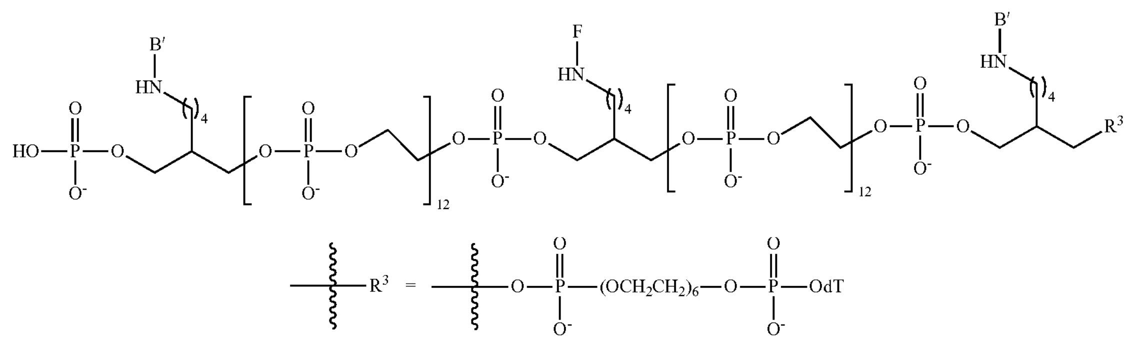 |
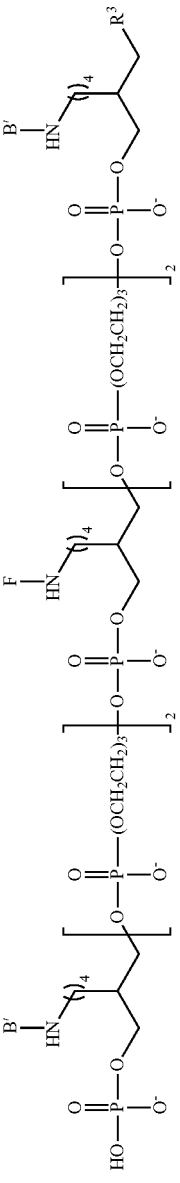

TABLE 2-continued

Exemplary Compounds of Structure 1

| Nos. | MW. Found Calc. | Structure |
|---|---|---|
| I-20 | 4891.3 / 4889.9 | 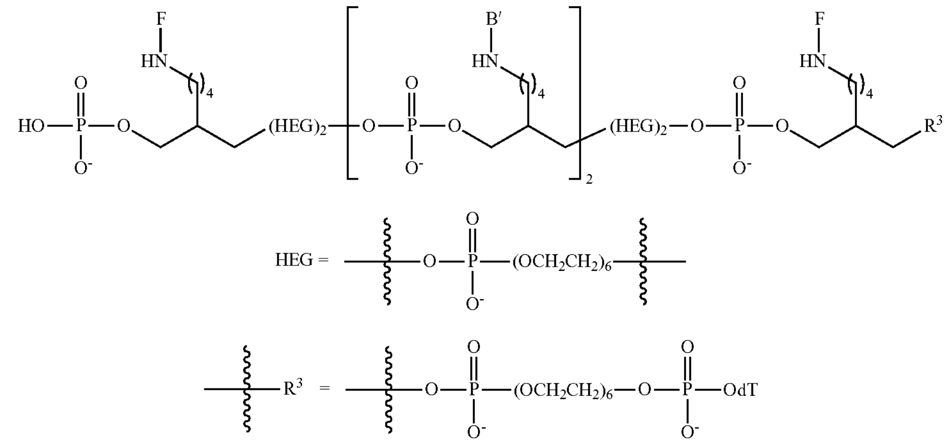 |
| I-21 | 5235.2 / 5234.2 | 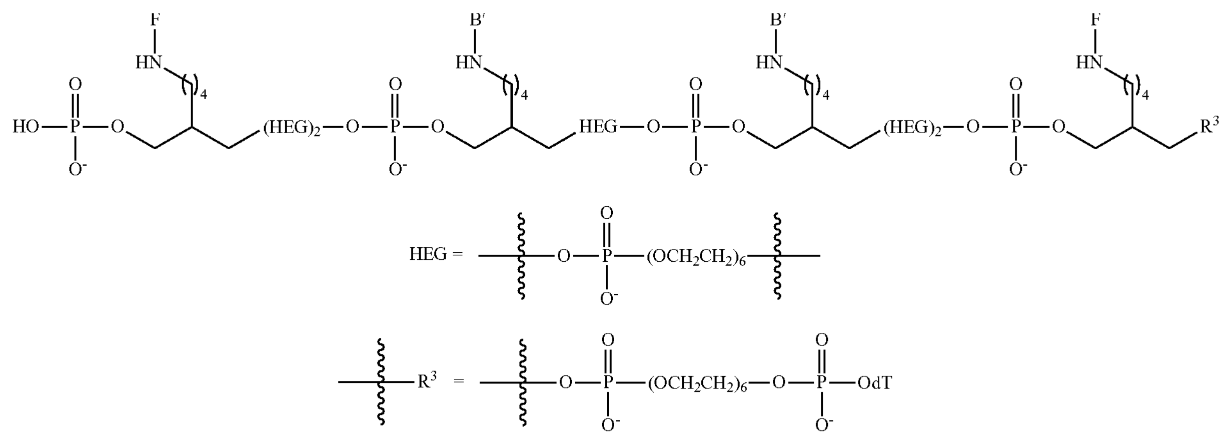 |

TABLE 2-continued
Exemplary Compounds of Structure 1
| Nos. | MW. Found Calc. | Structure |
|---|---|---|
| I-22 | 5580.3 5578.5 | 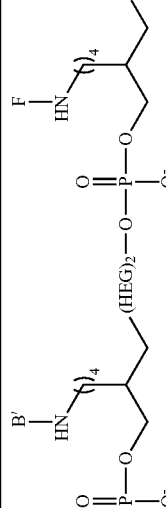 |
| I-23 | 5924.9 5922.8 | 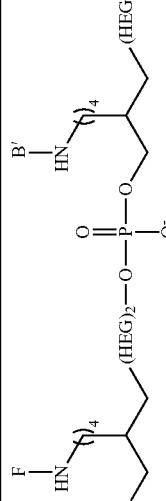 |

TABLE 2-continued
Exemplary Compounds of Structure 1
| Nos. | MW. Found Calc. | Structure |
|---|---|---|
| I-24 | 4909.5 / 4911.1 | 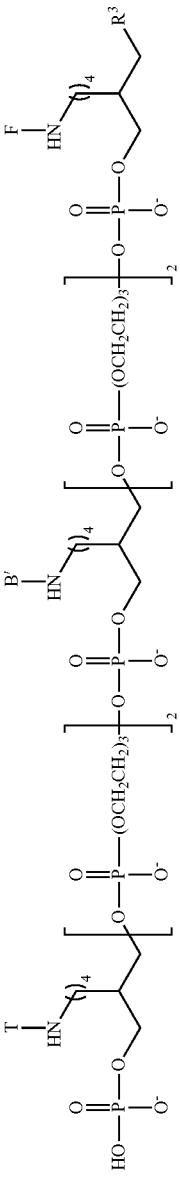 |
| I-25 | 1858.2 / 1858.5 | 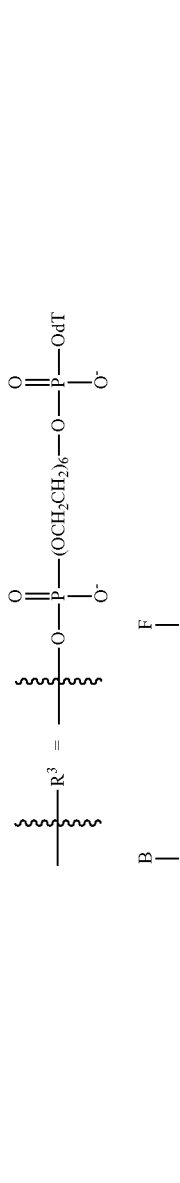 |
| I-26 | 2202.8 / 2202.8 | 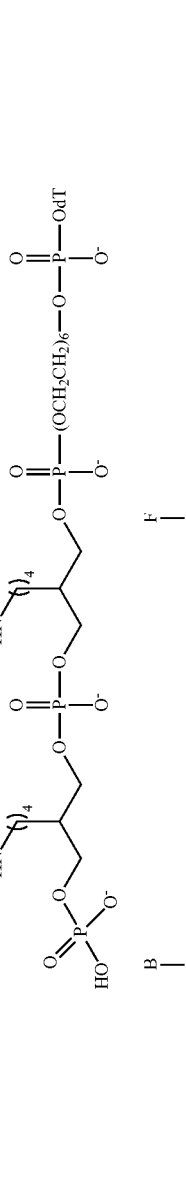 |
| I-27 | 2546.7 / 2547.1 | 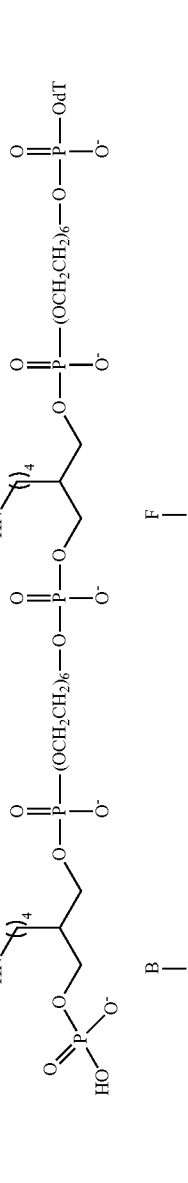 |

TABLE 2-continued

Exemplary Compounds of Structure 1

| Nos. | MW. Found Calc. | Structure |
|---|---|---|
| I-28 | 2891.8 / 2891.4 | 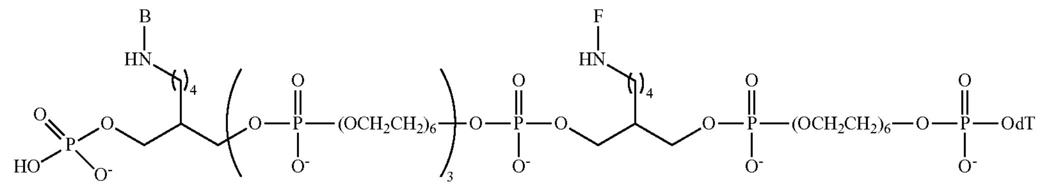 |
| I-29 | 2173.8 / 2173.4 | 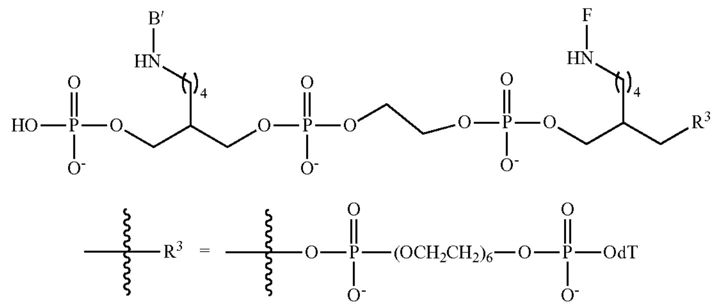 |
| I-30 | 2297.7 / 2297.4 | 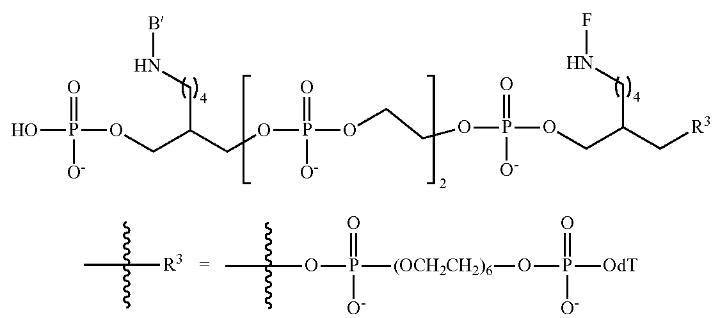 |
| I-31 | 2421.6 / 2421.5 | 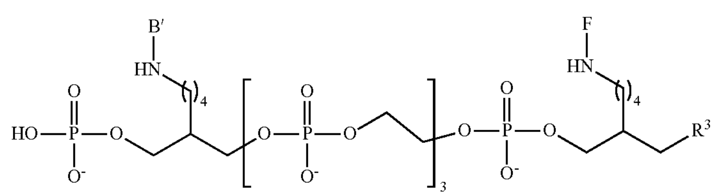 |

TABLE 2-continued
Exemplary Compounds of Structure 1
| Nos. | MW. Found Calc. | Structure |
|---|---|---|
| I-32 | 2546.0 / 2545.5 | 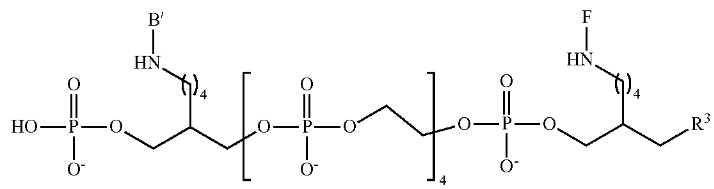 |
| I-33 | 3994.9 / 3994.0 | 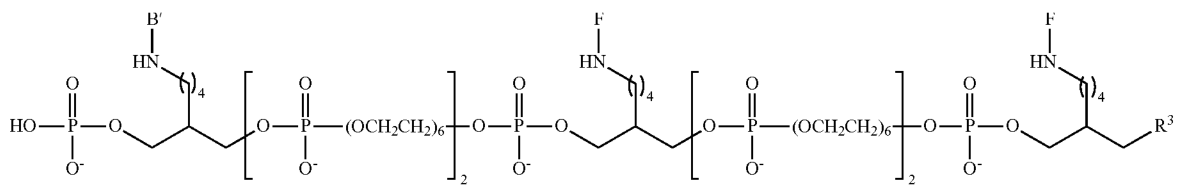 |
| I-34 | 5251.3 / 5250.1 | 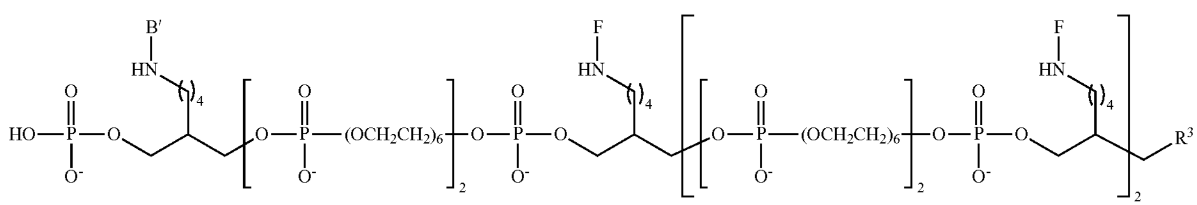 |
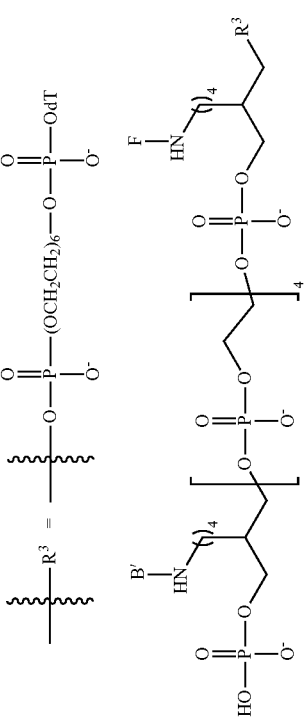

TABLE 2-continued

Exemplary Compounds of Structure 1

| Nos. | MW. Found Calc. | Structure |
|---|---|---|
| I-35 | 6508.2 / 6506.2 | 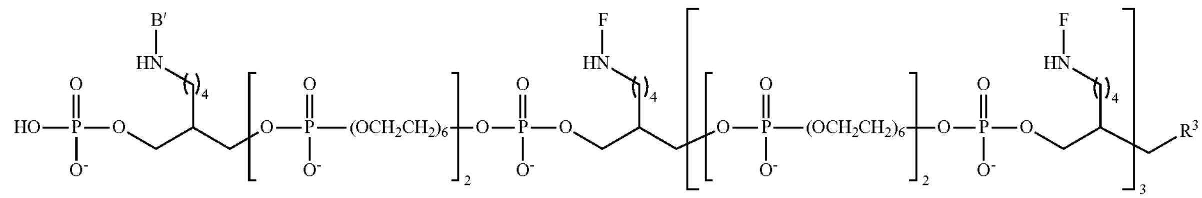 |
| I-36 | 7764.2 / 7762.3 | 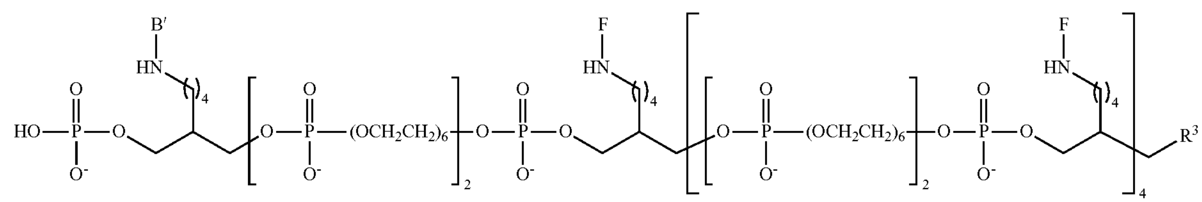 |
| I-37 | 2489.3 / 2489.0 | 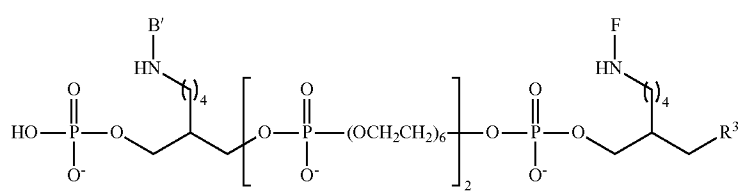 |

TABLE 2-continued

Exemplary Compounds of Structure 1

| Nos. | MW. Found Calc. | Structure |
|---|---|---|
| I-38 | 3745.3 / 3745.1 | 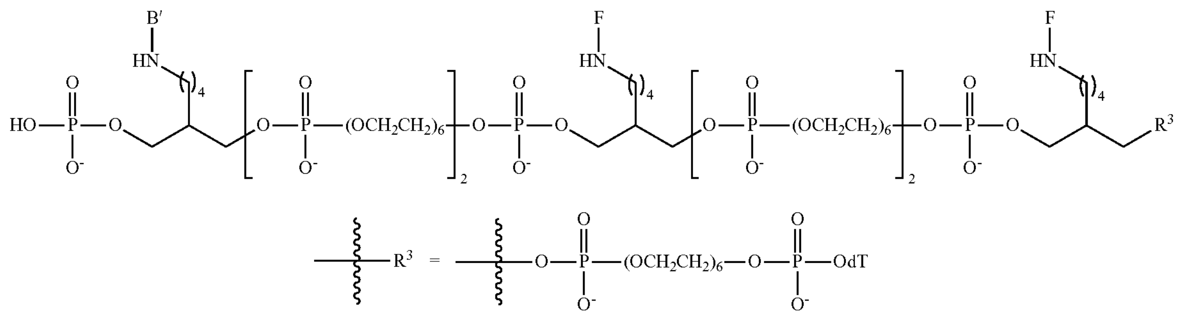 |
| I-39 | 5002.3 / 5001.2 | 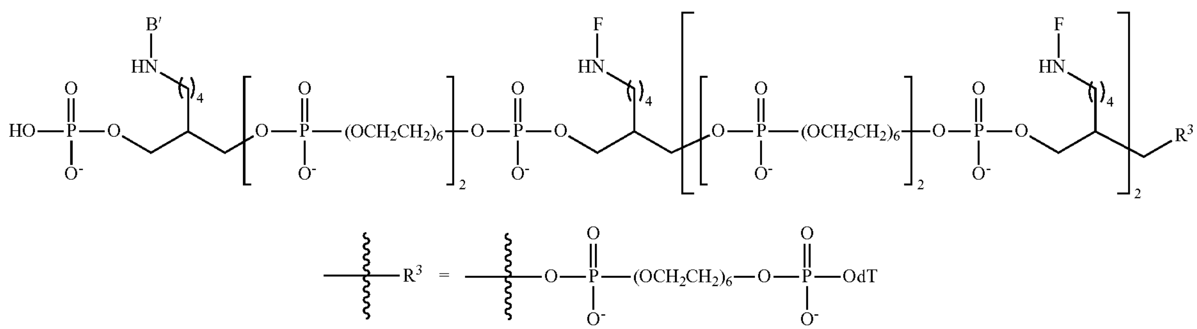 |
| I-40 | 6257.8 / 6257.3 | 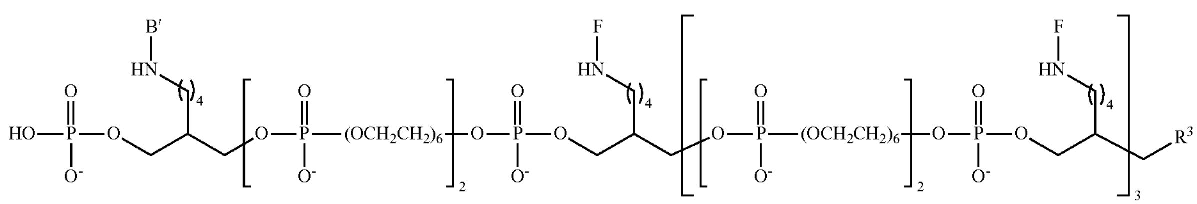 |

TABLE 2-continued
Exemplary Compounds of Structure 1
| Nos. | MW. Found Calc. | Structure |
|---|---|---|
| I-41 | 6048.1 6046.9 | 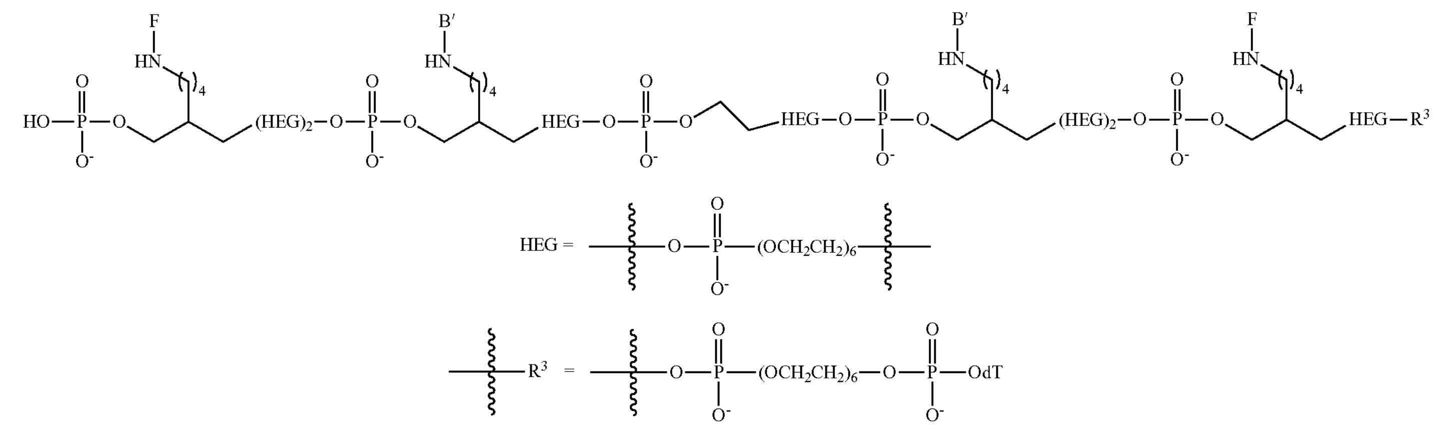 |
| I-42 | 5827.6 5826.6 | 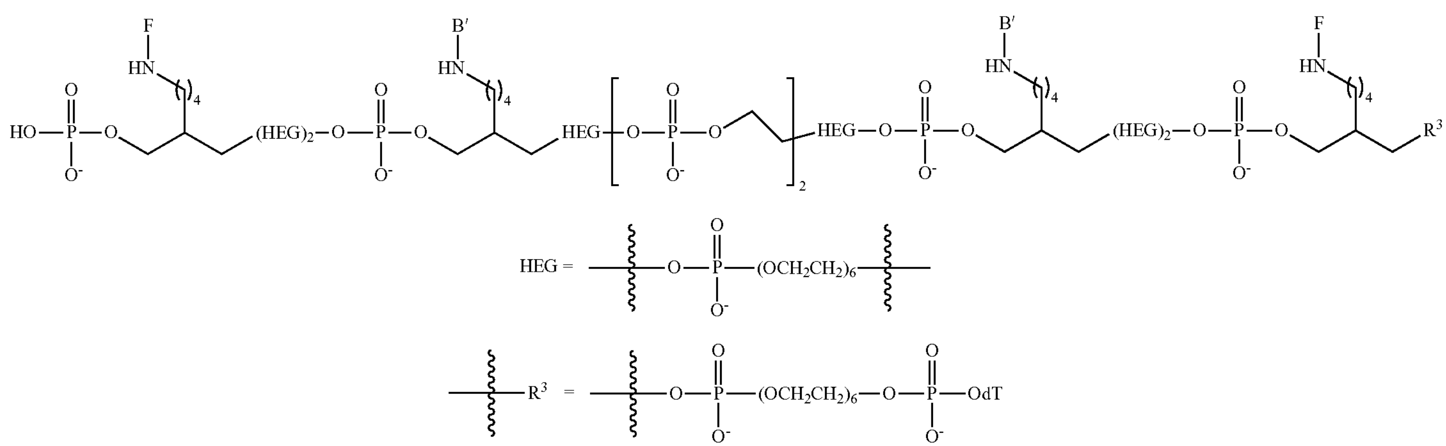 |
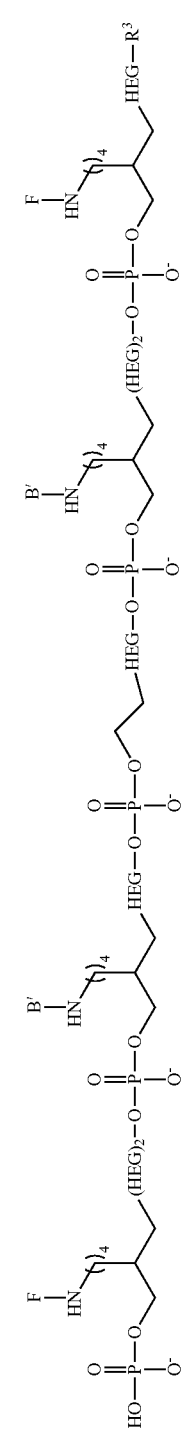

TABLE 2-continued

Exemplary Compounds of Structure 1

| Nos. | MW. Found Calc. | Structure |
|---|---|---|
| I-43 | 5952.2 / 5950.7 | 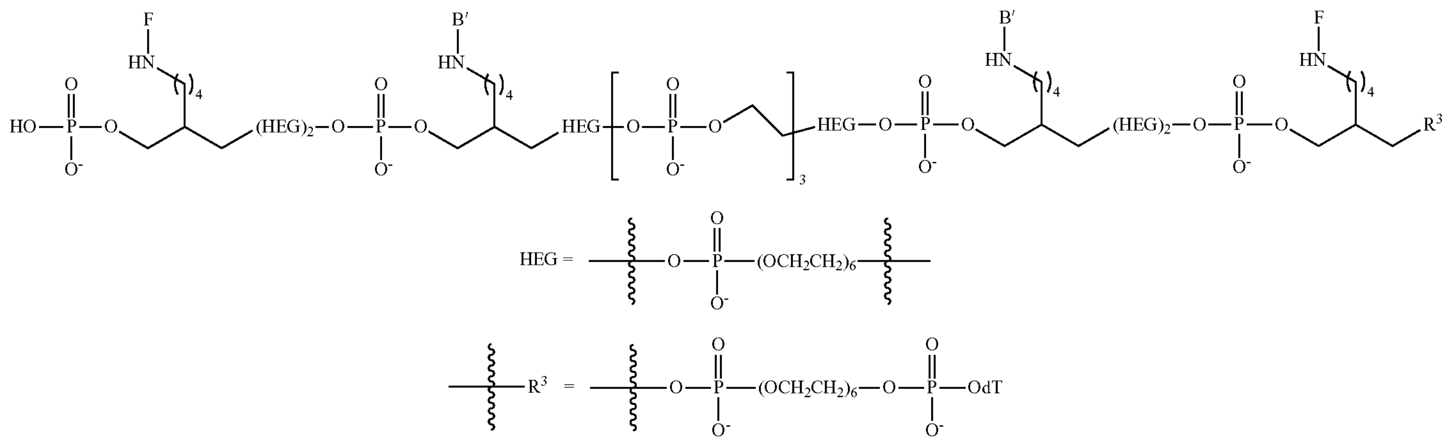 |
| I-44 | 6075.4 / 6074.7 | 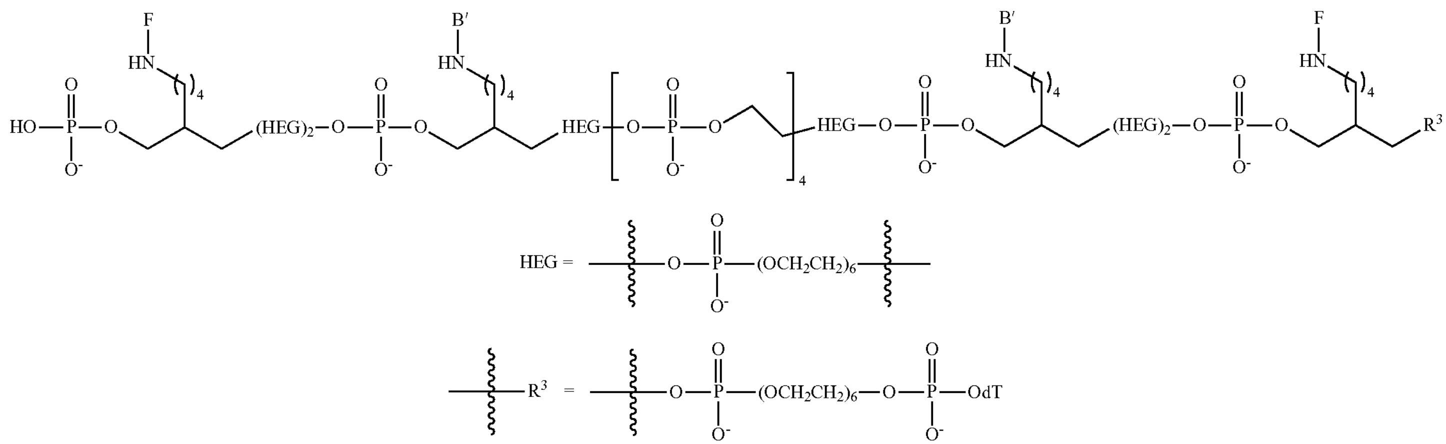 |

TABLE 2-continued

Exemplary Compounds of Structure 1

| Nos. | MW. Found Calc. | Structure |
|---|---|---|
| I-45 | 2809.4 / 2812.7 | 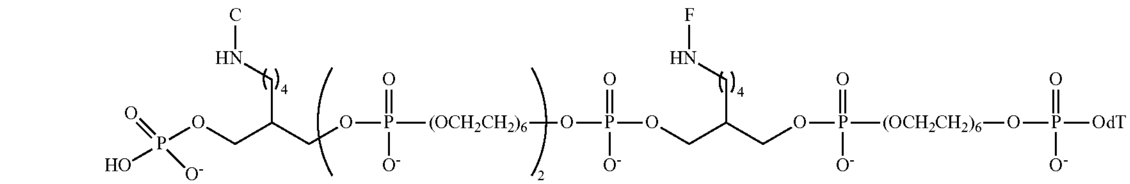 |
| I-46 | 4465.5 / 4471.4 | 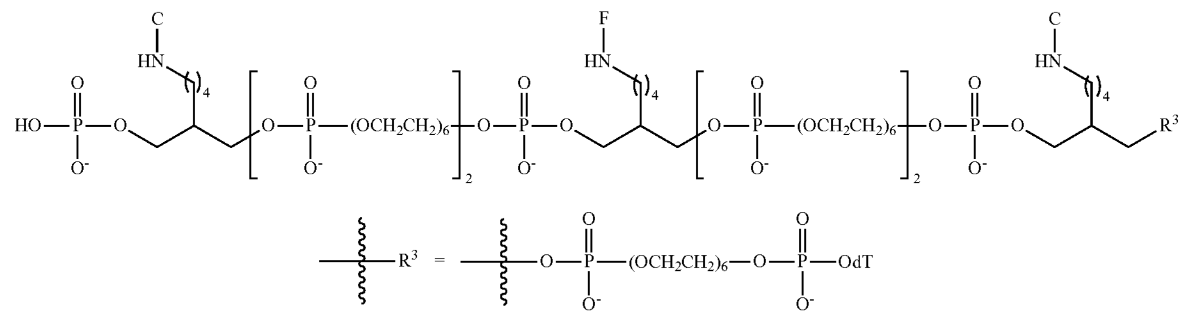 |
| I-47 | — / 6130.2 | 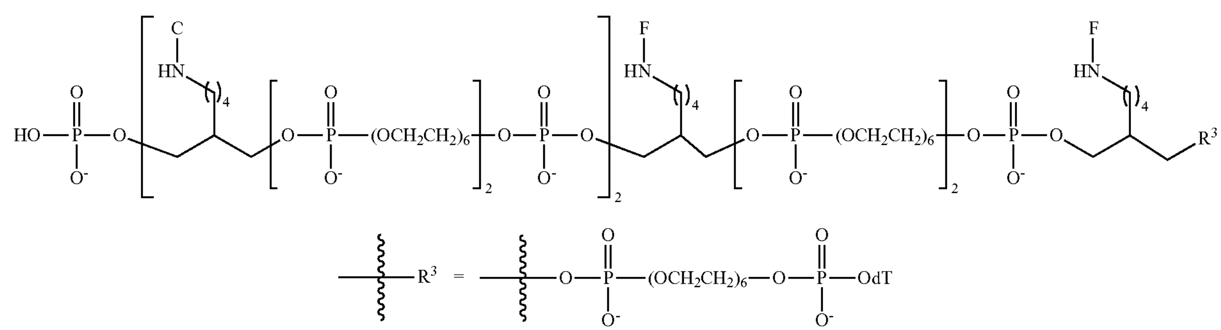 |

TABLE 2-continued

Exemplary Compounds of Structure 1

| Nos. | MW. Found Calc. | Structure |
|---|---|---|
| I-48 | — / 7788.9 | |
| I-49 | 937.4 / 937.8 | 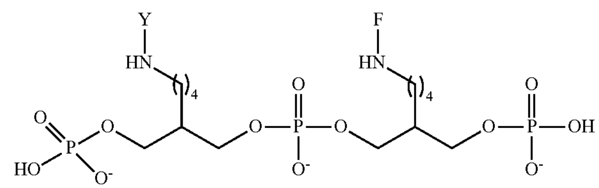 |
| I-50 | 1289.7 / 1290.2 | 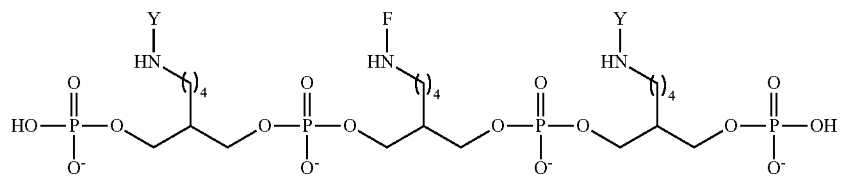 |
| I-51 | 987.3 / 987.9 | 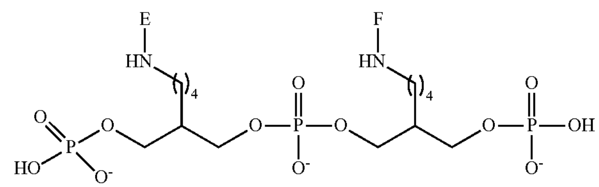 |

TABLE 2-continued

Exemplary Compounds of Structure 1

| Nos. | MW. Found Calc. | Structure |
|---|---|---|
| I-52 | 1389.8 / 1390.3 | 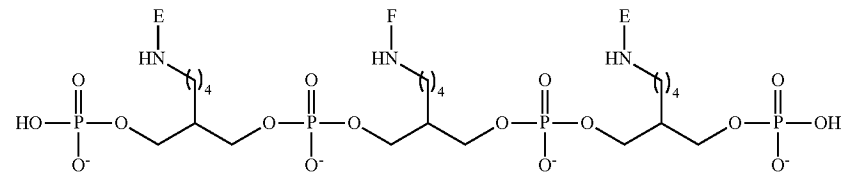 |
| I-53 | 2359.6 / 2360.2 | 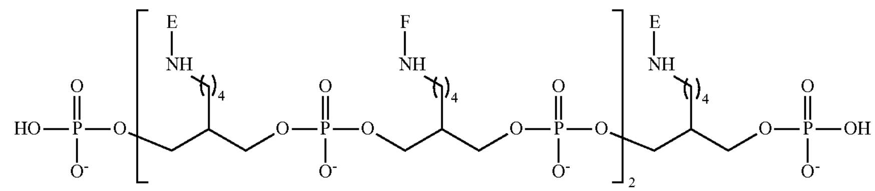 |
| I-54 | 3329.7 / 3330.1 | 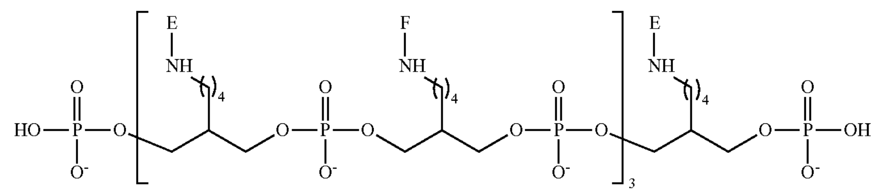 |
| I-55 | 4300.8 / 4300.0 | 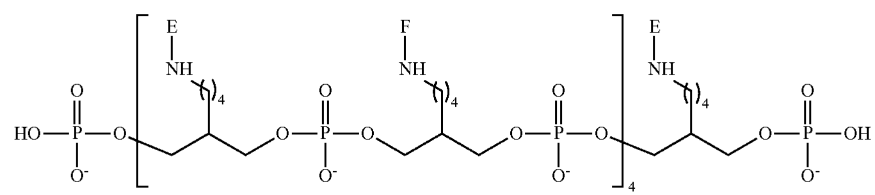 |
| I-56 | 2209.6 / 2210.0 | 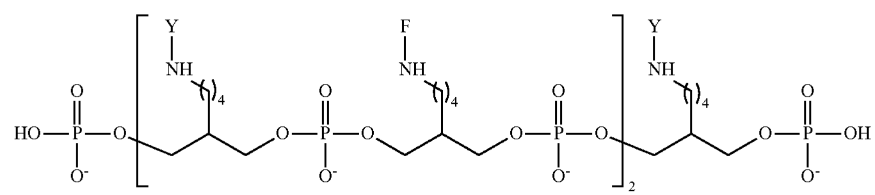 |

TABLE 2-continued

Exemplary Compounds of Structure 1

| Nos. | MW. Found Calc. | Structure |
|---|---|---|
| I-57 | 3129.3 / 3129.9 | 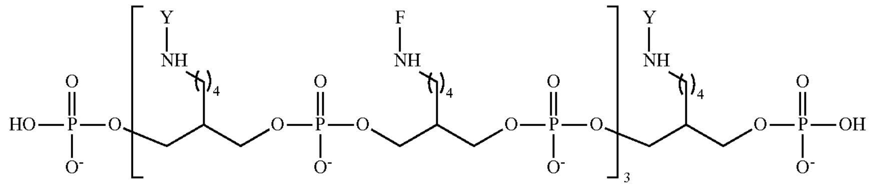 |
| I-58 | 4049.2 / 4049.7 | 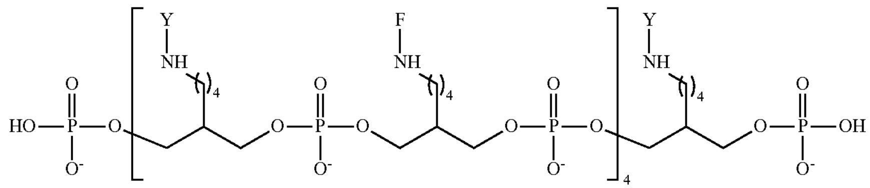 |
| I-59 | 4969.2 / 4969.5 | 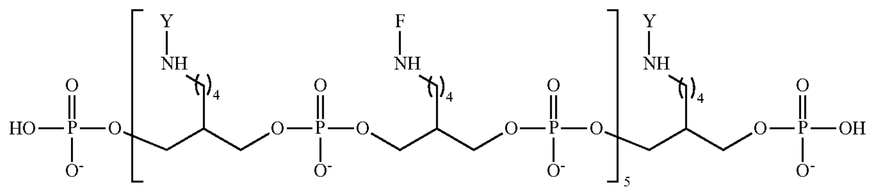 |

TABLE 3

Exemplary Compounds of Structure II

| Nos. | MW. Found Calc. | Structure |
|---|---|---|
| II-1 | 1538.6 / 1538.3 | 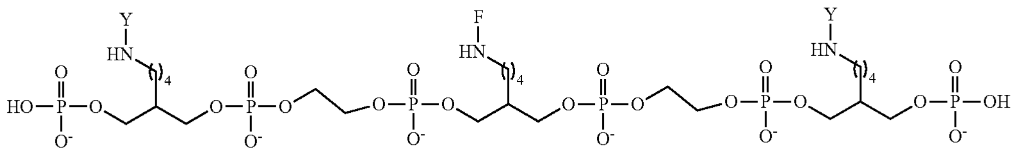 |
| II-2 | 1786.0 / 1785.8 | 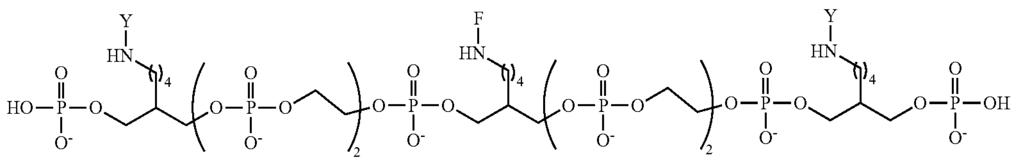 |
| II-3 | 1111.3 / 1112.0 | 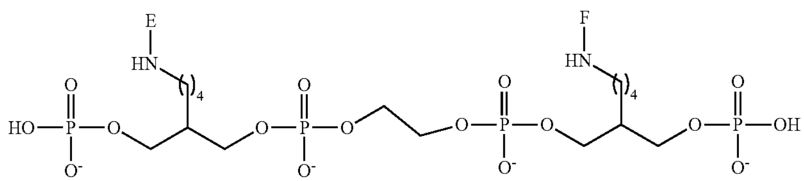 |
| II-4 | 1235.4 / 1236.0 | 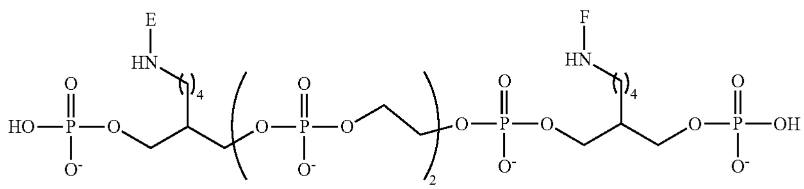 |
| II-5 | 1856.0 / 1856.3 | 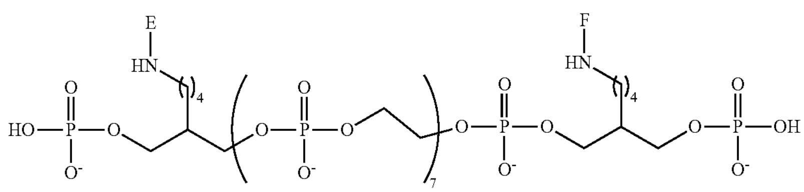 |
| II-6 | 1979.8 / 1980.3 | 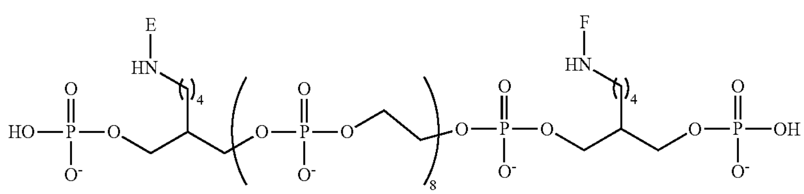 |
| II-7 | 2104.0 / 2104.4 | 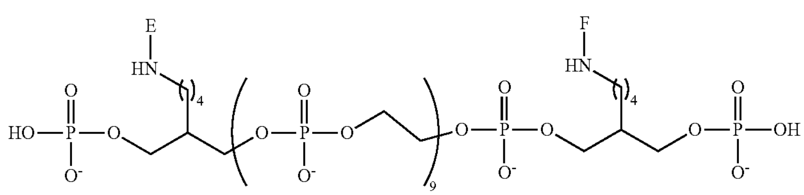 |
| II-8 | 2227.8 / 2228.4 | 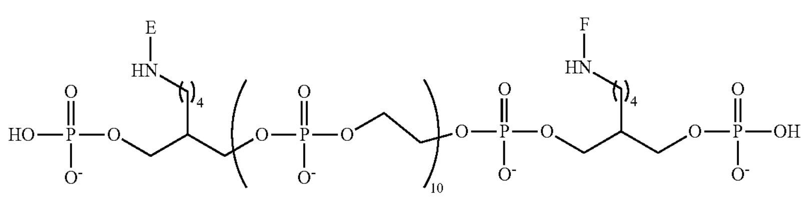 |

As used in Tables 2 and 3 above and throughout this disclosure, F and F' refer to a fluorescein moiety have the following structures, respectively:

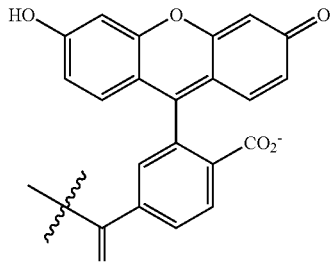
F

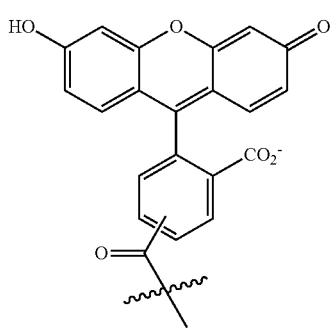
F'

As used in Tables 2 and 3 above and throughout this disclosure dT refers to the following structure:

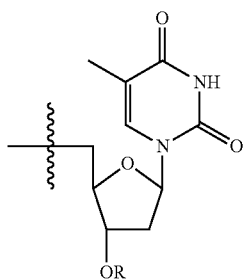
dT wherein:

R is H or a direct bond.

As used in Tables 2 and 3 above and throughout this disclosure. B and B' refer to the following structures, respectively:

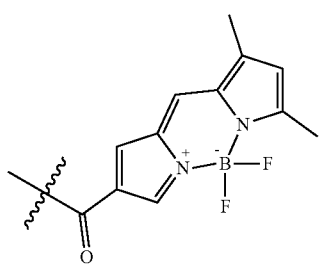
B

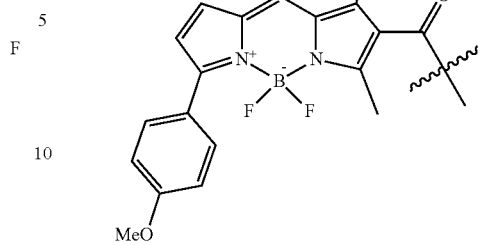
B'

As used in Tables 2 and 3 above and throughout this disclosure, T refers to the following structure:

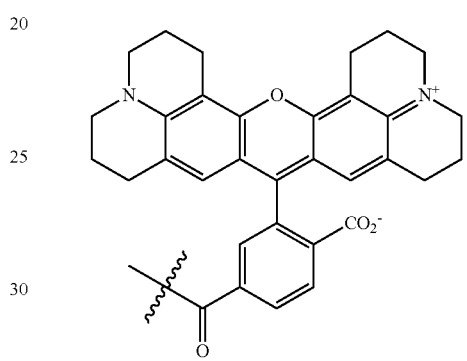
T

As used in Tables 2 and 3 above and throughout this disclosure, C refers to the following structure:

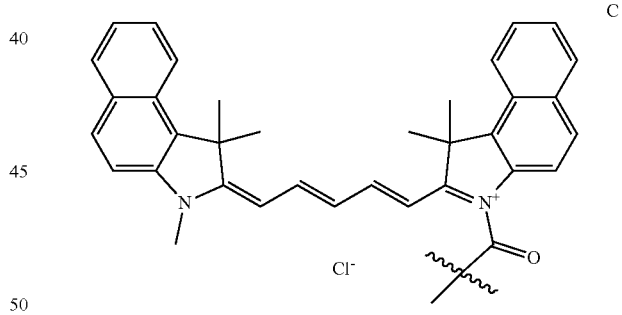
C

As used in Tables 2 and 3 above and throughout this disclosure, Y refers to the following structure:

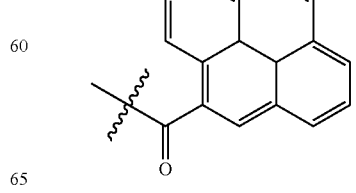
Y

Alternatively, for any of the embodiments of F, F', B, B', C, and Y disclosed herein, the oxo moiety

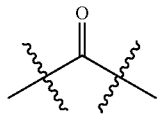 [SMILES: *C(*)=O]

may be replaced with a direct bond to the remainder of the molecule. In some of the foregoing embodiments, $L^1$ is alkylene, e.g., methylene or ethylene.

The presently disclosed dye combinations are "tunable," meaning that by proper selection of the variables in any of the foregoing compounds, one of skill in the art can arrive at a compound having a desired and/or predetermined FRET properties (e.g., fluorescence emission signal, Stoke's shift). The "tunability" of the compounds allows the user to easily arrive at compounds having the desired Stoke's shift, fluorescence signal and/or color for use in a particular assay or for identifying a specific analyte of interest. Although all variables may have an effect on the FRET properties of the compounds, proper selection of $M^1$, $M^2$, $L^4$, m and n is believed to play an important role in the molar fluorescence of the compounds. Accordingly, in one embodiment is provided a method for obtaining a compound having a desired FRET fluorescence properties, the method comprising selecting $M^1$ and $M^2$ moieties having known interactive properties, preparing a compound of structure (I) or (II) comprising the $M^1$ and $M^2$ moieties, and selecting the appropriate variables for $L^4$, m and n to arrive at the desired FRET properties (e.g., Stoke's shift, reduction of donor emission signal).

FRET fluorescence emission signal in certain embodiments can be expressed in terms of the fold increase or decrease relative to the FRET fluorescence emission signal of the parent fluorophore(s) (e.g., monomers). In some embodiments the FRET fluorescence emission signal of the present compounds is 1.1×, 1.5×, 2×, 3×, 4×, 5×, 6×, 7×, 8×, 9×, 10×, or greater than 10× relative to the parent chromophore(s)/fluorophore(s). Various embodiments include preparing compounds having the desired fold increase in fluorescence relative to the parent fluorophore by proper selection of $L^4$, m and n.

For ease of illustration, various compounds comprising phosphorous moieties (e.g., phosphate and the like) are depicted in the anionic state (e.g., —OPO(OH)O⁻, —OPO$_3^{2-}$). One of skill in the art will readily understand that the charge is dependent on pH and the uncharged (e.g., protonated or salt, such as sodium or other cation) forms are also included in the scope of embodiments of the invention.

Compositions comprising any of the foregoing compounds and one or more analyte molecules (e.g., biomolecules) are provided in various other embodiments. In some embodiments, use of such compositions in analytical methods for detection of the one or more analyte molecules is also provided.

In still other embodiments, the compounds are useful in various analytical methods. For example, in certain embodiments the disclosure provides a method of staining a sample, the method comprising adding to said sample a compound of any of the foregoing embodiments (e.g., a compound of structure (I) or (II)), in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or non-polymeric bead.

In even more embodiments, the optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:
  (a) providing a polymer compound according to the foregoing embodiments (e.g., structure (I) or structure (II)), wherein the polymer compound comprises covalent bond to the analyte molecule (e.g., one of $R^2$ or $R^3$ is a linker comprising a covalent bond to the analyte molecule, and the other of $R^2$ or $R^3$ is H, OH, alkyl, alkoxy, alkylether or —OP(=$R_a$)($R_b$)$R_c$); and
  (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
  (a) admixing any of the foregoing polymer compounds wherein the compound comprises a covalent bond to Q selected from Table 1, with the analyte molecules; and
  (b) forming a bio-conjugate of the polymer compound and the analyte molecule; and
  (c) detecting the bio-conjugate by its visible properties.

Some embodiments provide use of the composition in an analytical method for detection of the one or more analyte molecules.

In addition to the above methods, embodiments of the compounds of structure (I) and structure (II) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by conjugating a compound of structure (I) and structure (II) to an antibody or sugar or other moiety that preferentially binds cancer cells; imaging in surgical procedures; binding of histones for identification of various diseases; drug delivery, for example by replacing the $M^1$ and/or $M^2$ moiety in a compound of structure (I) and structure (II) with an active drug moiety; and/or contrast agents in dental work and other procedures, for example by preferential binding of the compound of structure (I) and structure (II) to various flora and/or organisms.

It is understood that any embodiment of the compounds of structure (I) and structure (II), as set forth above, and any specific choice set forth herein for a $R^1$, $R^2$, $R^3$, $R^4$, $R^5$, $L^1$, $L^2$, $L^3$, $L^4$, $M^1$, $M^2$, m and/or n variable in the compounds of structures (I) or (II), as set forth above, may be independently combined with other embodiments and/or variables of the compounds of structures (I) or (II) to form embodiments of the invention not specifically set forth above. In addition, in the event that a list of choices is listed for any particular $R^1$, $R^2$, $R^3$, $R^4$, $R^5$, $L^1$, $L^2$, $L^3$, $L^4$, $M^1$, $M^2$, m and/or n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) or (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

In particular, methods for preparing embodiments of the compounds disclosed herein (e.g., structures (I) and (II)) can be found, for example, in PCT Pub. Nos. WO 2015/027176, WO 2016/138461, WO 2016/183185, WO 2017/173348, WO 2017/173355, WO 2017/177065, WO 2017/196954, WO 2017/214165, and WO 2018/022925, each of which are hereby incorporated by reference in their entirety.

Reaction Scheme I

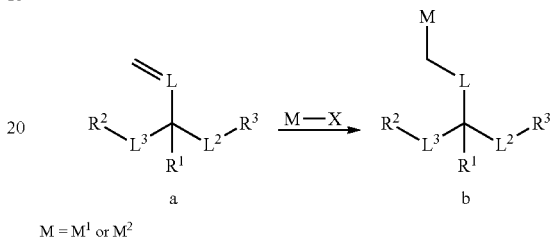

$M = M^1$ or $M^2$

Reaction Scheme I illustrates an exemplary method for preparing an intermediate useful for preparation of compounds of structures (I) and (II), where $R^1$, $L^2$, and $L^3$ are as defined above, $R^2$ and IV are as defined above or are protected variants thereof and L is an optional linker. Referring to Reaction Scheme 1, compounds of structure a can be purchased or prepared by methods well-known to those of ordinary skill in the art. Reaction of a with M-X, where X is a halogen such as bromo, under Suzuki coupling conditions known in the art results in compounds of structure b. Compounds of structure b can be used for preparation of compounds of structures (I) or (II) as described below.

Reaction Scheme II

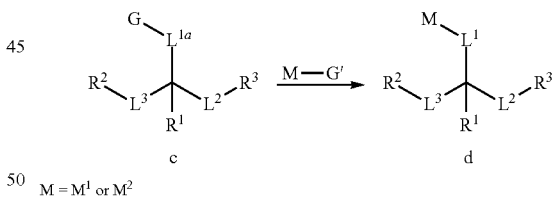

$M = M^1$ or $M^2$

Reaction Scheme II illustrates an alternative method for preparation of intermediates useful for preparation of compounds of structures (I) and (II). Referring to reaction Scheme II, where $R^1$, $L^1$, $L^2$, $L^3$, and G as defined above, and $R^2$ and $R^3$ are as defined above or are protected variants thereof, a compound of structure c, which can be purchased or prepared by well-known techniques, is reacted with M-G' to yield compounds of structure d. Here, G and G' represent functional groups having complementary reactivity (i.e., functional groups which react to form a covalent bond). G' may be pendant to M or a part of the structural backbone of M. G may be any number of functional groups described herein, such as an alkyne or amine.

The compound of structures (I) and (II) may be prepared from one of structures b or d by reaction under well-known automated DNA synthesis conditions with a phosphoramidite compound having the following structure (e):

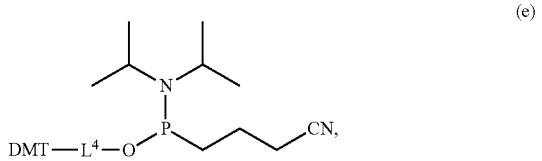

(e)

wherein each L⁴ is independently an optional linker.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Compounds of structures (I) or (II) are prepared by oligomerization of intermediates b or d and e according to the well-known phophoramidite chemistry described above. The desired number of m and n repeating units is incorporated into the molecule by repeating the phosphoramidite coupling the desired number of times. It will be appreciated that compounds of structure (III) as, described below, can be prepared by analogous methods.

In various other embodiments, compounds useful for preparation of the compound of structures (I) or (II) are provided. The compounds can be prepared as described above in monomer, dimer and/or oligomeric form and then the M¹ and/or M² moieties covalently attached to the compound via any number of synthetic methodologies (e.g., the "click" reactions described above) to form compounds of structures (I) or (II). Accordingly, in various embodiments a compound is provided having the following structure (III):

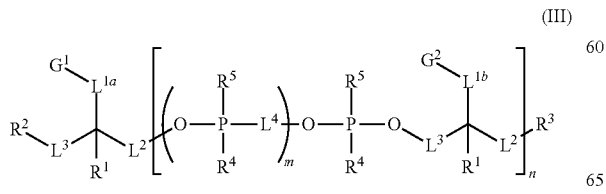

(III)

or a stereoisomer, salt or tautomer thereof, wherein:

$G^1$ and $G^2$ are, at each occurrence, independently a moiety comprising a reactive group capable of forming a covalent bond with a complementary reactive group;

$L^{1a}$ and $L^{1b}$ are, at each occurrence, an optional linker;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene or heteroalkylene linker;

$R^1$ is, at each occurrence, independently H, alkyl or alkoxy;

$R^2$ and $R^3$ are each independently H, OH, SH, alkyl, alkoxy, alkylether, $-OP(=R_a)(R_b)R_c$, Q, a linker comprising a covalent bond to Q, a linker comprising a covalent bond to an analyte molecule, a linker comprising a covalent bond to a solid support or a linker comprising a covalent bond to a further compound of structure (II), wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, alkyl, alkoxy, alkylether alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O⁻, S⁻, $OR_d$ or $SR_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater, provided that at least one occurrence of m is an integer of one or greater; and n is an integer of one or greater.

In various embodiments a compound is provided having the following structure (IV):

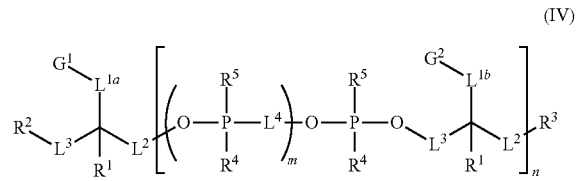

(IV)

or a stereoisomer, salt or tautomer thereof, wherein:

$G^1$ and $G^2$ are, at each occurrence, independently a moiety comprising a reactive group capable of forming a covalent bond with a complementary reactive group;

$L^{1a}$ and $L^{1b}$ are, at each occurrence, independently an optional linker;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene or heteroalkylene linker;

$R^1$ is, at each occurrence, independently H, alkyl or alkoxy;

R² and R³ are each independently H, OH, SH, alkyl, alkoxy, alkylether, —OP(=R$_a$)(R$_b$)R$_c$, Q, a linker comprising a covalent bond to Q, a linker comprising a covalent bond to an analyte molecule, a linker comprising a covalent bond to a solid support or a linker comprising a covalent bond to a further compound of structure (II), wherein: R$_a$ is O or S; R$_b$ is OH, SH, O⁻, S⁻, OR$_d$ or SR$_d$; R$_c$ is OH, SH, O⁻, S⁻, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and R$_d$ is a counter ion;

R⁴ is, at each occurrence, independently OH, SH, O⁻, S⁻, OR$_d$ or SR$_d$;

R⁵ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater, provided that at least one occurrence of m is an integer of one or greater; and n is an integer of one or greater.

G¹ and G² moieties in the compound of structures (III) and (IV) can be selected from any moiety comprising a group having the appropriate reactivity group for forming a covalent bond with a complementary group on an M¹ or M² moiety. In exemplary embodiments, the G¹ and G² moieties can be selected from any of the Q moieties described herein, including those specific examples provided in Table 1. In some embodiments, G¹ or G² or both comprise, at each occurrence, independently a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, G¹ or G² or both are, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group.

In other embodiments, G¹ or G² or both comprise, at each occurrence, independently an alkyne or an azide group. In different embodiments, G¹ or G² or both comprise, at each occurrence, independently a reactive group capable of forming a functional group comprising an alkene, ester, amide, thioester, disulfide, carbocyclic, heterocyclic or heteroaryl group, upon reaction with the complementary reactive group. For example, in some embodiment the heteroaryl is triazolyl.

In various other embodiments of the compound of structures (III) and (IV), L² and L³ are, at each occurrence, independently C$_1$-C$_6$ alkylene, C$_2$-C$_6$ alkenylene or C$_2$-C$_6$ alkynylene.

In other embodiments of structures (III) and (IV), each L$^{1a}$ is absent. In other embodiments, each L$^{1a}$ is present, for example L$^{1a}$ is, at each occurrence, independently heteroalkylene. In certain embodiments, L$^{1a}$ has the following structure:

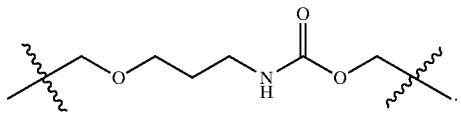 [SMILES: *COCCCNC(=O)OC*]

In other of any of the foregoing embodiments of structures (III) and (IV), G¹ or G² or both is, at each occurrence, independently

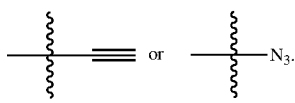

In various embodiments, G¹ alkynyl at each occurrence, such as ethynyl and G² is —NH$_2$. In other embodiments, G¹ is an azide at each occurrence and G² is —NH$_2$ at each occurrence.

In various embodiments, G² alkynyl at each occurrence, such as ethynyl and G¹ is —NH$_2$. In other embodiments, G² is an azide at each occurrence and G¹ is —NH$_2$ at each occurrence.

The efficiency of the FRET process depends, in part, on characteristics of the chromophores. Specifically, high efficiency FRET requires a large overlap between the absorbance spectrum of the donor chromophore and the emission spectrum of the acceptor chromophore. Additionally, the distance and orientation of the chromophores plays an important role. FRET efficiency is inversely proportional to the 6$^{th}$ power of the distance between the chromophores and the angle of the transition dipole moment should substantially align to be parallel (i.e., be near to 0° or 180°). Accordingly, in certain embodiments, covalent attachments of a first and a second chromophore to the polymer backbone are selected so distance between the first and second chromophore is minimized and transition dipole moments substantially align. The efficiency of FRET can be expressed according to the following equation:

$$E_{FRET} \frac{Ro^6}{Ro^6 + R^6}$$

wherein $E_{FRET}$ is FRET efficiency, R is the distance between chromophores, and Ro is expressed according to the following equation:

$$Ro = (8.8 \times 10^{23} JK^2 Q_o n^{-4})^{1/6}$$

wherein J is the spectral overlap of the absorbance spectrum of the acceptor and the emission spectrum of the donor, $Q_o$ is donor quantum efficiency, $n^{-4}$ is the index of medium between the donor and acceptor (constant), and $K^2$ is the dipole directions matching.

Accordingly, one embodiment provides a polymer compound comprising an acceptor chromophore having an acceptor transition dipole moment and being covalently linked to a polymer backbone, and a donor chromophore having a donor transition dipole moment and being covalently linked to the polymer backbone, wherein the polymer compound adopts a confirmation in solution at physiological conditions wherein the effective distance between the acceptor chromophore and the donor chromophore is less than about 50.0 nm and the acceptor transition dipole and the donor transition dipole are substantially parallel.

In some embodiments, the effective distance between the acceptor chromophore and the donor chromophore is less than about 25.0 nm. In some embodiments, the effective distance between the acceptor chromophore and the donor chromophore is less than about 10.0 nm. In some embodiments, the effective distance between the acceptor chromophore and the donor chromophore is less than about 30.0 nm, less than about 27.0 nm, less than about 22.0 nm, less than about 20.0 nm, less than about 17.0 nm, less than about 15.0 urn, less than about 12.0 nm, less than about 11.0 nm, less than about 9.0 nm, less than about 8.0 nm, less than about 7.0 nm, less than about 6.0 nm, less than about 5.0 nm, less than about 4.0 nm, less than about 3.0 nm, less than about 2.0 nm, or less than about 1.0 nm.

In some embodiments, the acceptor chromophore is a fluorescent dye moiety. In certain embodiments, the donor chromophore is a fluorescent dye moiety. In certain related embodiments, the acceptor chromophore and the donor chromophore are both fluorescent dye moieties.

In some embodiments, the angle between the acceptor transition dipole moment and the donor transition dipole moment ranges from 120° to 180°. For example, in some embodiments, the angle between the acceptor transition dipole moment and the donor transition dipole moment ranges from 125° to 180°, from 130° to 180°, from 140° to 180°, from 150° to 180°, from 160° to 180°, from 170° to 180°, from 172° to 180°, from 175° to 180°, or from 177° to 180°.

In certain embodiments, the angle between the acceptor transition dipole moment and the donor transition dipole moment ranges from 0° to 60°. For example, For example, in some embodiments, the angle between the acceptor transition dipole moment and the donor transition dipole moment ranges from 0° to 50°, from 0° to 40°, from 0° to 30°, from 0° to 20°, from 0° to 10°, from 0° to 8°, from 0° to 5°, from 0° to 3°, or from 0° to 2°.

In some more specific embodiments, the polymer compound further comprises a first acceptor chromophore is covalently linked at a proximal end of the polymer backbone, a second acceptor chromophore is covalently linked at a distal end of the polymer backbone, and a donor chromophore is covalently linked between the proximal and distal ends of the polymer backbone.

In certain embodiments, the polymer backbone comprises a phosphate linker. In some embodiments, the polymer backbone comprises a plurality of phosphate linkers.

In some related embodiments, the polymer backbone comprises an alkylene oxide linker. In some more specific embodiments, the alkylene oxide is ethylene oxide. In some specific embodiments, the polymer backbone comprises a HEG linker, a C linker or combinations thereof.

In some embodiments, the polymer compound has a molecular weight less than 20,000 g/mol. In some embodiments, the polymer compound has a molecular weight less than 19,000 g/mol, 18,500 g/mol, 18,000 g/mol, 17,500 g/mol, 17,000 g/mol, 16,500 g/mol, 16,000 g/mol, 15,500 g/mol, 15,000 g/mol, 14,500 g/mol, 14,000 g/mol, 13,500 g/mol, 13,000 g/mol, 12,500 g/mol, 11,500 g/mol, 11,000 g/mol, 10,500 g/mol, 10,000 g/mol, 9,500 g/mol, 9,000 g/mol, 8,500 g/mol, 8,000 g/mol, 7,500 g/mol, 7,000 g/mol, 6,500 g/mol, 6,000 g/mol, 5,500 g/mol, 5,000 g/mol, 4,500 g/mol, 4,000 g/mol, 3,500 g/mol, 3,000 g/mol, 2,500 g/mol, 2,000 g/mol, 1,500 g/mol, or 1,000 g/mol.

In some embodiments the polymer compound is not a peptide or protein. In some other embodiments, the polymer backbone has no amide bonds.

The following Examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-$C_{18}$ column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Example 1

SYNTHESIS OF POLYMER BACKBONE AND DERIVATIZATION

Synthesis of Representative Amine/Alkyne Polymer Compounds

Polymers were synthesized using an Applied Biosystems 394 DNA/RNA synthesizer on a 0.5-1 µmol scale. The polymer compounds were synthesized directly on CPG beads or a polystyrene solid support. Synthesis was carried out in the 3' to 5' direction using standard solid phase DNA synthetic methodology (i.e., β-cyanoethyl phosphoramidite coupling chemistry). Monomer reagents (e.g., Fluoroside phosphoramidites, $C_2$ alkyl phosphoramidite, hexaethylene glycol phosphoramidite, amino phosphoramidites, and alkyne phosphoramidites) were dissolved in acetonitrile and dichloromethane to make a 0.1 M stock solution. Monomer reagents were added in successive order using the following synthesis cycle:

1) removal of the 5'-dimethoxytrityl protecting group with dichloroacetic acid in dichloromethane or toluene;
2) coupling the next phosphoramidite monomer reagent with activator reagent (0.2 M ETT) in acetonitrile;
3) oxidation of phosphate (III) to form stable phosphate (V) with iodine/pyridine/water; and
4) capping unreacted 5'-hydroxyl groups with acetic anhydride/1-methylimidizole/acetonitrile.

The synthesis cycle was repeated until the desired polymer compound was assembled. Upon completion, the terminal monomethoxytrityl (MMT) group or dimethoxytrityl (DMT) group was removed using dichloroacetic acid in dichloromethane or toluene. Following synthesis, the support was treated with 20% diethylamine in acetonitrile for 15 minutes.

The representative amine polymers were then cleaved from the solid support using concentrated aqueous ammonium hydroxide at 55° C. for 2 hours. Constructs were characterized by ESI-MS to confirm mass and purity. Concentration was determined by UV.

Chromophore Coupling to Amine/Alkyne Polymer Compounds

Representative polymer constructs were synthesized to have orthogonal reactive groups (e.g., amine and alkyne) so distinct dyes moieties could be added. For instance, click chemistry was used to attach a first fluorophore to alkynes of the polymer.

A 100 mM sodium ascorbate solution and 500 mM phosphate buffer pH 7.6 were prepared. A first desired dye moiety comprising an azide functional group was dissolved in dimethyl sulfoxide at a concentration of 100 mM ("dye solution").

The 100 mM sodium ascorbate solution (i.e., a 2.5:1:1 mixture of 100 mM sodium ascorbate/100 mM THTPA/50 mM copper sulfate) was prepared by adding equal volumes of THTPA and copper sulfate and allowing the mixture to sit for 5-10 minutes followed by the addition of sodium ascorbate.

The phosphate buffer, dye solution, polymer compound and extra DMSO were mixed together followed by the sodium ascorbate solution. Reactions were prepared having final polymer concentration of 0.5 mM, phosphate buffer concentration of 100 mM, 50-60% DMSO and 5-10 fold excess dye. Reactions were placed in the dark overnight on a rotator or vortex. Samples were diluted with water and desalted using G-25 Sephadex resin. Samples were collected and characterized by ESI-MS to confirm mass and purity. Following sample analysis the polymer compounds were lyophilized.

Addition of a second desired dye moiety (e.g., fluorophore or other label) to representative polymer compounds was achieved using NHS-ester/amine coupling chemistry. A sodium tetraborate buffer pH 9 stock solution ("borate buffer") was initially prepared. A second dye moiety comprising an NITS-ester was dissolved at a concentration of 100-200 mM in DMSO. Reactions were prepared to have a polymer concentration of 1-2 mM, a borate buffer concentration of 100 mM, 30-75% DMSO and a 5-10-fold excess of dye. Reactions were placed in the dark overnight on a rotator or vortex. Samples were diluted with water and desalted using G-25 Sephadex resin. Samples were collected and characterized by ESI-MS to confirm mass and purity. Additionally, characterization by UV and fluorescence spectroscopy was used to determine FRET properties.

Example 2

OPTIMIZATION OF POLYMER BACKBONE LENGTH BETWEEN CHROMOPHORES—TEST 1

Variation in the length polymer backbone between pendant chromophores was compared to determine the optimum spacer length (i.e., number hexaethylene glycol or "HEG" units).

Solutions were prepared at a concentration of 100 mM for Compounds I-1, 1-2, I-3, and I-4. The emission spectrum for each sample was detected using an excitation wavelength of 494 nm. The experimental results indicate that the optimum spacing for this combination (i.e., a BODIPY-TMR and 6-FAM) is a spacer of two hexaethylene glycol units. The experimental results shown in FIG. 1 indicate the donor emission signal is minimized and the acceptor emission signal is relatively high. The molecular modeling calculations were substantially consistent with experimental data, except for the trans version of Compound I-1.

Example 3

OPTIMIZATION OF POLYMER BACKBONE LENGTH BETWEEN CHROMOPHORES—TEST 2

Representative polymer compounds were tested, each having a FAM chromophore (FRET donor) and a Texas Red chromophore (FRET acceptor). The representative polymer compounds were compared to determine the optimum spacer length.

Figure 2:
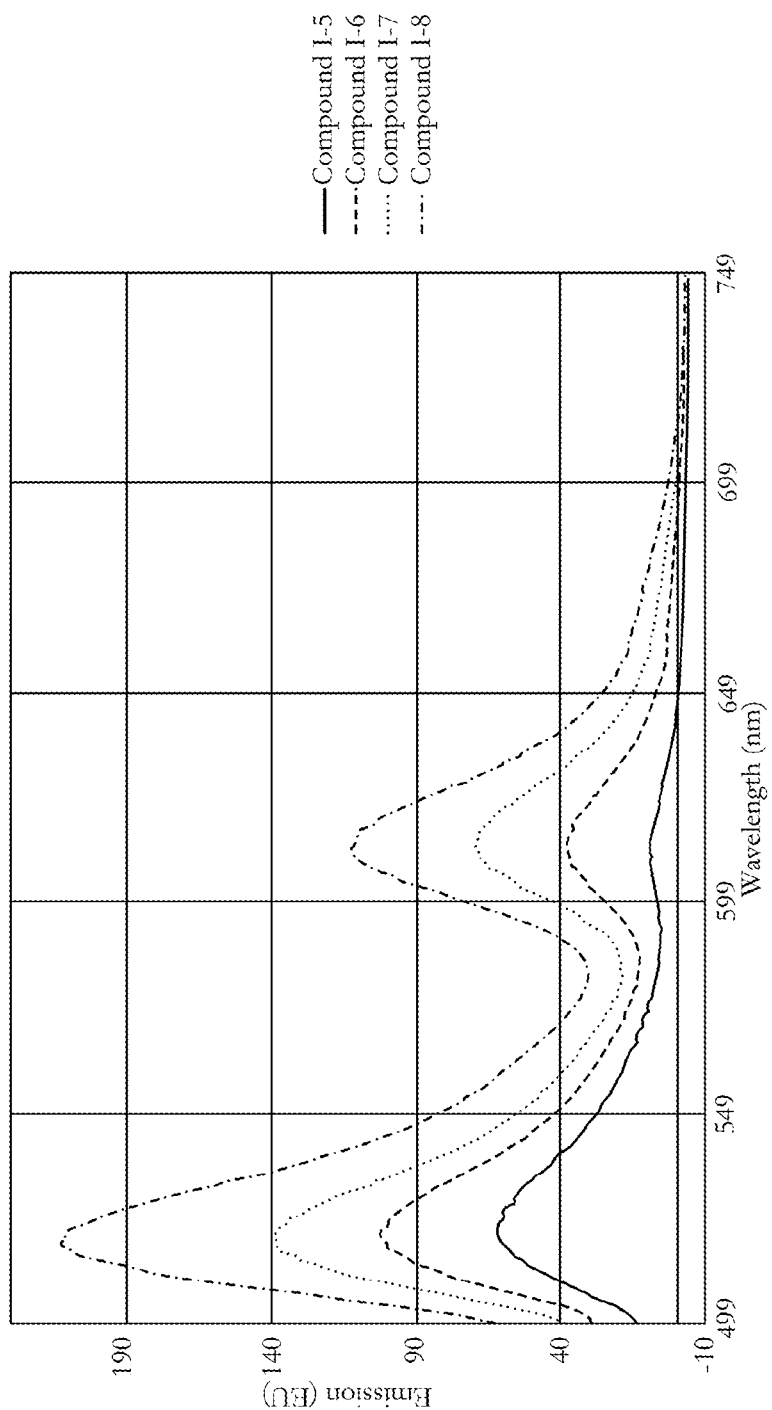
FIG. 2 illustrates the emission spectra of Compounds I-5 through I-8, each having various spacer lengths between pendant Texas Red and fluorescein-based chromophores.

Solutions were prepared at a concentration of 200 nM for Compounds I-5, I-6, I-7 and I-8 and a pH of 7.0. The emission spectrum for each sample was detected using an excitation wavelength of 488 nm (emission detected at 620 nm). The results are shown in FIG. 2. The data suggest that the length of the spacer between the respective chromophores does not necessarily show higher FRET efficiency. For this combination (i.e., FAM and Texas Red), the molecular modeling calculations are substantially consistent with the experimental results.

Example 4

DONOR EMISSION CHARACTERIZATION

Figure 3:
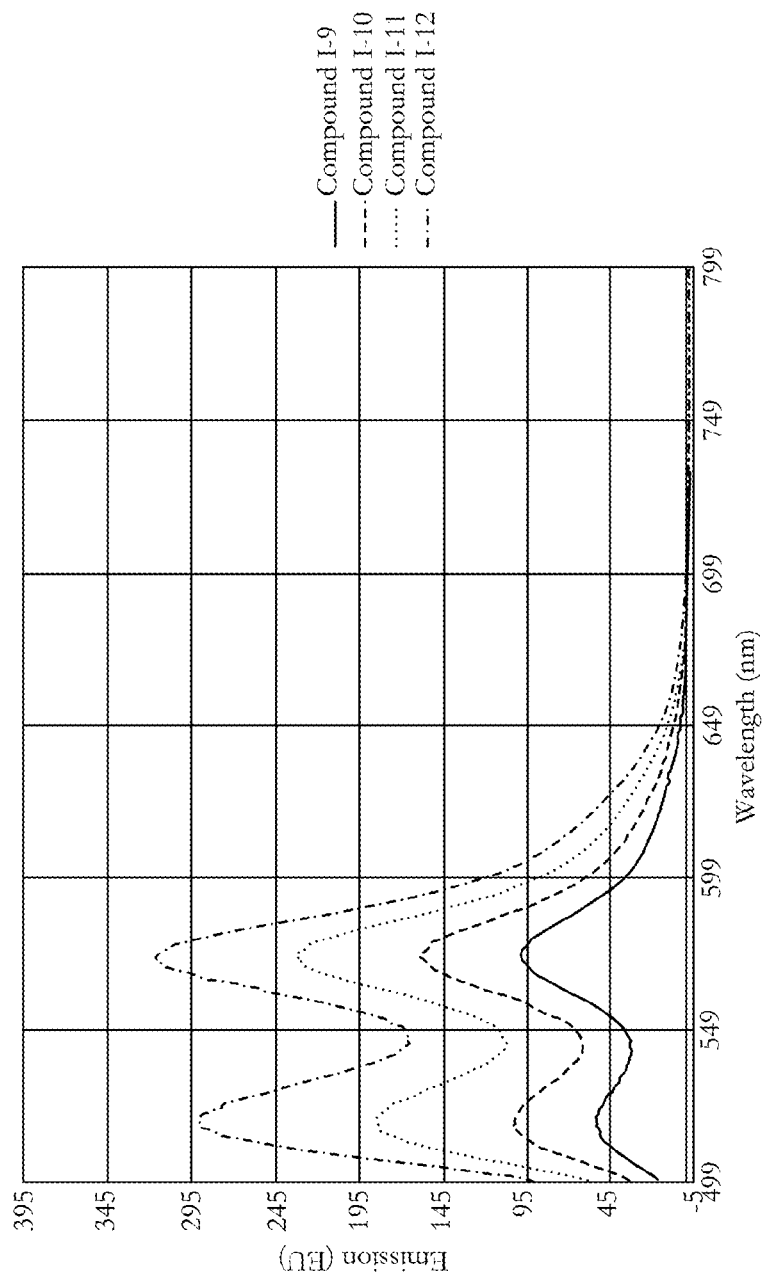
FIG. 3 depicts the emission spectra of Compounds I-9 through I-12 to compare donor emission for representative polymer dye compounds.

Polymer compounds were prepared to determine the effect of relative positioning on brightness of the emission spectra of representative compounds. Representative sample polymers (i.e., Compounds I-9, I-10, I-11, and I-12) were prepared in a solution at a concentration of 100 nM and pH 7.0. Samples were tested using an excitation wavelength of 494 nm and the resultant spectra are shown in FIG. 3. As the data show, the donor emission signal is substantially similar to the acceptor emission signal detected for each of the respective samples.

Figure 4:
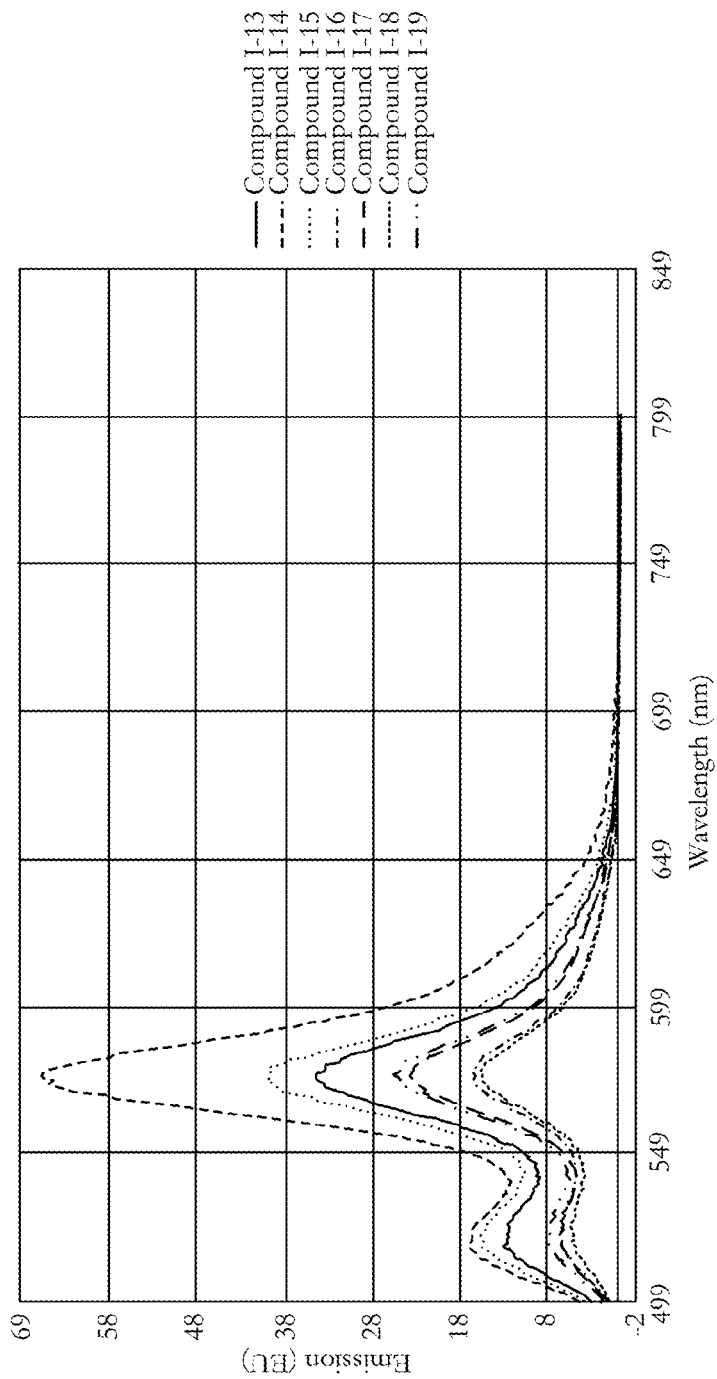
FIG. 4 shows emission spectra of Compounds I-13 through I-19 to compare how changes in the polymer compound affect emission.

Without wishing to be bound by theory, the present Applicants tried to optimize the spacing between the donor and acceptor chromophores and also position donor chromophores between acceptor chromophores along the polymer backbone. This strategy was used to reduce the donor emission signal while maintaining the signal strength of the acceptor chromophore. Samples with various spacer lengths and relative positions of acceptor and donor chromophores were prepared at a concentration of 500 nM at pH 7 and tested (i.e., Compounds I-13, I-14, I-15, I-16, I-17, I-18, and I-19), the results of which are shown in FIG. 4. Applicants unexpectedly found that positioning the donor chromophores between acceptor chromophores on the polymer backbone resulted in a significant reduction in the donor emission signal. Additionally, the optimum spacing length was discovered to be two hexaethylene glycol or "HEG" units as depicted in Compound I-14.

Figure 5:
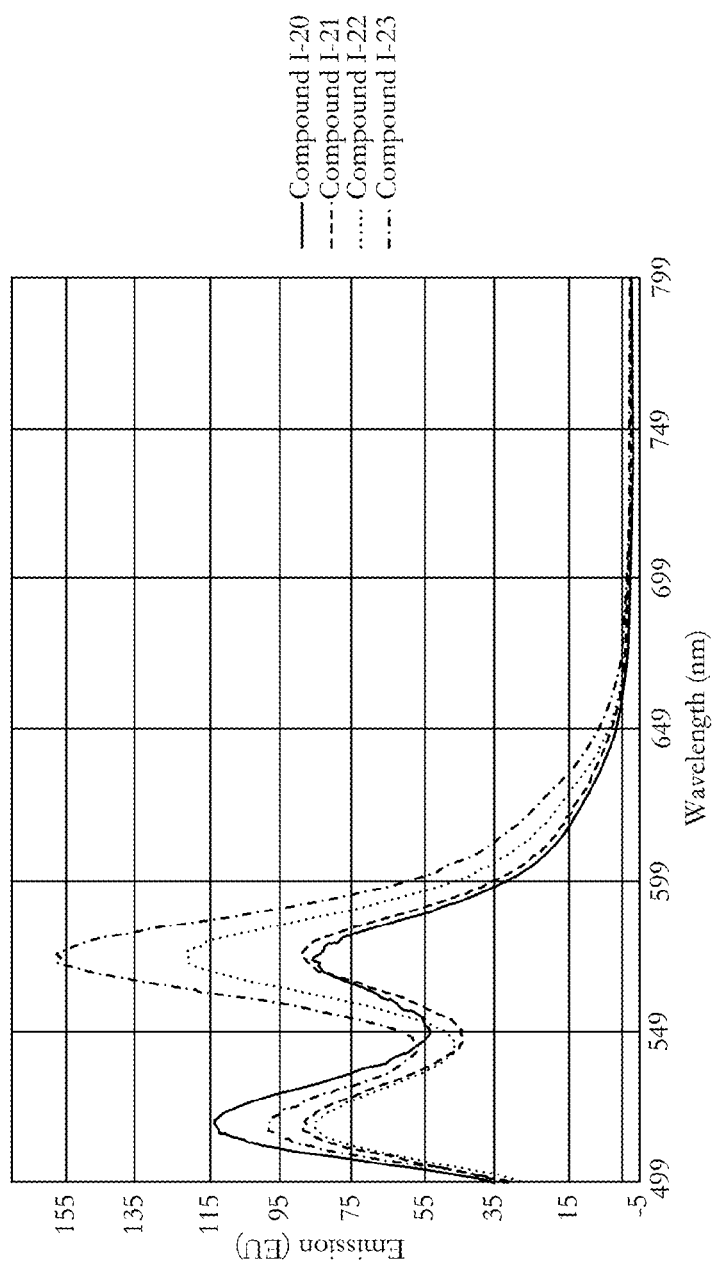
FIG. 5 shows the emission spectra for Compounds I-20 through I-23 and the effect of spacer length on the same.

To further elucidate the relationship between chromophore spacing and relative emission signal strength, samples with variable numbers of HEG units were prepared and tested. Specifically, Compounds I-20, I-21, I-22, and I-23 were each prepared in a solution at a concentration of 5 µM at pH 7.2. The emission spectra for each respective compound are shown in FIG. 5.

Example 5

SYNTHESIS OF TRI-VALENT POLYMER COMPOUNDS

Representative polymer compounds were synthesized having three distinct chromophores. Polymer compounds were synthesized according to Example 1, with the addition of a FAM chromophore via an NHS/amine coupling, a BODIPY-TMR chromophore via an azide/alkyne coupling (i.e., a "click" reaction), and a Texas Red chromophore via an NHS/amine coupling. The desired product (i.e., Compound I-24) was confirmed by ESI-MS [M+H]$^+$=4909.5.

Figure 6:
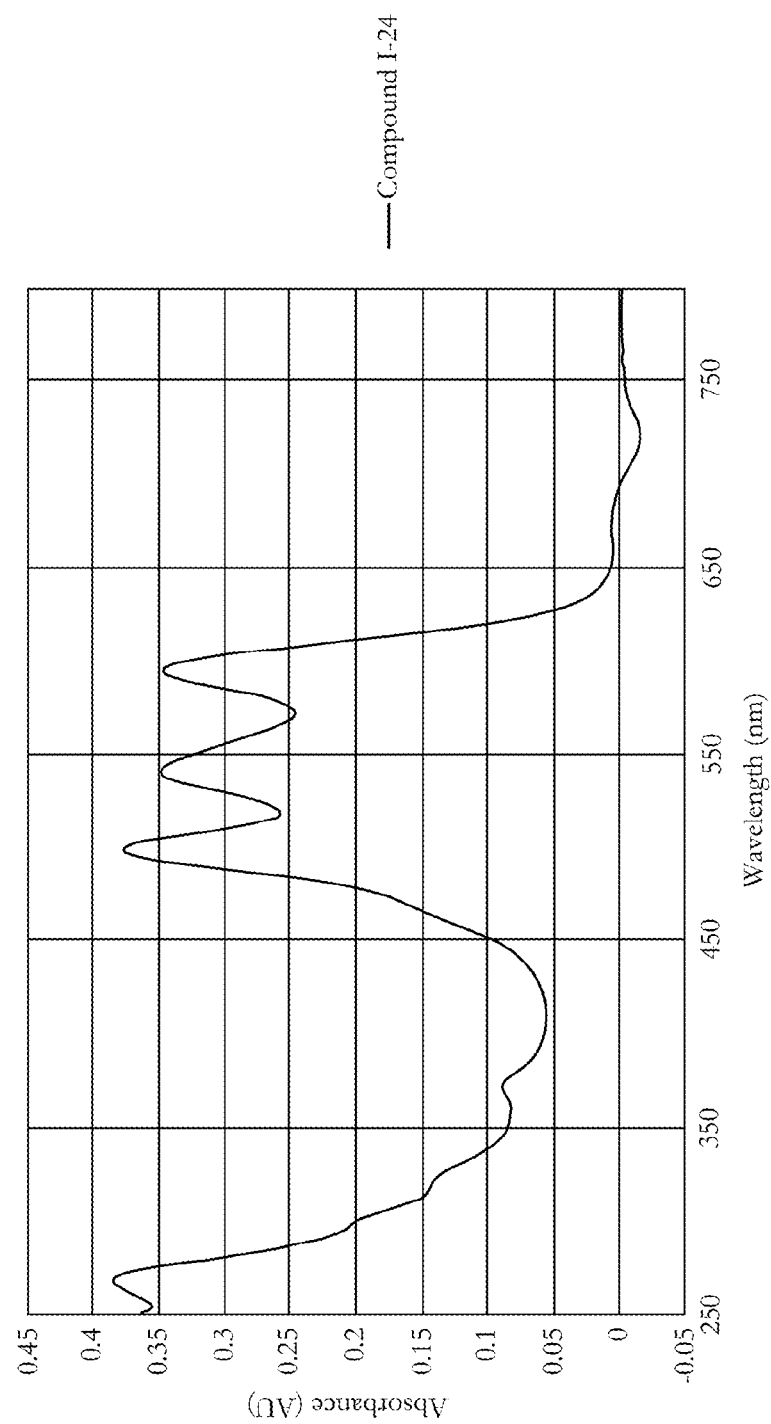
FIG. 6 depicts the absorbance spectrum of Compound I-24, which has 3 distinct dye moieties pendant to the polymer backbone FIG. 7 displays emission spectra for Compound I-24 for pH values of 7.0 and 9.0.
Figure 7:
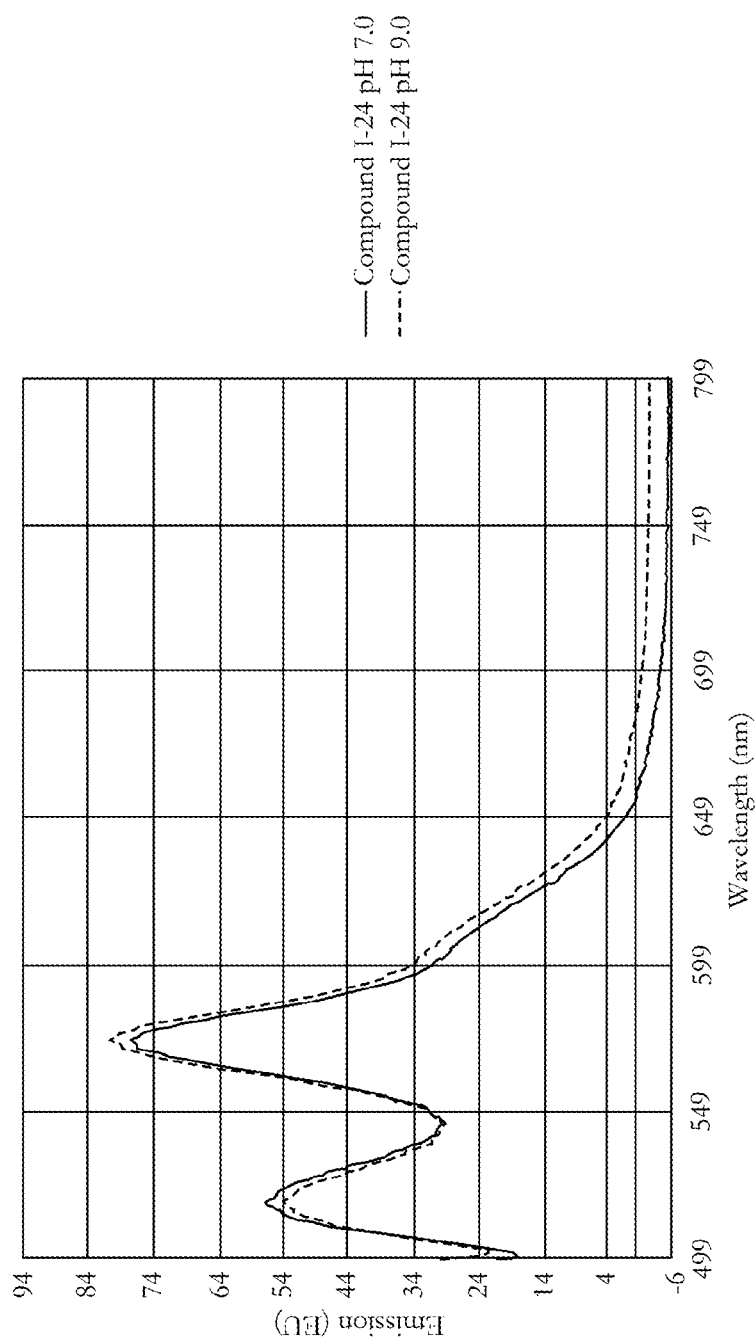

The desired product was taken up in solution at a concentration of 5 μM at pH 7 and the absorbance spectrum was obtained. Absorbance peaks for FAM, BODIPY-TMR, and Texas Red were observed at approximately 510 nm, 540 nm, and 595 nm, respectively (FIG. 6). Solutions at pH 7 and pH 9 were used to determine the emission spectra of Compound I-24 (FIG. 7) showing FRET emission signals of the trivalent polymer compound for FAM, BODIPY-TMR, and Texas Red at approximately 515 nm, 575 nm and 610 nm, respectively.

All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/646,234, filed Mar. 21, 2018, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:
1. A compound having the following structure (I):

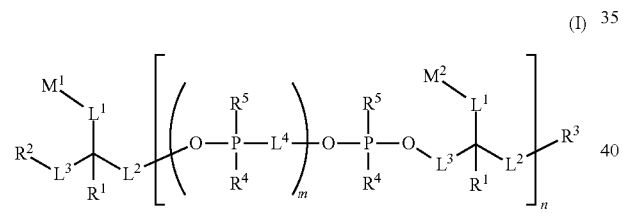

(I)

or a stereoisomer, salt or tautomer thereof, wherein:
M$^1$ is a fluorescent or colored chromophore and M$^2$ is, at each occurrence, independently a fluorescent or colored chromophore, provided that: a) M$^1$ is a FRET acceptor chromophore and at least one occurrence of M$^2$ is a FRET donor chromophore; or b) M$^1$ is a FRET donor chromophore and at least one occurrence of M$^2$ is a corresponding FRET acceptor chromophore, and wherein at least one of the FRET donor chromophores is positioned between two FRET acceptor chromophores;

L$^1$ is, at each occurrence, independently a linker comprising an alkene, ester, amide, thioester, disulfide, carbocyclic, heterocyclic or heteroaryl group;

L$^2$ and L$^3$ are, at each occurrence, independently an optional alkylene, alkenylene, alkynylene, heteroalkylene, heteroalkenylene, heteroalkynylene or heteroatomic linker;

L$^4$ is, at each occurrence, independently an alkylene or heteroalkylene linker;

R$^1$ is, at each occurrence, independently H, alkyl or alkoxy;

R$^2$ and R$^3$ are each independently H, OH, SH, alkyl, alkoxy, alkylether, heteroalkyl, —OP(=R$_a$)(R$_b$)R$_c$, Q, or a protected form thereof, or L';

R$^4$ is, at each occurrence, independently OH, SH, O$^-$, S$^-$, OR$_d$ or SR$_d$;

R$^5$ is, at each occurrence, independently oxo, thioxo or absent;

R$_a$ is O or S;

R$_b$ is OH, SH, O, S, OR$_d$ or SR$_d$;

R$_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

R$_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater; and n is an integer of two or greater.

2. The compound of claim 1, wherein the compound has the following structure (IA):

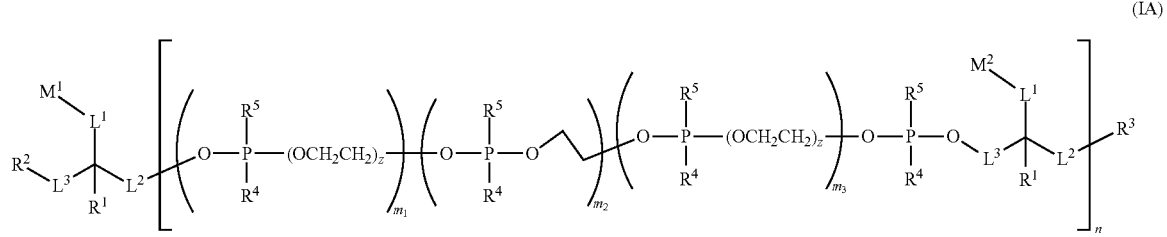

(IA)

wherein:
z is, at each occurrence, independently an integer from 1 to 100; and m$_1$, m$_2$ and m$_3$ are, at each occurrence, independently an integer from 0 to 6.

3. The compound of claim 1, wherein the compound has the following structure (IB):

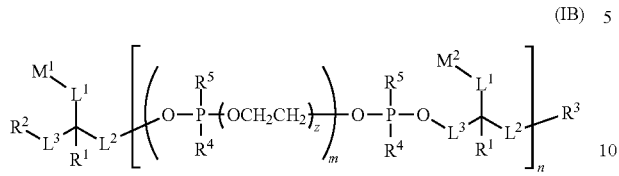

wherein:
z is, at each occurrence, independently an integer from 1 to 100.

4. The compound of claim 1, wherein the compound has the following structure (IC):

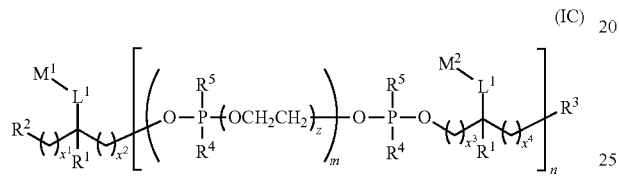

wherein:
$x^1$, $x^2$, $x^3$ and $x^4$ are, at each occurrence, independently an integer from 0 to 6.

5. The compound of claim 2, wherein the compound has the following structure (ID):

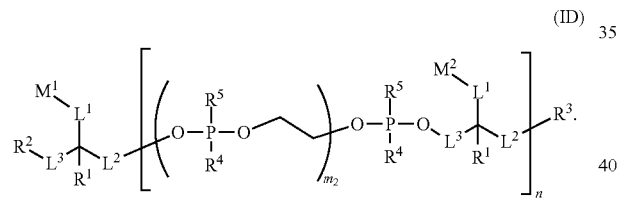

6. The compound of claim 1, wherein the compound has the following structure (IE):

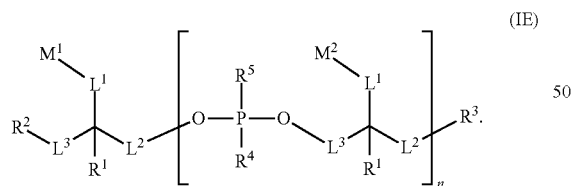

7. A compound having the following structure (II):

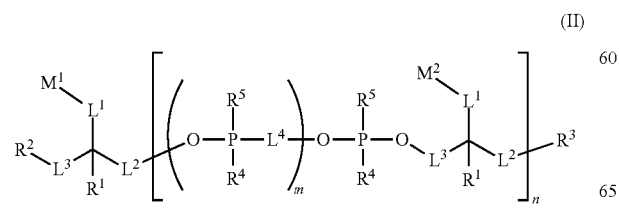

or a stereoisomer, salt or tautomer thereof, wherein:

$M^1$ is a fluorescent or colored chromophore, and $M^2$ is, at each occurrence, independently a fluorescent or colored chromophore, provided that at least one occurrence of $M^2$ is different than $M^1$, $M^1$ and at least one occurrence of $M^2$ combine to form a FRET acceptor-donor pair, and the FRET donor in the FRET acceptor-donor pair is positioned between two FRET acceptors;

$L^1$ is at each occurrence, independently a linker comprising a triazolyl functional group;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene or heteroalkylene linker;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q, or a protected form thereof, or L';

$R^4$ is, at each occurrence, independently OH, SH, O⁻, S⁻, $OR_d$ or $SR_d$;

$R^5$ is, at each occurrence, independently oxo, thioxo or absent;

$R_a$ is O or S;

$R_b$ is OH, SH, O⁻, S⁻, $OR_d$ or $SR_d$;

$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (II);

m is, at each occurrence, independently an integer of zero to two or greater than 6; and n is an integer of two or greater.

8. The compound of claim 1, wherein for at least one occurrence of $L^1$,

A) $L^1$-$M^1$ has one of the following structures:

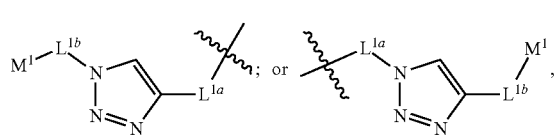

or

B) $L^1$-$M^2$ has one of the following structures:

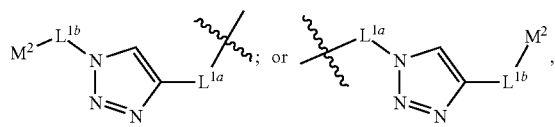

wherein $L^{1a}$ and $L^{1b}$ are each independently optional linkers.

9. The compound of claim 8, wherein $L^{1a}$ and $L^{1b}$, when present, independently have one of the following structures:

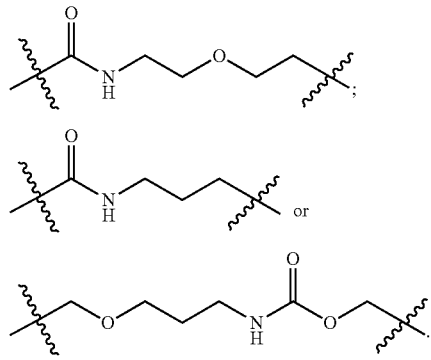

10. The compound of claim 1, wherein $L^1$ has one of the following structures:

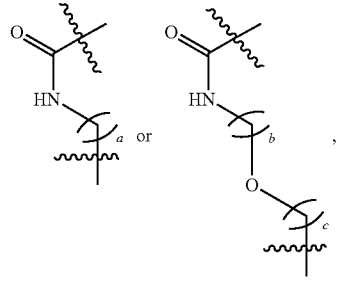

wherein
a, b, and c are each independently an integer ranging from 1-6.

11. The compound of claim 1, wherein $R^4$ is, at each occurrence, independently OH, $O^-$ or $OR_d$, $R^5$ is, at each occurrence, oxo, and $R^1$ is, at each occurrence, H.

12. The compound of claim 1, wherein $R^2$ and $R^3$ are each independently -OP(=$R_a$)($R_b$)$R_c$.

13. The compound of claim 12, wherein $R_c$ is OL'.

14. The compound of claim 13, wherein L' is a heteroalkylene linker to: Q, a targeting moiety, an analyte molecule, a solid support, a solid support residue, a nucleoside or a further compound of structure (I).

15. The compound of claim 14, wherein L' comprises an alkylene oxide or phosphodiester moiety, or combinations thereof.

16. The compound of claim 13, wherein L' has the following structure:

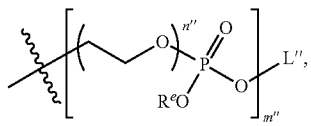

wherein:

m" and n" are independently an integer from 1 to 10;

$R^e$ is H, an electron pair or a counter ion; and

L" is $R^e$ or a direct bond or linkage to: Q, a targeting moiety, an analyte molecule, a solid support, a solid support residue, a nucleoside or a further compound of structure (I).

17. The compound of claim 1, wherein Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group.

18. The compound of claim 1, wherein Q has one of the following structures:

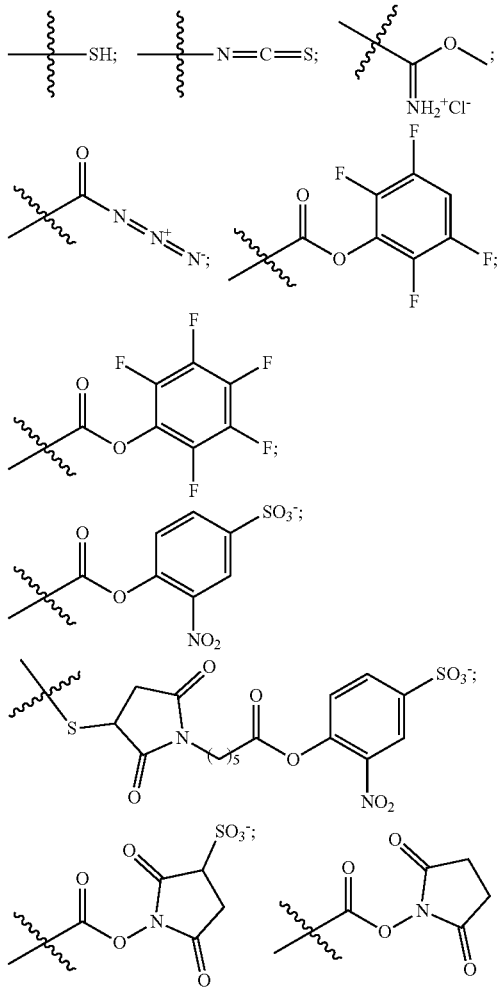

-continued
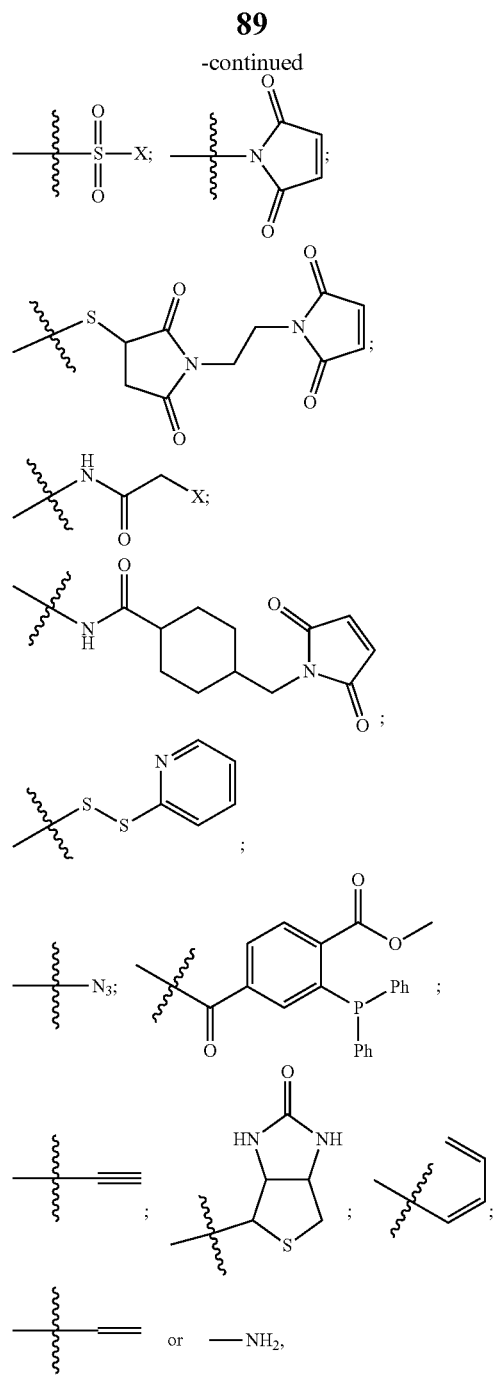
wherein each X is independently a halogen.
19. The compound of claim 1, wherein $R^2$ or $R^3$ has one of the following structures:
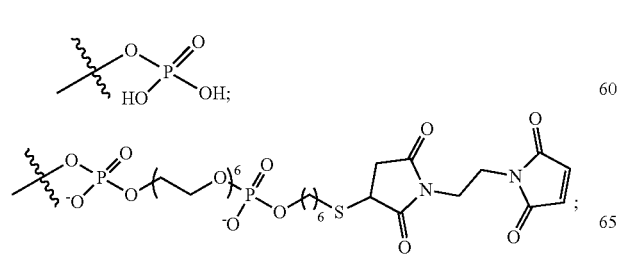
-continued
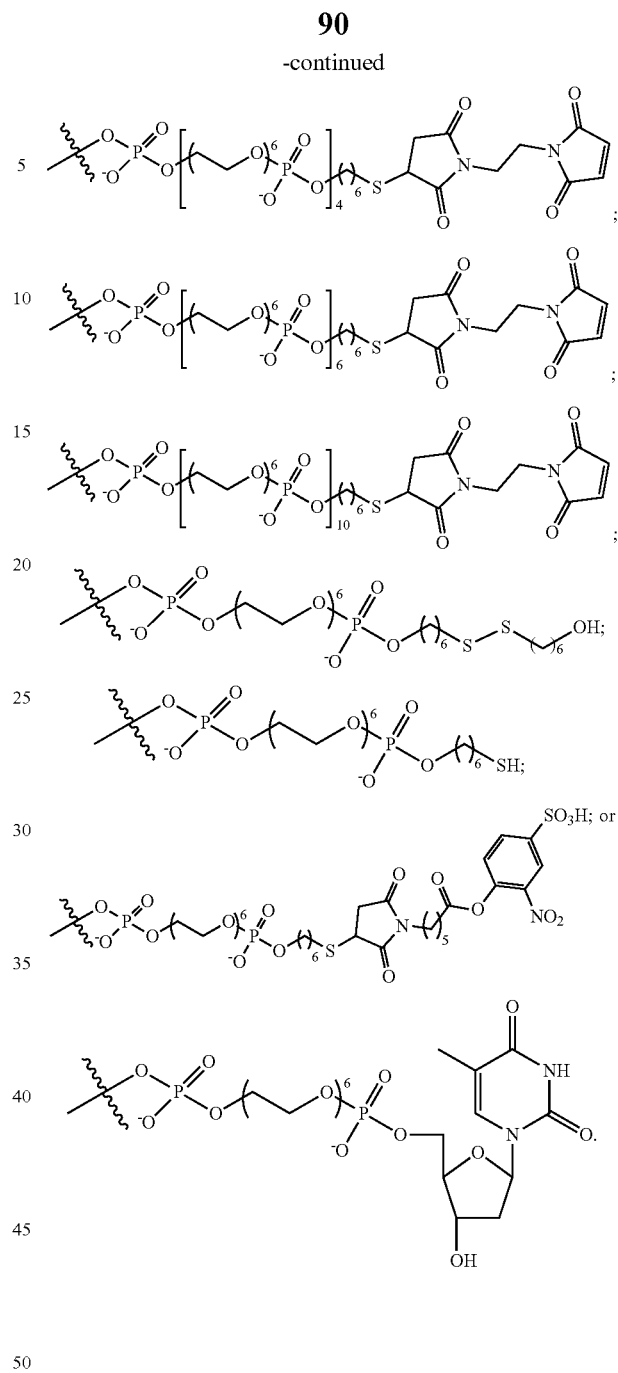
20. The compound of claim 1, wherein M1 and M2 at each occurrence, independently have one of the following structures:
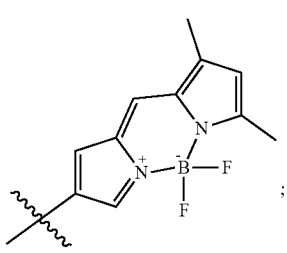

91
-continued
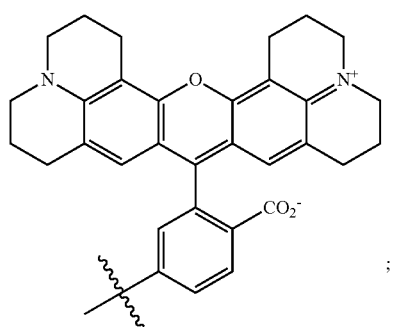
;
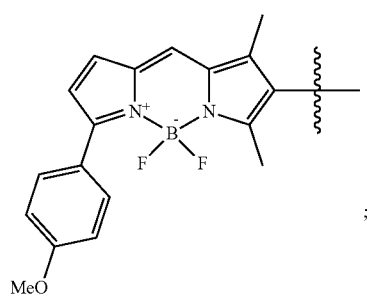
;
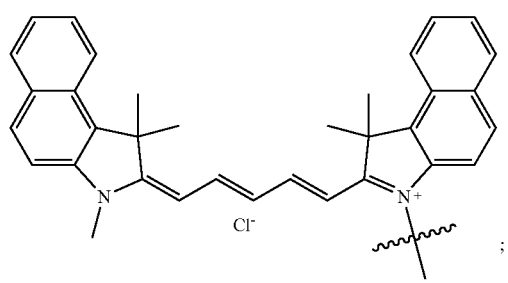
;
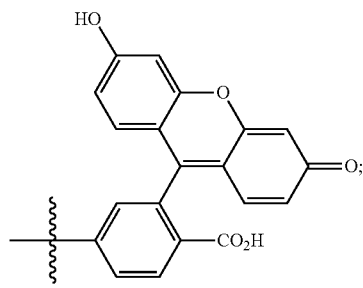
;
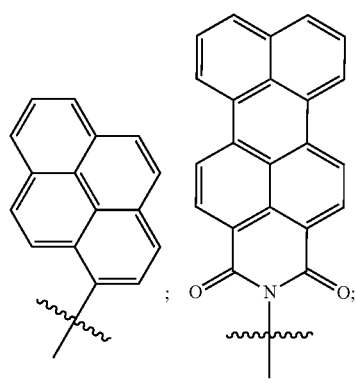
;
92
-continued
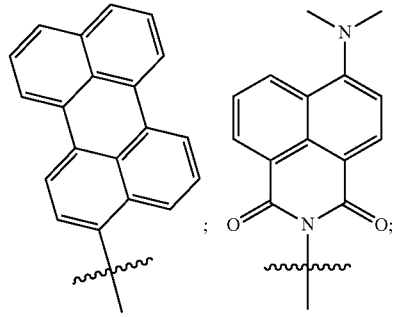
;
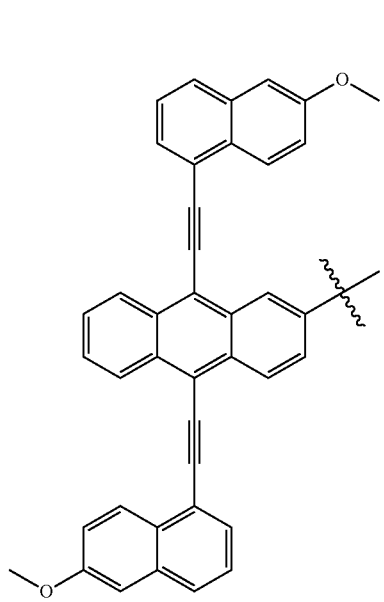
or
.

21. The compound of claim 1, wherein the compound has one of the following structures:
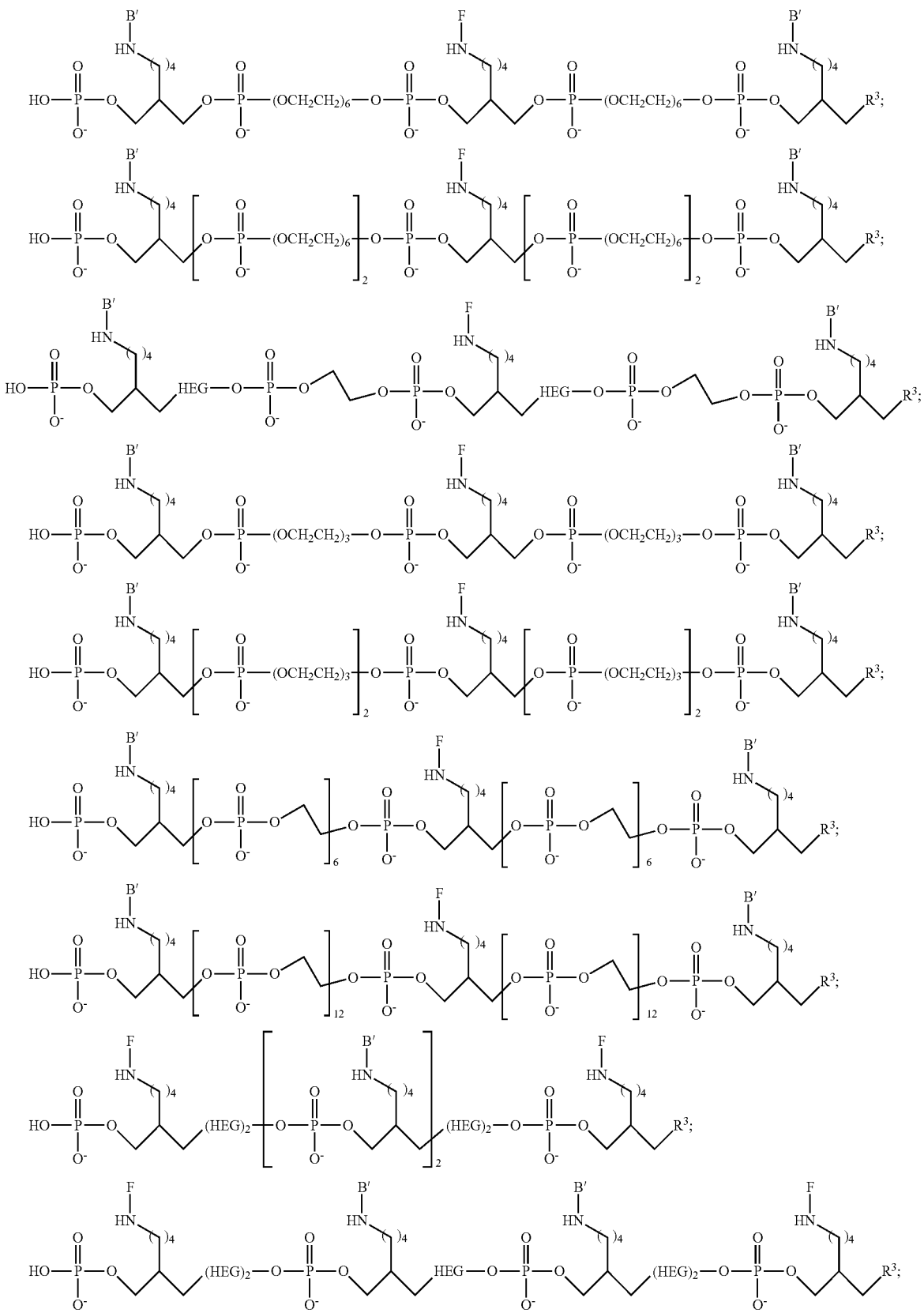

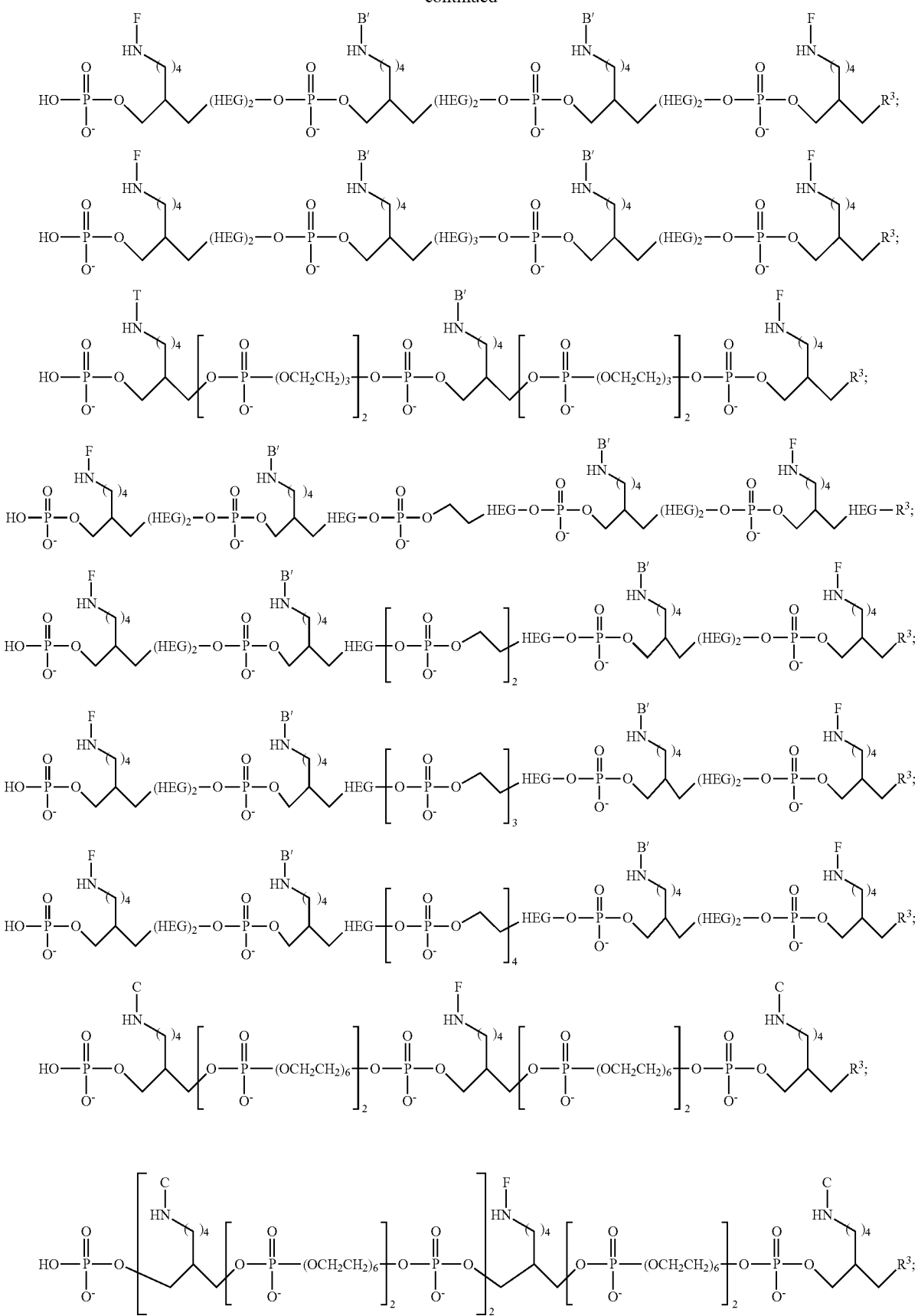

-continued
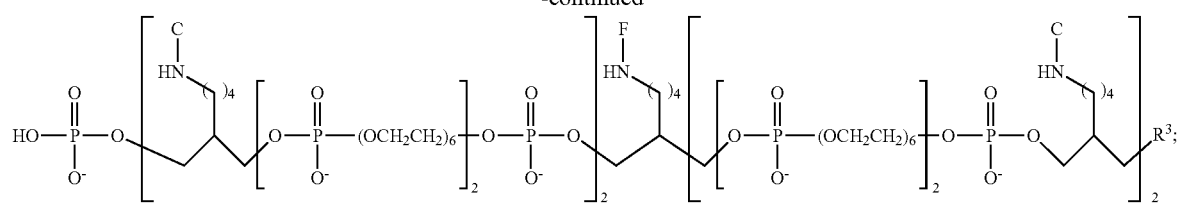
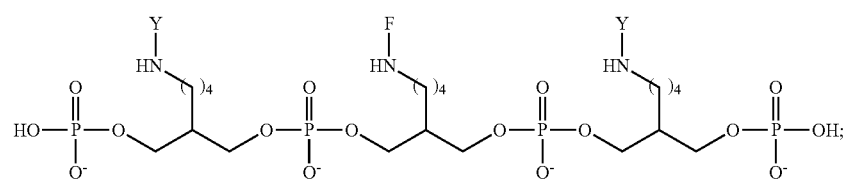
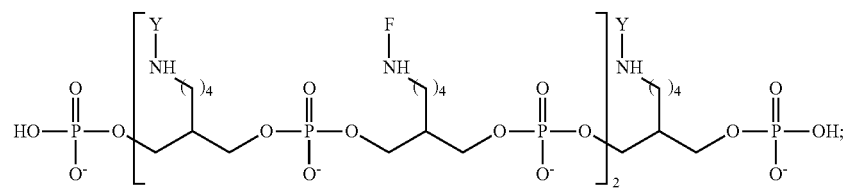
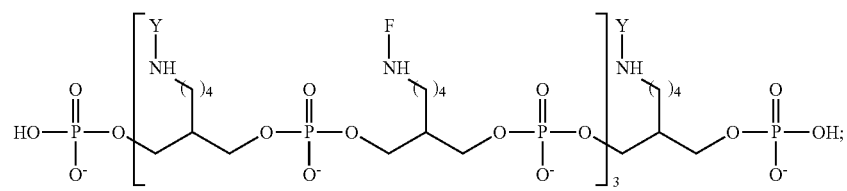
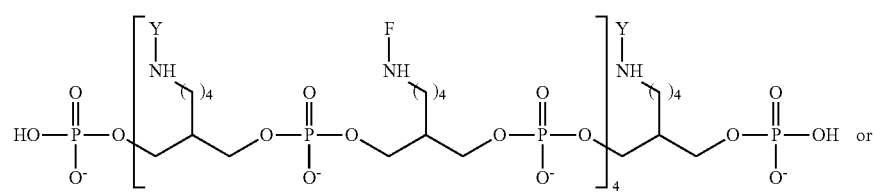 or
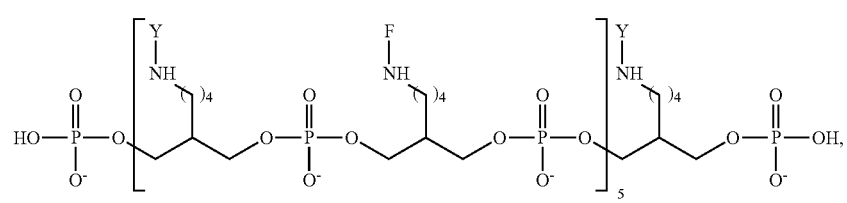

wherein HEG, R³, dT, B, B', C, F, T and Y have the following structures, respectively:
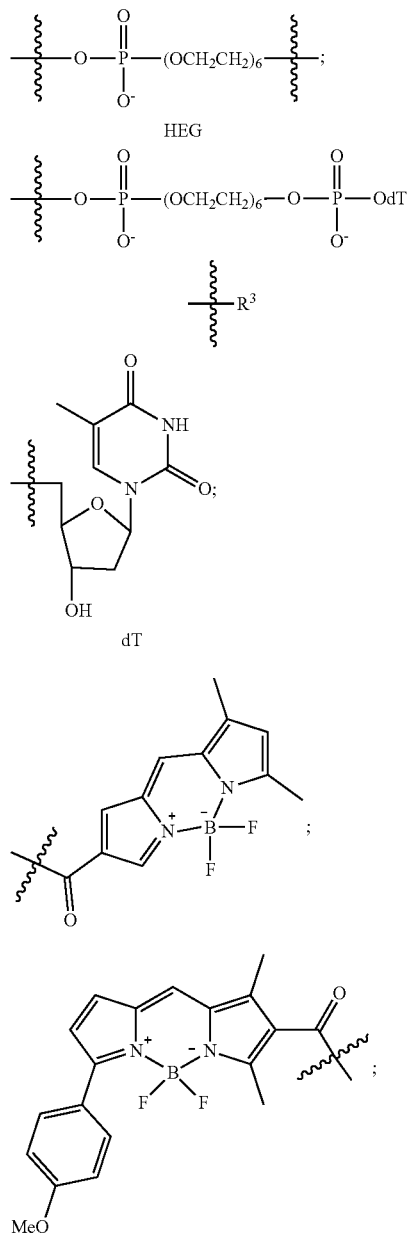
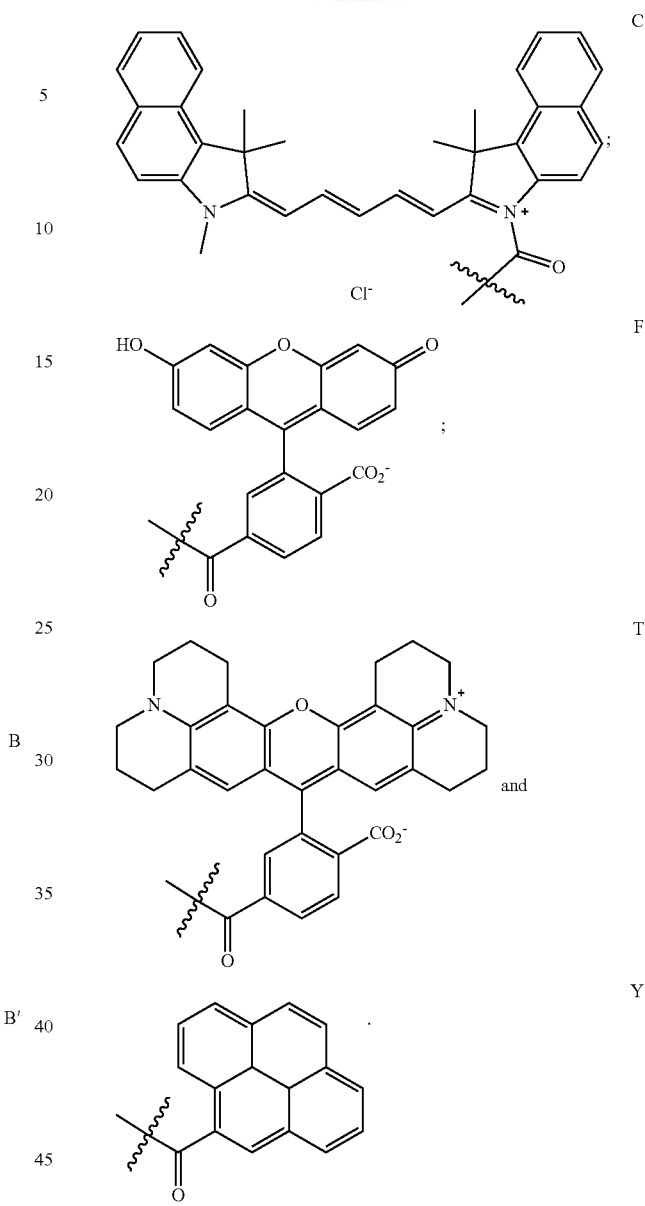
22. The compound of claim 7, wherein the compound has one of the following structures:
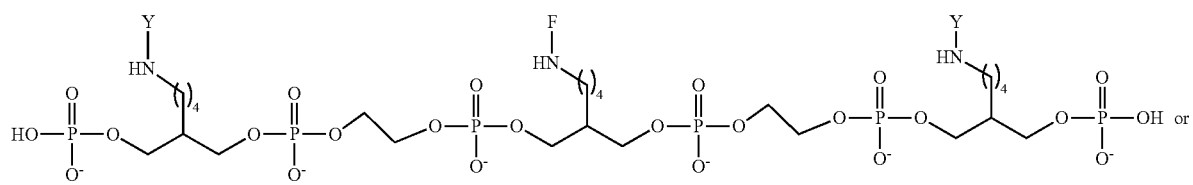

101

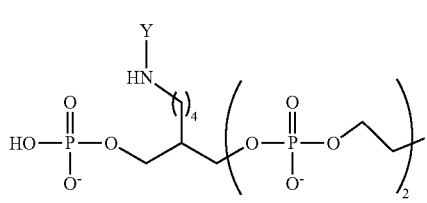

102

-continued

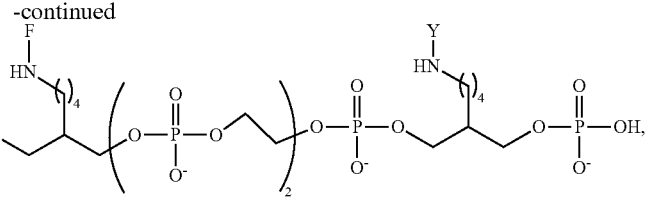

wherein F and Y have the following structures, respectively:

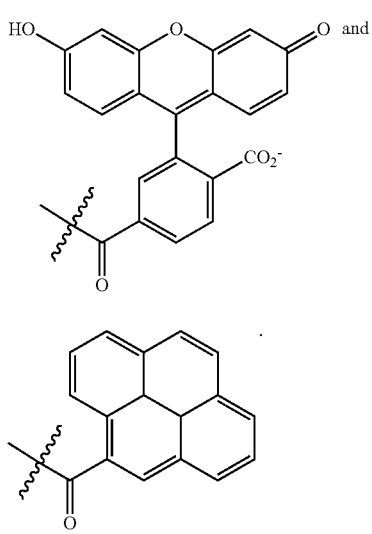

23. A method of staining a sample, comprising adding to said sample the compound of claim 1 in an amount sufficient to produce an optical response when said sample is illuminated at an appropriate wavelength.

24. A method for visually detecting an analyte molecule, the method comprising:
 (a) providing the compound of claim 1, wherein the compound comprises a covalent bond to the analyte molecule; and
 (b) detecting the compound by its visible properties.

25. A method for visually detecting an analyte molecule, the method comprising:
 (a) ad-mixing the compound of claim 1, wherein the compound comprises a covalent bond to Q, with the analyte molecule;
 (b) forming a bio-conjugate of the compound and the analyte molecule; and
 (c) detecting the bio-conjugate by its visible properties.

* * * * *